(12) United States Patent
Schoenbrunner et al.

(10) Patent No.: US 8,986,673 B2
(45) Date of Patent: Mar. 24, 2015

(54) **REPLICATION STABLE AND RNASE RESISTANT CHIMERAS OF *PESTIVIRUS* WITH INSERTION IN 3' NONTRANSLATED REGION (3'NTR)**

(75) Inventors: Erhard Ralf Schoenbrunner, Moraga, CA (US); Sven-Erik Behrens, Halle (DE)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/470,148

(22) Filed: May 11, 2012

(65) Prior Publication Data

US 2012/0231539 A1 Sep. 13, 2012

Related U.S. Application Data

(63) Continuation of application No. 12/277,282, filed on Nov. 24, 2008, now abandoned.

(51) Int. Cl.
*A01N 63/00* (2006.01)
*C12N 15/00* (2006.01)
*C07H 21/02* (2006.01)
*C12N 7/00* (2006.01)
*C12N 15/86* (2006.01)

(52) U.S. Cl.
CPC . *C12N 7/00* (2013.01); *C12N 15/86* (2013.01); *C07H 21/02* (2013.01); *C12N 2770/24211* (2013.01); *C12N 2770/24222* (2013.01); *C12N 2770/24311* (2013.01); *C12N 2770/24322* (2013.01)
USPC ............ 424/93.2; 435/320.1; 536/23.1

(58) Field of Classification Search
CPC ............ C12N 15/86; C12N 2770/24211; C12N 2770/24222; C12N 2770/24311; C12N 2770/24322; C07H 21/02
USPC ............ 424/93.2; 435/320.1; 536/23.1
See application file for complete search history.

(56) References Cited

U.S. PATENT DOCUMENTS

| | | | |
|---|---|---|---|
| 5,677,124 | A | 10/1997 | DuBois et al. |
| 5,912,145 | A | 6/1999 | Stanley |
| 5,919,625 | A | 7/1999 | DuBois et al. |
| 5,939,262 | A | 8/1999 | Pasloske et al. |
| 6,001,613 | A | 12/1999 | Donis et al. |
| 6,127,116 | A | 10/2000 | Rice et al. |
| 6,214,982 | B1 | 4/2001 | Pasloske et al. |
| 6,326,137 | B1 | 12/2001 | Hong et al. |
| 6,399,307 | B1 | 6/2002 | Pasloske et al. |
| 7,009,044 | B1 | 3/2006 | Nam et al. |
| 7,033,749 | B2 | 4/2006 | Pasloske et al. |
| 7,141,405 | B2 | 11/2006 | Martin et al. |
| 7,183,084 | B2 | 2/2007 | Jaeger |
| 7,192,745 | B2 | 3/2007 | Jaeger |
| 7,473,772 | B2 | 1/2009 | Martin et al. |

| | | |
|---|---|---|
| 2006/0105365 A1 | 5/2006 | Martin et al. |
| 2006/0257889 A1 | 11/2006 | Pasloske et al. |
| 2010/0129902 A1 | 5/2010 | Schoenbrunner et al. |

FOREIGN PATENT DOCUMENTS

| | | |
|---|---|---|
| EP | 0701627 | 1/1997 |
| EP | 0910643 | 8/2006 |
| WO | WO-94/28171 | 12/1994 |
| WO | WO-95/15974 | 6/1995 |
| WO | WO-98/00547 | 1/1998 |
| WO | WO-99/55366 | 11/1999 |
| WO | WO-00/75352 | 12/2000 |
| WO | WO-2007/002793 | 1/2007 |
| WO | WO-2010/060114 | 5/2010 |

OTHER PUBLICATIONS

Becher et al., 2000, Journal of Virology, vol. 74, No. 17, p. 7884-7894.*
Frolov et al., 1998, RNA, vol. 4, p. 1418-1435.*
Pankraz et al., 2009, Journal of Virology, vol. 83, No. 23, p. 12415-12423.*
U.S. Appl. No. 12/277,282, "Final Office action mailed Jan. 11, 2012".
U.S. Appl. No. 12/277,282, "Office action mailed Mar. 23, 2011".
U.S. Appl. No. 12/277,282, "Office Action Mailed Apr. 5, 2010".
U.S. Appl. No. 12/277,282, "Office Action Mailed Jul. 20, 2011".
U.S. Appl. No. 12/277,282, "Office Action Mailed Jul. 30, 2010".
U.S. Appl. No. 12/277,282, "Response to Mar. 23, 2011 Final Office Action Filed May 9, 2011".
U.S. Appl. No. 12/277,282, "Response to Apr. 5, 2010 Office Action (Restriction Requirement) Filed Jun. 1, 2010".
U.S. Appl. No. 12/277,282, "Response to Jul. 20, 2011 Office Action Filed Nov. 14, 2011".
U.S. Appl. No. 12/277,282, "Response to Jul. 30, 2010 Non-final Office Action Filed Jan. 31, 2011".
Altmeyer, R. et al., "Attenuated Mengo virus as a vector for immunogenic human immunodeficiency virus type 1 glycoprotein 120", *PNAS*, vol. 91(21), 1994, 9775-9779.
Ansardi, D. C. et al., "Encapsidation and serial passage of a poliovirus replicon which expresses an inactive 2A proteinase", *J. Virol.*, vol. 69(2), 1995, 1359-1366.
Azrolan, N. et al., "A Solution Hybridization / RNase Protection Assay with Riboprobes to Determine Absolute Levels of apoB, A-I and E mRNA in Human Hepatoma Cell Lines", *J. Lipid Res.*, vol. 31, 1990, 1141-1146.
Baroth, M. et al., "Stable recombinants of bovine viral diarrhea virus containing a hepatitis C virus insert", *J. Gen. Virol*, vol. advance e-pub, Jan. 6, 2010.

(Continued)

*Primary Examiner* — Shin Lin Chen

(57) ABSTRACT

The invention relates to the field of nucleic acid amplification, particularly to quality control materials for use in viral RNA assays. It specifically relates to the construction of a recombinant *Pestivirus* by the identification of a region in the 3'NTR of the viral RNA genome where additional sequence elements can be stably inserted. Chimeric *Pestivirus* with sequence insertions in the 3' nontranslated region (3'NTR) of the viral RNA genome were stable in replication and capable of forming infectious, RNase resistant virus particles. This chimeric *Pestivirus* with a 3'NTR insertion can be utilized as a quality control material in analytical assays for RNA targets, including external, internal controls, quantitative standards in PCR and NAT nucleic acid assays.

18 Claims, 25 Drawing Sheets

(56) References Cited

OTHER PUBLICATIONS

Becher, P. et al., "Complete Genomic Sequence of Border Disease Virus, a Pestivirus from Sheep", *J. Virol.*, vol. 72(6), 1998, 5165-5173.

Becher, P. et al., "Mutations in the 5' Nontranslated Region of Bovine Viral Diarrhea Virus Result in Altered Growth Characteristics", *J. Virol.*, vol. 74(17), 2000, 7884-7894.

Behrens, et al., "Cis- and Trans-acting Determinants of Flaviviridae Replication", *Molecular Biology of the Flavivirus: Horizon Bioscience*, 2006, 101-134.

Behrens, S. E. et al., "Characterization of an Autonomous Subgenomic Pestivirus RNA Replicon", *J. Virol.*, vol. 72(3), 1998, 2364-2372.

Choi, W. S. et al., "Expression of Human Immunodeficiency Virus Type 1 (HIV-1) gag, pol, and env Proteins from Chimeric HIV-1 Poliovirus Minireplicons", *J. Virology*, vol. 65(6), 1991, 2875-2883.

Deng, R. et al., "5' and 3; Untranslated Regions of Pestivirus Genome: Primary and Secondary Structure Analyses", *Nucleic Acids Research*, vol. 21(8), 1993, 1949-1957.

Derse, D. et al., "Construction of a recombinant bovine leukemia virus vector for analysis of virus infectivity", *J. Virol.*, vol. 64(1), 1990, 401-405.

Dichek, D. A. et al., "Characterization of Recombinant Plasminogen Activator Production by Primate Endothelial Cells Transduced with Retroviral Vectors", *Blood*, vol. 84, 1994, 504-516.

Donson, J. et al., "Systemic expression of a bacterial gene by a tobacco mosaic virus-based vector", *PNAS*, vol. 88(16), 1991, 7204-7208.

FDA, "Guidance for Industry in the Manufacture and Clinical Evaluation of In Vitro Tests to Detect Nucleic Acid Sequences of Human Immunodeficiency Viruses Types 1 and 2", *Section III G*.

Filocamo, G. et al., "Chimeric Sindbis viruses dependent on the NS3 protease of hepatitis C virus", *J. Virol.*, vol. 71(2), 1997, 1417-1427.

Frolov, et al., "cis-acting RNA elements required for replication of bovine viral diarrhea virus-hepatitis C virus 5' nontranslated region chimeras", *RNA*, 4, 1998, 1418-1435.

Frolov, Ilya et al., "Alphavirus-based expression vectors: strategies and applications", *PNAS*, vol. 93(21), 1996, 11371-11377.

Gallie, D. R. et al., "In Vivo Uncoating and Efficient Expression of Foreign mRNAs Packaged in TMV-Like Particles", *Science*, vol. 236, May 1987, 1122-1124.

Giavedoni, L. D. et al., "Vaccinia virus recombinants expressing chimeric proteins of human immunodeficiency virus and gamma interferon are attenuated for nude mice", *PNAS*, vol. 89(8), 1992, 3409-3413.

Grassman, C. et al., "Hepatitis C Virus and the Related Bovine Viral Diarrhea Virus Considerably Differ in the Functional Organization of the 5' Non-translated Region: Implications for the Viral Life Cycle", *Virology*, vol. 15:333(2), 2005, 349-366.

Gritz, L. et al., "Generation of Hybrid Genes and Proteins by Vaccinia Virus-Mediated Recombination: Application to Human Immunodeficiency Virus Type 1 env", *J. Virology*, vol. 64(12), Dec. 1990, 5948-5957.

Hanecak, R. et al., "Antisense Oligonucleotide Inhibition of Hepatitis C Virus Gene Expression in Transformed Hepatocytes", *J. Virology*, vol. 70(8), Aug. 1996, 5203-5212.

Harrison, B. D. et al., "Milestones in the Research on Tobacco Mosaic Virus", *Phil. Trans. R. Soc. London*, B 354, 1999, 521-529.

Heidenreich, O et al., "Chemically Modified RNA: Approaches and Applications," *FASEB J.*, vol. 7(1), Jan. 1993, 90-96.

Hwang, D-J et al., "Expression of tobacco mosaic virus coat protein and assembly of pseudovirus particles in *Escherichia coli*", *PNAS*, vol. 91(19), 1994, 9067-9071.

Isken, O. et al., "Complex signals in the genomic 3' non-translated region of bovine viral diarrhea virus coordinate translation and replication of the viral RNA", *RNA*, vol. 10, 2004, 1637-1652.

Isken, O. et al., "Members of the NF90/NFAR Protein Group are Involved in the Life Cycle of a Positive-Strand RNA Virus", *EMBO J.*, vol. 22, 2003, 5655-5665.

Isken, O. et al., "Nuclear Factors are Involved in Hepatitis C Virus RNA Replication", *RNA*, vol. 13, 2007, 1675-1692.

ISO Standard 17511, 2003.

Jupin, I. et al., "Direct recovery of in vitro transcripts in a protected form suitable for prolonged storage and shipment at ambient temperatures", *Nucl. Acids Res.*, vol. 17(2), 1989, 815.

Khromykh, Alexander A. et al., "Encapsidation of the Flavivirus Kunjin Replicon RNA by Using a Complementation System Providing Kunjin Virus Structural Proteins in tans", *J. Virol.*, vol. 72, Jul. 1998, 5967-5977.

Khromykh, Alexander A. et al., "trans-Complementation of Flavivirus RNA Polymerase Gene NS5 by Using Kunjin Virus Replicon-Expressing BHK Cells", *J. Virol.*, vol. 72, Sep. 1998, 7270-7279.

Kohara, Michinori et al., "Expression and characterization of glycoprotein gp35 of hepatitis C virus using recombinant vaccinia virus", *J. Gen. Virol.*, vol. 73, Sep. 1992, 2313-2318.

Kumagai, M. et al., "Rapid, high-level expression of biologically active alpha-trichosanthin in transfected plants by an RNA viral vector", *PNAS*, vol. 90(2), 1993, 427-430.

Lee, Haekyung et al., "The C-Terminal Hydrophobic Domain of Hepatitis C Virus RNA Polymerase NS5B Can Be Replaced with a Heterologous Domain of Poliovirus Protein 3A", *J. Virol.*, vol. 80, Nov. 1, 2006, 11343-11354.

Lim, Francis et al., "tations that increase the affinity of a translational repressor for RNA", *Nucl. Acids Res.*, vol. 22(18), 1994, 3748-3752.

Lindenbach, et al., "Flaviviridae: The Viruses and their Replication", *Fields Virology*, 5th ed., Knipe, et al., Lippincott, 2007, 1101-1152.

Lohmann, V. et al., "Replication of Subgenomic Hepatitis C Virus RNAs in Hepatoma Cell Line", *Science*, vol. 285(5424), 1999, 110-113.

Lu, H. H. et al., "Poliovirus chimeras replicating under the translational control of genetic elements of hepatitis C virus reveal unusual properties of the internal ribosomal entry site of hepatitis C virus", *PNAS*, vol. 93(4), 1996, 1412-1417.

Makoschey, et al., "Bovine Viral Diarrhea Virus with Deletions in the 5'-Nontranlated Region: Reduction of Replication in Calves and Induction of Protective Immunity", *Vaccine*, vol. 22, 2004, 3285-3294.

Mamounas, M. et al., "An infectious chimeric human immunodeficiency virus type 2 (HIV-2) expressing the HIV-1 principal neutralizing determinant", *J. Virol.*, vol. 69(10), Oct. 1995, 6424-6429.

Meyers, G. et al., "Recovery of Cytopathogenic and Noncytopathogenic Bovine Viral Diarrhea Viruses from cDNA Contructs", *J. Virology*, vol. 70, 1996, 9603-9613.

Mivechi, Nahid F. et al., "Use of Polymerase Chain Reaction to Detect the Expression of the Mr 70,000 Heat Shock Genes in Control or Heat Shock Leukemic Cells as Correlated to Their Heat Response", *Cancer Res.*, vol. 50, May 15, 1990, 2877-2884.

Molecular Diagnostic Methods for Infectious Disease, Approved Guideline, *2nd ed., Clinical and Laboratory Standards Institute*, vol. 26(8), 2006.

Monroe, S. S. et al., "Sequence analysis of cDNA's derived from the RNA of Sindbis virions and of defective interfering particles", *J. Virol.*, vol. 41, Jan. 1982, 153-162.

Nolte, F. S. et al., "Clinical evaluation of two methods for genotyping Hepatitis C virus based on analysis of the 5' noncoding region", *J. Clin. Microbiol.*, vol. 41, No. 4, Apr. 2003, 1558-1564.

Olkkonen, V. M. et al., "In vitro assembly of infectious nucleocapsids of bacteriophage phi 6: formation of a recombinant double-stranded RNA virus", *PNAS*, vol. 87(23), 1990, 9173-9177.

Onodera, S. et al., "Construction of a transducing virus from double-stranded RNA bacteriophage phi6: establishment of carrier states in host cells", *J. Virol.*, vol. 66, Jan. 1992, 190-196.

Page, K. A. et al., "Construction and use of a human immunodeficiency virus vector for analysis of virus infectivity", *J. Virol.*, vol. 64(11), Nov. 1990, 5270-5276.

Pal-Ghosh, R. et al., "A poliovirus minireplicon containing an inactive 2A proteinase is expressed in vaccinia virus-infected cells", *J. Virol.*, vol. 67(8), Aug. 1993, 4621-4629.

(56) References Cited

OTHER PUBLICATIONS

Pankraz, A. et al., "Essential and nonessential elements in the 3' nontranslated region of bovine viral diarrhea virus", *J. Virol*, vol. 79, No. 14, Jul. 2005, 9119-9127.
Pape, M. E. et al., "Molecular cloning, sequence, and expression of cynomolgus monkey cholesteryl ester transfer protein. Inverse correlation between hepatic cholesteryl ester transfer protein mRNA levels and plasma high density lipoprotein levels", *Arterioscler Thromb Vasc Biol.*, vol. 11, 1991, 1759-1771.
Pape, M. E. et al., "mRNA Quantitation by a Simple and Sensitive RNAse Protection Assay", *GATA*, vol. 8(7), 1991, 206-213.
Pape, M. E. et al., "Select this articleAn improved method for precise quantitation of cellular and tissue apolipoprotein A-I mRNA levels by use of an internal standard", 1990, *J. Lipid Res.*, vol. 31(4), 1990, 727-733.
Pasloske, Britton L. et al., "Armored RNA Technology for Production of Ribonuclease-Resistant Viral RNA Controls and Standards", *J. Clin. Microbiol.*, vol. 36(12), Dec. 1998, 3590-3594.
PCT/US09/65826, "International Search Report Mailed on Oct. 3, 2010".
Perrault, J. et al., "Internal genome deletions in two distinct classes of defective interfering particles of vesicular stomatitis virus", *PNAS*, Vo. 76(12), 1979, 6191-6195.
Pickett, Gavin G. et al., "Encapsidation of heterologous RNAs by bacteriophage MS2 coat protein", *Nucl. Acids Res.*, vol. 21(19), 1993, 4621-4626.
Porter, D. C. et al., "Encapsidation of genetically engineered poliovirus minireplicons which express human immunodeficiency virus type 1 Gag and Pol proteins upon infection", *J. Virol.*, vol 67, Jul. 1993, 3712-3719.
Puig, M. et al., "Detection of adenoviruses and enteroviruses in polluted waters by nested PCR amplification", *Appl. Environ. Microbiol.*, vol. 60, Aug. 1994, 2963-2970.
Qiao, X. et al., "Interference with bacteriophage phi 6 genomic RNA packaging by hairpin structures", *J. Virol.*, vol. 69, Sep. 1995, 5502-5505.
Qu, Lin et al., "Isolation and Characterization of Noncytopathic Pestivirus Mutants Reveals a Role for Nonstructural Protein NS4B in Viral Cytopathogenicity", *J. Virol.*, vol. 75, Nov. 2001, 10651-10662.
Roth, W. K. et al., "Comparison of two quantitative hepatitis C virus reverse transcriptase PCR assays", *J. Clin. Microbiol.*, vol. 34(2), Feb. 1996, 261-264.
Ruster, B. et al., "Quantification of Hepatitis C Virus RNA by Competitive Reverse Transcription and Polymerase Chain Reaction Using a Modified Hepatitis C Virus RNA Transcript", *Analytical Biochemistry*, vol. 224(2), Jan. 1995, 597-600.
Seeger, et al., "Expression of infectious woodchuck hepatitis virus in murine and avian fibroblasts", *J. Virol.*, vol. 63, Nov. 1989, 4665-4669.
Shafer, G. E. et al., "Expression of a swine class II gene in murine bone marrow hematopoietic cells by retroviral-mediated gene transfer", *PNAS*, vol. 88(21), 1991, 9760-9764.
Shyamala, V. et al., "Detection, Validation and Quantification of West Nile Virus RNA by the Alternate NAT WNV Assay", *AABB Poster*, 2003.
Sleat, D. E. et al., "Packaging of Recombinant RNA Molecules into Pseudovirus Particles Directed by the Origin-of-Assembly Sequence from Tobacco Mosaic Virus RNA", *Virology*, vol. 155, 1986, 299-308.
Smith, A. D. et al., "Use of random systematic mutagenesis to generate viable human rhinovirus 14 chimeras displaying human immunodeficiency virus type 1 V3 loop sequences", *J. Virol.*, vol. 68, Jan. 1994, 575-579.
Stettler, P. et al., "Establishment and Application of Bicistronic Classical Swine Fever Virus Genomes for Foreign Gene Expression and Complementation of E2 Deletion Mutants", *Virus Research*, vol. 85, Feb. 2002, 173-185.
Tautz, N. et al., "Cytopathogenicity of a Pestivirus Correlates with a 27-Nucleotide Insertion", *J. Virology*, vol. 70(11), 1996, 7851-7858.
Tautz, N. et al., "Establishment and Characterization of Cytopathogenic and Noncytopathogenic Pestivirus Replicons", *J. Virol.*, vol. 73, Nov. 1999, 9422-9432.
Turner, D. R. et al., "Assembly of hybrid RNAs with tobacco mosaic virus coat protein: Evidence for incorporation of disks in 5'-elongation along the major RNA tail", *J. Mol. Biol.*, vol. 209(3), Oct. 5, 1989, 407-422.
Vassilev, V. B. et al., "Authentic and Chimeric Full-Length Genomic cDNA Clones of Bovine Viral Diarrhea Virus That Yield Infectious Transcripts", *J. Virology*, vol. 71, 1997, 471-478.
Vella, Cherelyn et al., "Characterization and primary structure of a human immunodeficiency virus type 1 (HIV-1) neutralization domain as presented by a poliovirus type 1/HIV-1 chimera", *J. Gen. Virol.*, vol. 74, Dec. 1993, 2603-2607.
Vilcek, S., "Genetic variability of bovine viral diarrhoea virus sUbtypes at 3'-nontranslated region", *Virus Genes, Kluwer Academic Publishers*, vol. 34, No. 1, Aug. 18, 2006, 31-35.
Walkerpeach, Cindy R. et al., "Ribonuclease-resistant RNA Controls (Armored RNA) for Reverse Transcription-PCR, Branched DNA, and Genotyping Assays for Hepatitis C Virus", *Clinical Chemistry*, vol. 45, 1999, 2079-2085.
Wang, A. J. et al., "Quantitation of mRNA by the polymerase chain reaction", *PNAS*, vol. 86(24), 1989, 9717-9721.
Widjojoatmodjo, M. et al., "Classical Swine Fever Virus ErnsDeletion Mutants: trans-Complementation and Potential Use as Nontransmissible, Modified, Live-Attenuated Marker Vaccines", *J. Virol.*, vol. 74, Apr. 2000, 2973-2980.
Wilson, T. M. et al., "Strategies to protect crop plants against viruses: pathogen-derived resistance blossoms", *PNAS*, vol. 90(8), 1993, 3134-3141.
Yu, H. et al., "Sequence and Structural Elements at the 3' Terminus of Bovine Viral Diarrhea Virus Genomica RNA: Functional Role during RNA Replication", *J. Virology*, vol. 73(5), 1999, 3638-3648.
Zhang, Hong et al., "Antisense Oligonucleotide Inhibition of Hepatitis C Virus (HCV) Gene Expression in Livers of Mice Infected with an HCV-Vaccinia Virus Recombinant", *Antimicrob. Agents Chemother.*, vol. 43, Feb. 1999, 347-353.
Isken, O., et al., "Complex signals in the genomic 3' non-translated region of bovine viral diarrhea virus coordinate translation and replication of the viral RNA"; RNA, vol. 10: 1637-1652; 2004.
Sarnow, P., et al.; "A poliovirus temperature-sensitive RNA synthesis mutant located in a noncoding region of the genome"; *PNAS*, 83:571-575; 1986.
Gorecki, D., "Prospects and problems of gene therapy: an update", *Expert Opinion Emerging Drugs*, vol. 6( 2), 2001, 187-198.
Kodama, K. et al., "The Features and Shortcomings for Gene Delivery of Current Non-Viral Carriers", *Current Medicinal Chemistry*, vol. 13, 2006, 2155-2161.
Lebedeva, I. et al., "Restoring apoptosis as a strategy for cancer gene therapy: focus on p53 and mda-7", *Seminars in Cancer Biology*, vol. 13, 2003, 169-178.
Thomas, C.. et al., "Progress and Problems With the Use of Viral Vectors for Gene Therapy", *Nature Reviews, Genetics*, vol. 4, 2003, 346-358.
Gebauer, M. et al., "A bi-cistronic, reporter-encoding bovine viral diarrhea virus applied in a new, effective diagnostic test", *Journal of General Virology*, vol. 95, Apr. 17, 2014, 1522-1531 (including Supplement).

* cited by examiner

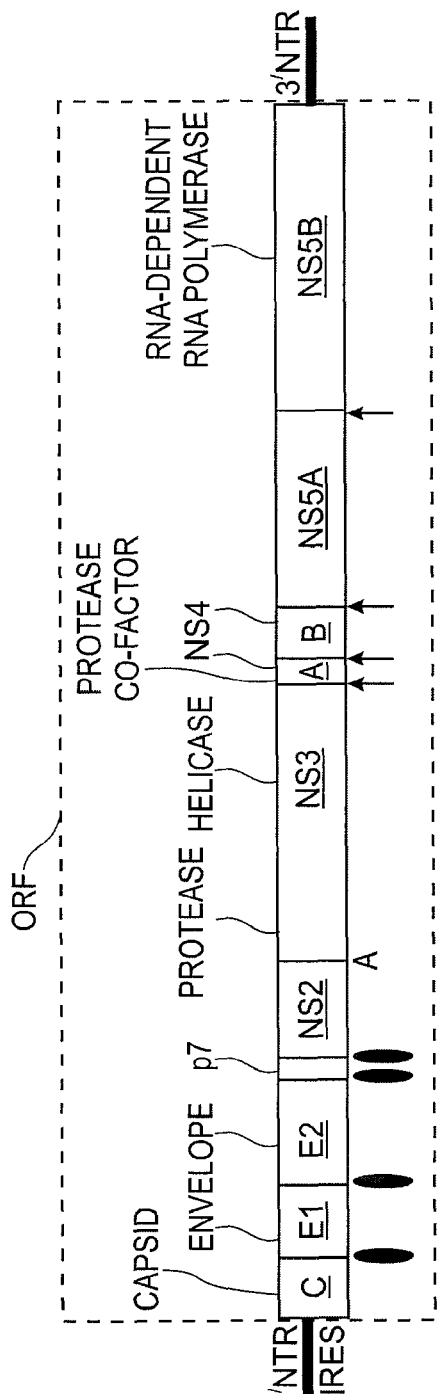
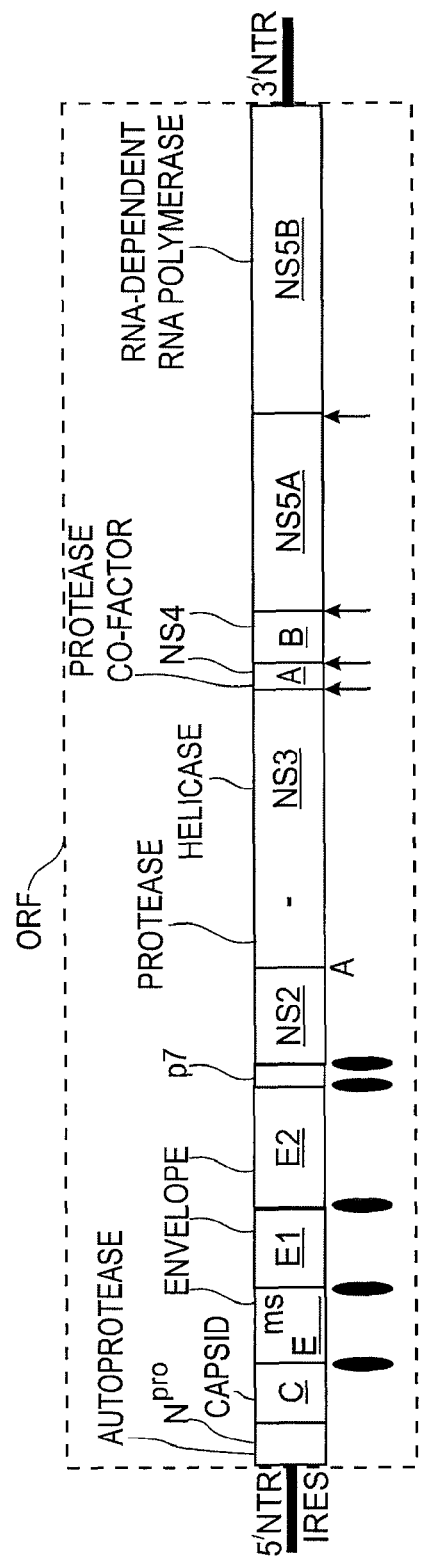
FIG. 1A
HCV GENOME
FIG. 1B
BVDV GENOME

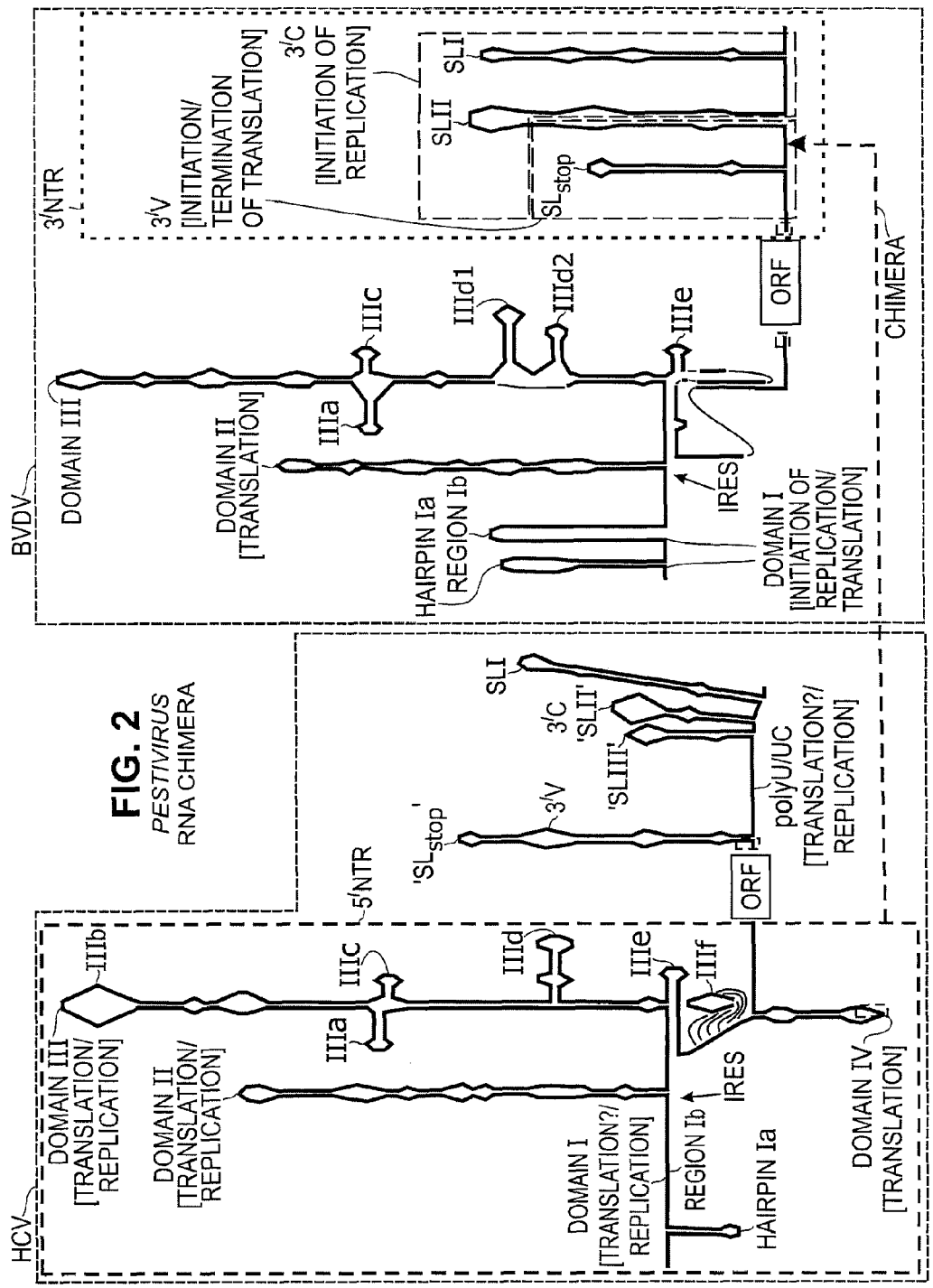
FIG. 2 *PESTIVIRUS* RNA CHIMERA

FIG. 4
3'NTR OF BVDV

FIG. 5A

| VIRUS STRAIN | "UGA BOX"/POSITION |
|---|---|
| BDV X818 | 46 AAU UGU AUA UAU 57 |
| BDV A841/1 | 46 GAU UGU AUA UAA 57 |
| CSFV C-strain | 43 UAU UGU AGA UAA 54 |
| CSFV Alfort-T | 43 UAU UGU AAA UAA 54 |
| BVDV-1 NADL | 44 UAG UGU AUA UAA 55 |
| BVDV-1 Osloss | 43 UAU UAU AUA UAA 54 |
| | 46 UAU UGU ACA UAA 57 |
| BVDV-1 CP7 | 46 UAU UAU GUU UAA 57 |
| | 19 UAU UGU ACA UAA 30 |
| BVDV-2 890 | 46 AAA UAU GGU GAA 57 |
| Singer | 43 UAU UGU AUA UAA 54 |
| | 46 UAU UGU AAA UAA 57 |

CONSENSUS SEQUENCE

```
gtatacgaggttaggcaagttctcgtatacatattggacactctaaaaataattaggcctagggga
caaaaatcctccttagcgaaggccgaaaagaggctaaccatgcccttagtaggactagcaaaataa
gggggtagcaacagtggcgagttcgttggatggctgaagccctgagtacagggtagtcgtcagtg
gttcgacgctttggaggacaagcctcgagatgccacgtggacgagggcatgcccacagcacatctt
aacctggacaggggtcgttcaggtgaaaacggtttaaccaaccgctacgaatacagtctgatagga
tgctgcagaggcccactgtattgctactgaaaatctctgctgtacatggcacatggagttgatcac
aaatgaacttttatacaaaacatacaaacaaaaacccgctggagtggaggaaccagtatacgacca
agctggtaacccctttgtttggagaaagaggagtgattcatccgcagtcaacgctaaaacttccaca
taaaagaggggagcgtgaagtccccaccaatctggcttcttttaccaaaaagaggtgactgcaggtc
gggtaacagcaaggggcctgtgagtggaatctacttaaaaccagggccgttattctaccaagatta
taaaggacctgtctatcatagagccccattggagttttttgaggaggcgtctatgtgtgagacaac
taaaagaataggggagagtaactggtagtgacagcagattataccacatttacgtgtgtattgatgg
gtgcataatagtcaagagtgctacaaaagaccgccagaaagtactcaagtgggtccacaacaagct
aaactgccccctatgggtttcaagctgctccgacacaaaagatgaaggggtggtgaggaagaagca
acaaaagccagataggttggaaaaggggagaatgaagataacacctaaggagtcagagaaagacag
taagaccaagccgccagatgctacgatagtggtagatggagtcaagtatcaggtaaagaaaaaagg
aaaagtcaagagcaagaacacccaggacggcttataccacaacaaaaataaacctcaagagtcgcg
caagaaactagagaaagcccctattggcctgggcaataatagccctggttttcttttcaagtcacaat
gggagagaacataacgcaatggaacttacaagataatggaacggaaggcatacaacgagccatgtt
tcaaagaggagtgaatagaagttttacatgggatctggccagagaaaatctgtacaggtgttccttc
ccacctggccactgacacagaattgaaggcaattcatggtatgatggatgcaagtgagaagacaaa
ttatacgtgctgcagactccaacgccatgaatggaacaaacatggttggtgcaactggtacaacat
tgaaccttggatcctccttatgaataaaactcaggccaaccttactgagggtcagccactaaggga
gtgtgccgtcacatgccggtatgatcgagatagtgacctgaatgtagtaacacaagccagggatag
ccccacaccattaacaggttgcaagaaaggcaaaaacttttcctttgcaggcatattggtacaagg
gccttgcaactttgaaatagccgtaagtgatgtgctgttcaaagagcatgattgcactagtgtgat
tcaagacagctcactacctcgtagacgggatgaccaactccctagagagtgccaggcaagggac
cgcgaaactaacaacttggctgggcaggcagcttgggatactaggaaagaaactggaaaacaagag
taagacatggtttggggcatatgcagcctctccctattgtgaggtagaacggaagcttggttacat
ctggtatacaaagaattgcactccagcctgtttgcctaggaatacaaagatcatcggccccggtag
gtttgacaccaatgccgaggatggtaaaatactgcatgagatggggggtcacttgtcggaggtgct
actactctcagtggtagtgctgtccgatttcgctccagagacagccagtgtgatatacttgattct
tcatttctccatcccacaaggacacactgatatacaagattgtgacaaaaccaactaaacctcac
cgtagaactcacaacagcagaagtaataccaggctcagtttggaacttgggtaaatatgtttgtgt
aagaccagattggtggccttatgagacagccacagtctggtgattgaagaggtgggtcaagtaat
taaggttgtcttaagggcgttaaaagatctgacgcgcatttggaccgctgctacaaccactgcatt
cttggtttgtctggtgaaggtagtgagaggccaagtgttacaaggtatactgtggctgatgctcat
aacaggggcgcaagggtacccagactgcaaacccggcttttcatacgccatagccaaaaatgatga
gattggcccacttggagctacaggcctcaccactcagtggtacgaatactcggatgggatgcggct
gcaggactcagtagttgaagtttggtgtaaaaatggagagatcaaatatctaatcagatgcgggag
ggaagccaggtatctggctgttctacacacgagagccttgccgacatctgtagtatttgaaaaaat
ttttgatgggaaagaacaagaggacatagtagaaatggatgacaactttgaattcggtctttgccc
gtgtgatgctagacccttgataaggggaaaatttaatacaacacttctaaatgggccagccttcca
gatggtttgccctataggatggacagggactgtaagctgtacactggccaataaggatacgttagc
cacaatcgttgtgaacgtataagaggtatgcaggccttttccatataggcaggactgtgtcaccca
gaaaaccatcggggaagacctctacgactgtgccttaggagggaattggacttgtgtgccgggga
tgcactacgatatgtagctgggcccgttgagtcttgtgagtggtgtgttacaagttttaaaaag
tgagggtctgccgcatttcccaatcggcaaatgcaggctgaagaatgagagtggctatagacaagt
ggatgagacttcttgcaacagaaacggcgtggctatagtgccatctggcacggtcaaatgcaagat
aggggacacggtggtgcaagtcattgcaatggatgataaactagggcctatgccttgcaaaccaca
tgaaatcatatccagtgaggggccagtggaaaagacggcatgcaccttcaactacacaagaacatt
aaaaaacaagtactttgagcccagggataactattttcaacaatacatgttaaaggggagtacca
atattggtttgacctagagatcactgaccaccaccgagattacttcgctgagtccctgttggtgat
agtagttgcactcctgggtgcaggtacgtgctttggtggtcacatacatgatcttatcaga
acagatggcctcgggtgtccagtatgggcaggtgaaatagtgatgatgggcaacttgttaacaca
tgacagtgttgaagtggtgacatatttcttactactataccactactaagagaggaaaacaccaa
aaaatgggtcatacttatataccacatcatagtaatgcatcctctaaaatcggtgacggtgatatt
gctaatggttggggggatggcaaaggctgaaccaggtgcccaggggtacctagagcaggtagacct
```

FIG. 6A

```
tagttttacgatgattacgatcatcgtaataggtctggttatagctaggcgtgatcccactgtggt
gccactagtcactatagtcgcggcactgaatgatcacaggactaggctttgggcccggagtggatgc
agctatggcagttctcaccttaaccctactgatgactagttatgtgacagactacttcaggtataa
aaggtggatacaatgtatcctcagcttagtagccggggtgttccttatccggaccctcaaacatct
aggtgaactcaaaaccctgagctgaccataccaaattggaggccactaaccttcatactattata
cctgacttcagcaacagttgttacaagatggaaaattgatatagctggcatattcctgcaaggggc
ccctatccttttgatgatcgccaccctatgggctgacttcttgactcttgttctgatcctacccac
ctacgaattagccaagctgtactacctaaagaacgtcaagactgacgtggagaagagttggctggg
ggggttagactacaggacaattgactctgtctatgatggtggatgaaagtggagaaggcgtgtacct
cttcccgtccagacagaagaaaaataagaatatcagcatactcttgcccctcatcagagctacgct
aataagttgtattagcagcaaatggcagatggtgtatatggcttacttaaccctggactttatgta
ctacatgcacagaaaggttattgaagagatatcagggagtaccaatgtgatgtctagagtgatagc
agcacttatagaattaaactggtccatggaagaagaagagagcaagggcttaaagaagtttttttat
actatctggaaggttgaggaaccttataataaagcataaggttaggaaccagactgtggcaagctg
gtatggggaggaagaagtctacggcatgccaaaagtcgtaaccataataagggcctgcacgctaaa
caagaacaaacattgcataatatgcacagtatgtgaggctagaaagtggaagggaggcaactgccc
taaatgcggccgccacgggaagcccatcatttgtgggatgactctagcggattttgaagaaaggca
ctacaagagaatttttataagggaaggtaactttgaaggacccttcaggcaggaatacaatgggtt
tgtacaatacaccgctagggggcaattgttcctgagaaatttacccatattggcaaccaaagtaaa
aatgatcatggtaggcaacctaggagaggaaatcggtgatctagaacacctaggatggatcctaag
gggacctgccgtgtgcaagaaaataactgagcacgaaaaatgccatgtcaacatactggacaagct
gactgcgttttttggagttatgccaagagggactacaccaagggctccggtgagattcccaacagc
actactaaaggtaaggaggggattggaaaccggttgcttacacgcatcaaggtggcataagctc
agtagaccatgtgaccgctggcaaggatctattggttttgtgacagtatgggtagaactagagtggt
ttgccaaagcaacaacaagttaactgatgagacagaatatggtgtcaagacggactccggatgtcc
agatggtgccagatgctatgtattaaacccagaggcagtaaatatatcagggtccaagggagctgt
cgtacacctccaaaaaacgggtggggaatttacatgtgttactgcatcaggtacaccggccttctt
cgacctgaaaaatttgaaaggatggtcgggtctacccatatttgaagcctccagcggcagagtggt
tggcagagtcaaagtgggaaagaatgaggaatccaaacccacaaaattaatgagtggtatccaaac
tgtttctaaaaatacggccgatttaacagaaaatggtcaagaagataaccagcatgaacaggggga
ctttaggcagataaccccttgcaacaggggcagggaagaccactgagctcccaaaagcagtgataga
ggagataggacgacacaaacgggtactagtgctcataccattaagagcagcagctgagtcagtcta
tcaatacatgagattgaaacacccaagtatctcctttaacctgagaataggggacatgaaagaagg
ggatatggcaaccgggatcacctacgcctcatatggatattttgccaaatgccacaaccaaagct
cagagcagcaatgatagagtattcatacatatttctggatgagtatcactgcgctactcctgagca
gttggctgtttataggaaaaattcacagattttctgagagcataagagtggttgccatgactgccac
cccagcagggtcagtaaccacaacaggcaaaaacacccaatagaagaattcatagcccctgaggt
gatgaaaggggaggaccttggaagccagttccttgacatagcggggttaaagatccctgtagagga
gatgaagggtaacatgttggttttcgtgcccacgaggaacatggcagttgaagtagccaagaaact
aaaagccaagggctacaactcagggtattactacagtggggaagacccagctaacttgagagtggt
aacatcacagtccccatacgtcgtggtagccactaatgccatcgagtcaggggtaacgctgccaga
tttagatacagttgttgacacaggtctgaaatgtgagaagagggtgagggtgtcttccaaaatacc
ctttatagtaacaggccttaagagaatggctgtcactgtgggcgaacaggctcagcggagaggcag
ggtaggtagagtgaaaacccggtaggtattataggaagtcaggaaacagcaaccgggtcaaggacta
ccactatgacttgttacaggcacagaggtacgggatcgaagatgggatcaacgtaacaaagtcctt
tagggagatgaattatgactggagcctgtatgaggaagacagcttgctgataacccagctggagat
actgaacaatctactcatctctgaagatttaccagcagctgttaaaacatcatggcaagaactga
tcacccagagcctatccagcttgcatataacagttatgaggtccaagtccctgtgctgttcccaaa
aataaggaatggggaggtcacagacacttacgagaactactcattcctaaatgcaaggaaactagg
ggaagacgtgccccgtgtacgtttatgccaccgaagatgaagatctggctggaccttctaggctt
ggactggccagacccagggaatcagcaagtagtggagactgggaaggcactgaagcaagtggtagg
actgtcctctgccgaaaatgccttgctcatagccctatttgggtatgtaggataccaagccttgtc
aaaaagacacgtcccaatgatcacagacatatacactatagaagatcaaagactagaggacacaac
ccaccttcaatatgcgcccaatgccataagaactgaggggaaggagactgaactaaaggaattagc
agtgggtgacttggacaaaatcatgggttccatctcggactatgcatcagagggattgaatttcgt
aaggtcccaagcagaaagatgagatctgccccgctttcaaagaaaacgtggaagctgctaaagg
gtacgtccaaaagtttattgattctctcatagaaaataaagaaaccataatcagatatggcctgtg
gggaacacacacggcactctacaagagtattgccgcgagattgggtcatgaaactgcattcgctac
```

FIG. 6B

```
actagtgataaagtggctggccttcgggggtgagtcggtgtcagaccacatgagacaagcagctgt
cgacctggttgtttattatgtgatcaataagccctccttcccaggggattctgaaacccaacagga
aggaaggcgattcgtcgccagcctgttcatctccgctttggcaacctacacatacaaaacttggaa
ttacaacaacctctccaaggtagtagaaccagccttagcatacctcccctatgctaccaatgcact
aaaaatgtttaccccgaccagactggagagcgtagttatacttagtaccacaatatacaaaactta
cctctcaataaggaagggaaagagtgatggactgttgggtacagggatcagtgcagcaatggagat
tctatcacagaacccagtgtcggtaggtatatctgtcatgctgggggtggggcgattgccgcgca
caatgccattgagtctagtgaacaaaaaggaccctgttgatgaaagtgtttgtaaaaaacttcct
ggaccaggcggcaacagatgagctggtaaaggaaaacccagagaaaataataatggccctatttga
agcagtccagacaattggcaaccccttgaggctcatatatcacctgtatggggtttactacaaagg
ctgggaagcaaaagaactatcagagagaacagcaggcaggaacctgttcaccttgataatgttcga
agccttcgaactactagggatggactctgaagggaagataaggaacctgtctgggaattatgtcct
ggatttgatctacagcctacataaacagataaatagaggcttgaaaaaaatagtcttggggtgggc
tcccgcaccatttagttgcgactggactcctagtgatgagagaattaggttacccacaaacaacta
tctaagagtagaaactaagtgtccatgtggctatgagatgaaagcactaaggaacgttggtggcag
tcttaccaaagtggaggagaaaggacctttctctgcaggaacaggcttggtagagggccggtcaa
ctatagagtcacaaagtactatgatgacaacctcaaagagataaaaccagttgctaaactagaagg
atttgtggatcactattacaaaggtgttacagcaaggatagattatggcagagggaaaatgctatt
agctactgataaatgggaggtggagcacggtgttgtcactaggttggcaaagagatataccggagt
tggattcaagggagcatacctgggtgatgaacccaaccaccgcgacctagtagaaagagactgtgc
aactataacaaaaaatacagtgcagtttttaaaaatgaagaaaggctgtgcatttacctatgactt
aaccctgtccaatttaaccaggttaattgaattggtacacaaaaataacctagaagagaaagacat
accagcagccacagtaacgacatggctggcttatacttttgtaaatgaagatattgggactataaa
accagtactaggagagagagtggtcaccgacccagtggtggatgttaacttacaaccagaagtaca
agtggatacatcagaggttgggatcactttagttggtagggcagccttaatgacgacaggtactac
acccgtagtcgaaaaaacagagcccaatgctgatggtggtccaagctccataaagattgggttgga
tgaaggaagatacccaggacctggactgcaagacgcaccttgaccgatgaaatacattctaggga
tgaaaggcccttttgttctagtctgggctcaaaaaattctatgtcaaatagagctaaaactgctag
aaacatcaacttatacaaggggaataaccccagggagattagagatctgatggcacaggggcgtat
gctagttgtggccttaaaggattttaaccctgagttgtctgaactagttgatttcaaggggacttt
cttagacagggaagccttggaagctctcagcctggggcggccaaagtccaagcaggtgaccacagc
cacagttagggagttattagagcaggaggtacaagttgagatccccagttggtttggagcaggtga
tccagtcttcttggaagtgactttgaagggtgacagatatcacttagtaggagatgtagatagagt
gaaagatcaagcgaaggagcttggggccacggaccagacaagaatagtgaaggaagtgggtgcaag
aacctataccatgaagctgtctagttggtttcttcaggcaacaaataaacagatgagcttgacccc
tttatttgaggagctattgctacgttgccccccctaaaataaagagcacataaaggcacatggcatc
agcttaccaactagcacagggaaactggggagcccctgactgtggagttcacctgggcaccatacc
tgccaggagggtaaaaatccacccatatgaagcttacctgaaactgaaggatttattggaagaaga
agaaaagaaaccaaagtgtagagacacagtaataagagaacacaacaagtggatcctcaaaaagt
gaggcaccagggtaatctcaatacaaagaaaatcctcaaccctggaaagctatcagaacagctaga
tagagaagggcataaaagaaacatttataacaatcagattggcaccataatgacggaagcaggaag
taggttggaaaaattaccagtcgtcagagcccaaactgacactaaaagcttccatgaggcaatcag
agataagatagacaagaatgaaaatcagagcccaggactgcatgataaattgttagagatctt
tcatacaatagcccaacccagcctaagacacacctacagtgacgtgacgtgggagcaacttgaggc
aggggttaatagaagggggctgctggcttctagaagaagaatgttggagaagtactggactc
agagaagcacctggtggaacaactgatcagagatttgaaaacaggaaggaagataagatattatga
gacagcaataccaaaaaatgagaagagagatgtcagtgatgattggcaatcaggggacttagtaga
tgagaagaaaccaagggtgattcaatacccctgaagctaaaacaagactagccatcactaaagtaat
gtacaactgggtgaaacagcagcccgtcgtgatcccagggtatgaagggaagaccccattatttaa
catttcaacaaggtgaggaaggaatgggatttgttcaatgaaccagtagctgtgagtttcgacac
taaggcttgggacacccaagtaactagtagagatctacggcttattggtgaaattcaaaaatatta
```

FIG.6C

```
gtatacgaggttaggcaagttctcgtatacatattggacactctaaaaataattaggcctaggggā
caaaaatcctccttagcgaaggccgaaaagaggctaaccatgcccttagtaggactagcaaaataa
gggggtagcaacagtggcgagttcgttggatggctgaagccctgagtacagggtagtcgtcagtg
gttcgacgctttggaggacaagcctcgagatgccacgtggacgagggcatgcccacagcacatctt
aacctggacaggggtcgttcaggtgaaaacggtttaaccaaccgctacgaatacagtctgatagga
tgctgcagaggcccactgtattgctactgaaaatctctgctgtacatggcacatggagttgatcac
aaatgaacttttatacaaaacatacaaacaaaaacccgctggagtggaggaaccagtatacgacca
agctggtaacccttgtttggagaaagaggagtgattcatccgcagtcaacgctaaaacttccaca
taaaagagggagcgtgaagtccccaccaatctggcttctttaccaaaagaggtgactgcaggtc
gggtaacagcaaggggcctgtgagtggaatctacttaaaaccagggccgttattctaccaagatta
taaaggacctgtctatcatagagccccattggagttttttgaggaggcgtctatgtgtgagacaac
taaaagaatagggagagtaactggtagtgacagcagattataccacatttacgtgtgtattgatgg
gtgcataatagtcaagagtgctacaaaagaccgccagaaagtactcaagtgggtccacaacaagct
aaactgcccctatgggtttcaagctgctccgacacaaagatgaaggggtggtgaggaagaagca
acaaaagccagataggttggaaaggggagaatgaagataacacctaaggagtcagagaaagacag
taagaccaagccgccagatgctacgatagtggtagatggagtcaagtatcaggtaaagaaaaaagg
aaaagtcaagagcaagaacacccaggacggcttataccacaacaaaaataaacctcaagagtcgcg
caagaaactagagaaagcccctattggcctgggcaataatagccctggtttttctttcaagtcacaat
gggagagaacataacgcaatggaacttacaagataatggaacggaaggcatacaacgagccatgtt
tcaaagaggagtgaatagaagtttacatgggatctggccagagaaaatctgtacaggtgttccttc
ccacctggccactgacacagaattgaaggcaattcatggtatgatggatgcaagtgagaagacaaa
ttatacgtgctgcagactccaacgccatgaatggaacaaacatggttggtgcaactggtacaacat
tgaaccttggatcctccttatgaataaaactcaggccaaccttactgagggtcagccactaaggga
gtgtgccgtcacatgccggtatgatcgagatagtgacctgaatgtagtaacacaagccagggatag
ccccacaccattaacaggttgcaagaaaggcaaaaacttttcctttgcaggcatattggtacaagg
gccttgcaactttgaaatagccgtaagtgatgtgctgttcaaagagcatgattgcactagtgtgat
tcaagacacagctcactacctcgtagacgggatgaccaactccctagagagtgccaggcaagggac
cgcgaaactaacaacttggctgggcaggcagcttgggatactaggaaagaaactggaaaacaagag
taagacatggtttggggcatatgcagcctctccctattgtgaggtagaacggaagcttggttacat
ctggtatacaaagaattgcactccagcctgtttgcctaggaatacaaagatcatcggccccggtag
gtttgacaccaatgccgaggatggtaaaatactgcatgagatgggggggtcacttgtcggaggtgct
actactctcagtggtagtgctgtccgatttcgctccagagacagccagtgtgatatacttgattct
tcatttctccatcccacaaggacacactgatatacaagattgtgacaaaaaccaactaaacctcac
cgtagaactcacaacagcagaagtaataccaggctcagtttggaacttgggtaaatatgtttgtgt
aagaccagattggtggccttatgagacagccacagtcctggtgattgaagaggtgggtcaagtaat
taaggttgtcttaagggcgttaaaagatctgacgcgcatttggaccgctgctacaaccactgcatt
cttggttttgtctggtgaaggtagtgagaggccaagtgttacaaggtatactgtggctgatgctcat
aacaggggcgcaagggtacccagactgcaaacccggcttttcatacgccatagccaaaaatgatga
gattggcccacttggagctacaggcctcaccactcagtggtacgaatactcggatgggatgcggct
gcaggactcagtagttgaagtttggtgtaaaaatggagagatcaaatatctaatcagatgcgggag
ggaagccaggtatctggctgttctacacacgagagccttgccgacatctgtagtatttgaaaaaat
ttttgatgggaaagaacaagaggacatagtagaaatggatgacaactttgaattcggtcttttgccc
gtgtgatgctagacccttgataaggggaaaatttaatacaacacttctaaatgggccagccttcca
gatggtttgccctataggatggacagggactgtaagctgtacactggccaataaggatacgttagc
cacaatcgttgtgagaacgtataagagggtcaggccttttccatataggcaggactgtgtcaccca
gaaaaccatcggggagaacctctacgactgtgccttaggaggggaattggacttgtgtgccggggga
tgcactacgatatgtagctgggcccgttgagtcttgtgagtggtgtggttacaagttttttaaaaag
tgagggtctgccgcatttcccaatcggcaaatgcaggctgaagaatgagagtggctatagacaagt
ggatgagacttcttgcaacagaaacggcgtggctatagtgccatctggcacggtcaaatgcaagat
aggggacacggtggtgcaagtcattgcaatggatgataaactagggcctatgccttgcaaaccaca
tgaaatcatatccagtgaggggccagtggaaaagacggcatgcaccttcaactacacaagaacatt
aaaaaacaagtactttgagcccagggataactattttcaacaatacatgttaaaggggagtacca
atattggtttgacctagagatcactgaccaccaccgagattacttcgctgagtccctgttggtgat
agtagttgcactcctgggtggcaggtacgtgctttggctgctggtcacatacatgatcttatcaga
acagatggcctcgggtgtccagtatggggcaggtgaaatagtgatgatgggcaacttgttaacaca
tgacagtgttgaagtggtgacatatttcttactactataccctactactaagagagggaaaaccaa
aaaatgggtcatacttatataccacatcatagtaatgcatcctctaaaatcggtgacggtgatatt
gctaatggttggggggatggcaaaggctgaaccaggtgcccaggggtacctagagcaggtagacct
```

FIG. 7A

```
tagttttacgatgattacgatcatcgtaataggtctggttatagctaggcgtgatcccactgtggt
gccactagtcactatagtcgcggcactgaagatcacaggactaggctttgggcccggagtggatgc
agctatggcagttctcaccttaaccctactgatgactagttatgtgacagactacttcaggtataa
aaggtggatacaatgtatcctcagcttagtagccggggtgttccttatccggaccctcaaacatct
aggtgaactcaaaacccctgagctgaccataccaaattggaggccactaaccttcatactattata
cctgacttcagcaacagttgttacaagatggaaaattgatatagctggcatattcctgcaaggggc
ccctatccttttgatgatcgccaccctatgggctgacttcttgactcttgttctgatcctacccac
ctacgaattagccaagctgtactacctaaagaacgtcaagactgacgtggagaagagttggctggg
ggggttagactacaggacaattgactctgtctatgatgtggatgaaagtggagaaggcgtgtacct
cttcccgtccagacagaagaaaaataagaatatcagcatactcttgcccctcatcagagctacgct
aataagttgtattagcagcaaatggcagatggtgtatatggcttacttaaccctggactttatgta
ctacatgcacagaaaggttattgaagagatatcagggagtaccaatgtgatgtctagagtgatagc
agcacttatagaattaaactggtccatggaagaagaagagagcaagggcttaaagaagttttttat
actatctggaaggttgaggaaccttataataaagcataaggttaggaaccagactgtggcaagctg
gtatggggaggaagaagtctacggcatgccaaaagtcgtaaccataataagggcctgcacgctaaa
caagaacaaacattgcataatatgcacagtatgtgaggctagaaagtggaagggaggcaactgccc
taaatgcggccgccacgggaagcccatcatttgtgggatgactctagcggattttgaagaaaggca
ctacaagagaattttataagggaaggtaactttgaaggacccttcaggcaggaatacaatggtt
tgtacaatacaccgctagggggcaattgttcctgagaaatttacccatattggcaaccaaagtaaa
aatgatcatggtaggcaacctaggagaggaaatcggtgatctagaacacctaggatggatcctaag
gggacctgccgtgtgcaagaaaataactgagcacgaaaaatgccatgtcaacatactggacaagct
gactgcgttttttggagttatgccaagagggactacaccaagggctccggtgagattcccaacagc
actactaaaggtaaggaggggattggaaaccggttgggcttacacgcatcaaggtggcataagctc
agtagaccatgtgaccgctggcaaggatctattggttttgtgacagtatgggtagaactagagtggt
ttgccaaagcaacaacaagttaactgatgagacagaatatggtgtcaagacggactccggatgtcc
agatggtgccagatgctatgtattaaacccagaggcagtaaatatatcagggtccaagggagctgt
cgtacacctccaaaaaacgggtggggaatttacatgtgttactgcatcaggtacaccggccttctt
cgacctgaaaaatttgaaaggatggtcgggtctacccatatttgaagcctccagcggcagagtggt
tggcagagtcaaagtgggaagaatgaggaatccaaacccacaaaattaatgagtggtatccaaac
tgtttctaaaaatacggccgatttaacagaaatggtcaagaagataaccagcatgaacagggggga
ctttaggcagataacccttgcaacaggggcagggaagaccactgagctcccaaaagcagtgataga
ggagataggacgacacaacgggtactagtgctcataccattaagagcagcagctgagtcagtcta
tcaatacatgagattgaaacacccaagtatctcctttaacctgagaataggggacatgaaagaagg
ggatatggcaaccgggatcacctacgcctcatatggatattttgccaaatgccacaaccaaagct
cagagcagcaatgatagagtattcatacatatttctggatgagtatcactgcgctactcctgagca
gttggctgttataggaaaaattcacagattttctgagagcataagagtggttgccatgactgccac
cccagcagggtcagtaaccacaacagggcaaaaacacccaatagaagaattcatagcccctgaggt
gatgaaaggggaggaccttggaagccagttccttgacatagcggggttaaagatccctgtagagga
gatgaagggtaacatgttggttttcgtgcccacgaggaacatggcagttgaagtagccaagaaact
aaaagccaagggctacaactcagggtattactacagtggggaagacccagctaacttgagagtggt
aacatcacagtccccatacgtcgtggtagccactaatgccatcgagtcaggggtaacgctgccaga
tttagatacagttgttgacacaggtctgaaatgtgagaagagggtgagggtgtcttccaaaatacc
ctttatagtaacaggccttaagagaatggctgtcactgtgggcgaacaggctcagcggagaggcag
ggtaggtagagtgaaacccggtaggtattatagaagtcaggaaacagcaaccgggtcaaaggacta
ccactatgacttgttacaggcacagaggtacgggatcgaagatgggatcaacgtaacaaagtcctt
tagggagatgaattatgactggagcctgtatgaggaagacagcttgctgataacccagctggagat
actgaacaatctactcatctctgaagatttaccagcagctgttaaaaacatcatggcaagaactga
tcacccagagcctatccagcttgcatataacagttatgaggtccaagtccctgtgctgttcccaaa
aataaggaatggggaggtcacagacacttacgagaactactcattcctaaatgcaaggaaactagg
ggaagacgtgcccgtgtacgtttatgccaccgaagatgaagatctggctgtggaccttctaggctt
ggactggccagacccagggaatcagcaagtagtggagactggaaggcactgaagcaagtggtagg
actgtcctctgccgaaaatgccttgctcatagccctatttgggtatgtaggataccaagccttgtc
aaaaagacacgtcccaatgatcacagacatatacactataagaagtcaaagactagaggacacaac
ccaccttcaatatgcgcccaatgccataagaactgaggggaaggagactgaactaaaggaattagc
agtgggtgacttggacaaaatcatgggttccatctcggactatgcatcagagggattgaatttcgt
aaggtcccaagcagaaagatgagatctgccccgcttcaaagaaaacgtggaagctgctaaagg
gtacgtccaaaagtttattgattctctcatagaaaataaagaaaccataatcagatatggcctgtg
gggaacacacacggcactctacaagagtattgccgcgagattgggtcatgaaactgcattcgctac
```

FIG. 7B

```
actagtgataaagtggctggccttcgggggtgagtcggtgtcagaccacatgagacaagcagctgt
cgacctggttgtttattatgtgatcaataagccctccttcccaggggattctgaaacccaacagga
aggaaggcgattcgtcgccagcctgttcatctccgctttggcaacctacacatacaaaacttggaa
ttacaacaacctctccaaggtagtagaaccagccttagcatacctcccctatgctaccaatgcact
aaaaatgtttaccccgaccagactggagagcgtagttatacttagtaccacaatatacaaaactta
cctctcaataaggaagggaaagagtgatggactgttgggtacagggatcagtgcagcaatggagat
tctatcacagaacccagtgtcggtaggtatatctgtcatgctgggggtggggcgattgccgcgca
caatgccattgagtctagtgaacaaaaaggaccctgttgatgaaagtgtttgtaaaaaacttcct
ggaccaggcggcaacagatgagctggtaaaggaaaacccagagaaaataataatggccctatttga
agcagtccagacaattggcaaccccttgaggctcatatatcacctgtatggggtttactacaaagg
ctgggaagcaaaagaactatcagagagaacagcaggcaggaacctgttcaccttgataatgttcga
agccttcgaactactagggatggactctgaagggaagataaggaacctgtctgggaattatgtcct
ggatttgatctacagcctacataaacagataaatagaggcttgaaaaaaatagtcttggggtgggc
tcccgcaccatttagttgcgactggactcctagtgatgagagaattaggttacccacaaacaacta
tctaagagtagaaactaagtgtccatgtggctatgagatgaaagcactaaggaacgttggtggcag
tcttaccaaagtggaggagaaaggacctttctctgcaggaacaggcttggtagagggccggtcaa
ctatagagtcacaaagtactatgatgacaacctcaaagagataaaaccagttgctaaactagaagg
atttgtggatcactattacaaaggtgttacagcaaggatagattatggcagagggaaaatgctatt
agctactgataaatggggaggtggagcacggtgttgtcactaggttggcaaagagatataccggagt
tggattcaagggagcatacctgggtgatgaacccaaccaccgcgacctagtagaaagagactgtgc
aactataacaaaaaatacagtgcagtttttaaaaatgaagaaaggctgtgcatttacctatgactt
aaccctgtccaatttaaccaggttaattgaattggtacacaaaaataacctagaagagaaagacat
accagcagccacagtaacgacatggctggcttatacttttgtaaatgaagatattgggactataaa
accagtactaggagagagagtggtcaccgacccagtggtggatgttaacttacaaccagaagtaca
agtggatacatcagaggttgggatcactttagttggtagggcagccttaatgacgacaggtactac
acccgtagtcgaaaaaacagagcccaatgctgatggtggtccaagctccataaagattgggttgga
tgaaggaagatacccaggacctggactgcaagaccgcaccttgaccgatgaaatacattctaggga
tgaaaggccctttgttctagtcctgggctcaaaaaattctatgtcaaatagagctaaaactgctag
aaacatcaacttatacaaggggaatacccaggagattagagatctgatggcacaggggcgtat
gctagttgtggccttaaaggattttaaccctgagttgtctgaactagttgatttcaaggggacttt
cttagacagggaagccttggaagctctcagcctggggcggccaaagtccaagcaggtgaccacagc
cacagttagggagttattagagcaggaggtacaagttgagatccccagttggtttggagcaggtga
tccagtcttcttggaagtgactttgaagggtgacagatatcacttagtaggagatgtagatagagt
gaaagatcaagcgaaggagcttggggccacggaccagacaagaatagtgaaggaagtgggtgcaag
aacctataccatgaagctgtctagttggtttcttcaggcaacaaataaacagatgagcttgacccc
tttatttgaggagctattgctacgttgccccccctaaaataaagagcaataaagggcacatggcatc
agcttaccaactagcacagggaaactgggagcccctttgactgtgagttcacctgtggcaccatacc
tgccaggagggtaaaaatccacccatatgaagcttacctgaaactgaaggatttattggaagaaga
agaaaagaaaccaaagtgtagagacacagtaataagagaacacaacaagtggatcctcaaaaaagt
gaggcaccagggtaatctcaatacaaagaaaatcctcaaccctggaaagctatcagaacagctaga
tagagaagggcataaaagaaacatttataacaatcagattggcaccataatgacggaagcaggaag
taggttggaaaaattaccagtcgtcagagcccaaactgacactaaaagcttccatgaggcaatcag
agataagatagacaagaatgaaaatcagcagagcccaggactgcatgataaattgttagagatctt
tcatacaatagcccaacccagcctaagacacacttacagtgacgtgacgtgggagcaacttgaggc
aggggttaatagaaaggggggctgctggctttctagagaagaagaatgttggagaagtactggactc
agagaagcacctggtggaacaactgatcagagatttgaaaacaggaaggaagataagatattatga
gacagcaataccaaaaaatgagaagagagatgtcagtgatgattggcaatcaggggacttagtaga
tgagaagaaccaagggtgattcaatacctgaagctaaaacaagactagccatcactaaagtaat
gtacaactgggtgaaacagcagcccgtcgtgatcccagggtatgaagggaagaccccattatttaa
cattttcaacaaggtgaggaaggaatgggatttgttcaatgaaccagtagctgtgagtttcgacac
taaggcttgggacacccaagtaactagtagagatctacggcttattggtgaaattcaaaaatatta
```

FIG.7C

```
ctacaggaaagagtggcacaaattcatcgataccattactgaccatatggtggaggtgcccgtcat
aacggcagatggtgaggtatacataagaaatggacaaaggggtagtggccagccagacacaagtgc
aggcaatagcatgctaaacgtgttaacaatgatgtatgccttctgtgaaagtacgggggttccata
caagagtttcaatagggttgcaaggatccatgtctgtggggatgacggcttcctaataacagagaa
ggggctgggattaaagtttgccaacaatgggatgcaaattctgcacgaagcaggcaagcctcaaaa
gataactgaggggaaagaatgaaagttgcctataggttcgaggacatagaattctgctctcatac
accagtccccgttaggtggtctgatacaccagcagttacatggccggcagagacactgccgttat
attatcaaagatggcaacaagattggattcaagtggagaaaggggtactatagcatatgaaaagc
agtggcctttagttttttgctgatgtactcctggaatcctcttgtgaggaggatctgtctactggt
cctttcacagcagccagagacaactccatcaacccagaccacttactattataaaggagacccaat
aggagcctacaaagatgtaataggtaagaatttgtgtgaattaaaaaggacgggttttgaaaaatt
ggccaatttaaacctaagcctgtccacgttaggaatctggtccaaacatacaagtaaaagaatcat
ccaagactgtgtaaccatcgggaaagaggaaggcaattggctggtcaatgccgacaggttgatatc
tagcaaaactggccatttgtacatacctgacaaaggttatacattacaagggaaacattatgaaca
acttcaactgcaggcaagaactagcccagtcacgggagtagggacggagagatataaactaggccc
tatagtaaacctgctgctgaggaggttgagagttctgcttatggcagctgtcggtgccagcagttg
aaataatgtatgtatatattgtatataaatctgtatttgtatatattatgtttaaatacgtagcca
gccccgattggggcgacactccaccatagatcactccctgtgaggaactactgtcttcacgca
gaaagcgtctagccatggcgttagtatgagtgtcgtgcagcctccaggaccccccctctcgggaga
gccatagtggtctgcggaaccggtgagtacaccggaattgccaggacgaccgggtcctttcttgga
tcaacccgctcaatgcctggagatttgggcgtgccccgcgagactgctagccgagtagtgttggg
tcgcgaaaggccttgtggtactacctgatagggtgcttgcgagtgctcgggaggtctcgtagacc
gtgcacttaattaataatttagttgagattagtagtgatatatagttatctacctaagctaaca
ctacactcaatgcacacagcacttagctgtatgagggtacacccgacgtccacggttggactagg
gaaaacgcttaacagcccc
```

SnaBI SITE AND PacI SITES
ClaI AND (PART OF) SmaI SITES USED TO INTRODUCE THE INSERT
NUCLEOTIDE EXCHANGES (C WAS CHANGED INTO T) IN THE HCV 5'NTR TO REMOVE TWO INTERNAL SmaI SITES
SnaBI SITE AND PacI SITES

FIG. 7D

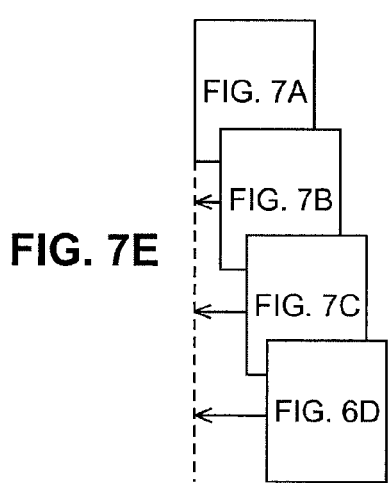

FIG. 7E

UGA-BOX UGA-BOX

TGAAATAATGTATGTATATATTGTATATAAATCTGTATTTGTATATATTATGTTTAAATTTAGTTGAGATTAGTAGTGAT
ATATAGTTATCTACCTCAAGCTAACACTACACTCAATGCACACAGCACTTTAGCTGTATGAGGGTACACCCG
ACGTCCACGGTTGGACTAGGGAAAACCCTTAACAGCCCC

FIG.8A

3'NTR OF BVDV-non-CP7

UGA-BOX UGA-BOX

TGAAATAATGTATGTATATATTGTATATAAATCTGTATTTGTATATATTATGTTTAAATACGTATTAATTAATTTAGTTGA
GATTAGTAGTGATATATAGTTATCTACCTCAAGCTAACACTACACTCAATGCACACAGCACTTTAGCTGTATGA
GGGTACACCCGACGTCCACGGTTGGACTAGGGAAAACCCTTAACAGCCCC

FIG. 8B

3'NTR OF BVDV-non-CP7 + CLONING SITE CHIMERA (SnaBI/PacI insert)

LEGEND
DOUBLE OVERSCORE = SNaBI
DOUBLE UNDERSCORE = PacI
UNDERSCORE = PSEUDO-STOP CODONS
ITALICS = *ADDITIONAL AND SPECIFICALLY CHANGED SEQUENCES*

UGA-BOX

UGA-BOX

TGAAATAATGTATGTATATATTGTATTTGTATATTATATTTGTTTAAATACGTAGCCAGCCCCGATT
GGGGGCGACACTCCACCATAGATCACTCCCCTGTGAGGAACTACTGTCTTCACGCAGAAAGCGTCTAGCC
ATGGCGTTAGTATGAGTGTCGTGCAGCCTCCAGGACCCCCCTCTCGGGAGAGCCATAGTGGTCTGCGGA
ACCGGTGAGTACACCGGAATTGCCAGGACGACCGGGTCCTTCTTGGATCAACCCGCTCAATGCCTGGAG
ATTTGGGCGTGCCCCCGCGAGACTAGTGTTGGGTCGCGAAAGGCCTTGTGGTACTGCCTG
ATAGGGTGCTTGCGAGTGCCCCGGAGGTCTCGTAGACCGTGCACTTAATTAATAATTAGTTGAGATTAGTA
GTGATATATAAGTTATCTACCTCAAGCTAACACTACACTCAATGCACACAGCACTTTAGCTGTATGAGGGTACA
CCCGACGTCCACGGTTGGACTAGGGAAAACCCTTAACAGCCC

5'NTRHCV INSERT

LEGEND
DOUBLE O

GROWTH CURVE

FIG. 10
GROWTH

BamHI SITE

GGATCCGCTGTCGGTGCCAGCAGTTGAAATAATGTATGTATATATTGTATATAAATCTGTATTGTATATTATGTTTA
AATACGTAGCCAGCCCCTATTGGGGCGACACTCCACCATAGATCACTCCCCTGTGAGGAACTACTGTCTTCACGCAGA
AAGCGGTCTAGCCATGGCGTTAGTATGAGTGTCGTGCAGCCTCCAGGACCCCCTCTCGGGAGAGCCATAGTGGTCTGCG
GAACCGGTGAGTACACCGGAATTGCCAGGACGACCGGGTCCTTTCTTGGATCAACCCGCTCAATGCCTGGAGATTTGGGC
GTGCCCCCGGAGACTGCTAGCCGAGTAGTGTTGGGTCGGAAAGGCCTTGTGGTACTGCCTGATAGGGTGCTTGCGAGT
GCCTCGGGAGGTCTCGTAGACCGTGCACCTTAATAATAATTAGTTGAGATTAGTAGTGATATATAGTTATCTACCTCA
AGCTAACACTACACTCAATGCACAGCACTTAGCTCTCTAGA — XBal SITE

FIG. 11A

CLONE 1, SEQUENCED: (FORWARD AND REVERSE SEQUENCES WERE IDENTICAL;
PCR FRAGMENT WAS CLONED BAMHI/XBAI)
*ITALICS* = HCV INSERT

G→T EXCHANGE IN HCV INSERT

C→T EXCHANGE IN HCV INSERT
CLONE 2, SEQUENCED: (FORWARD AND REVERSE SEQUENCES ARE IDENTICAL;
PCR FRAGMENT WAS CLONED BAMHI/XBAI)
*ITALICS* = HCV INSERT

BamHI SITE
GGATCCGCTGTGGTGCCAGCAGTGAAATAATGTATGTATATATTGTATATAAATCTGTATTGTATATT
ATGTTTAAATACGTAGCCAGCCCCGATTGGGGGCGACACTCCACCATAGATCACTCCCCTGTGAGGA
ACTACTGTCTTCACGCAGAAAGCGTCTAGCCATGGGCGTTAGTATGAGTGTCGTGCAGCCTCCAGGACC
CCCCCTCGGGAGAGCCATAGTGGTCTGCGGAACCGGTGAGTACACCGGAATTGCCAGGACGACC
GGGTCCTTTCTTGGATCAACCCGCTCAATGCCTGGAGATTTGGGCGTGCCCCCGCGAGACTGCTAGC
CGAGTAGTGTTGGGTCGCGGAAAGGCCTTGTGGTACTGCCTGATAGGGTGCTTGCGAGTGCCTCGGGA
GGTCTCGTAGACCGTGCACCTTAATAATTAGTTGAGATTAGTAGTGATATAGTTATCTACCTCAA
GC*AACACTACACTCAATGCACACAGCACTTTAGCTG*(*TCTAGA*) ← XBal SITE

FIG. 11C

T→C EXCHANGE IN BVDV SEQUENCE
CLONE 3, SEQUENCED: (FORWARD AND REVERSE S

BamHI SITE
GGATCCGCTGTCGGTGCCAGCAGTTGAAATAATGTATGTATATTGTATATAAATCTGTATTTGTATATT
ATGTTTAAATACGTAGCCAGCCCCCGATTGGGGGGGACACTCCACCATAGATCACTCCCTGTGAGGA
ACTACTGTCTTCACGCAGAAAGCGTCTAGCCATGGCGTTAGTATGAGTGTCGTGCAGCCTCCAGGACC
CCCCCTCTCGGGAGAGCCATAGTGGTCTGCGAACCGGTGAGTACACCGGAATTGCCAGGACGACC
GGGTCCTTTCTTGGATCAACCCGCTCAATGCCTGGAGATTTGGGCGTGCCCCCGCGAGACTGCTAGC
CGAGTAGTGTTGGGTCGCGAAAGGCCTTGTGGTACTGCCTGATAGGGTGCTTGCGAGTGCCTCGGGA
GGTCTCGTAGACCGTGCACCTTAATAATTAGTTGAGATTAGTAGTGATATAGTTATCTACCTCAA
GCTAACACTACACTCAATGCACACAGCACTTTAGCTG(TCTAGA)
                                         XBaI SITE

FIG. 11D

NO CHANGES
CLONE 4, SEQUENCED: (FORWARD AND REVERSE SEQUENCES ARE IDENTICAL;
PCR FRAGMENT WAS CLONED BamHI/XbaI)
*ITALICS* = HCV INSERT

BamHI SITE

GGATCCGCTGTCG_TGCCAGCAGTTGAAATAATGTATGTATATATTGTATATAAATCTGTATTTGTATATT
ATGTTTAAATACGTAGCCAGCCCCGATTGGGGCGACACTCCACCATAGATCACTCCCTGTGAGGA
ACTACTGTCTTCACGCAGAAAGCGTCTAGCCAGAAGCGTCTAGCCATGGCGTTAGTATGAGTGTCGTGCAGCCTCCAGGACC
CCCCCTCTCGGGAGAGCCATAGTGGTCTGCGGAACCGGTGAGTACACCGGAATTGCCAGGACGACC
GGGTCCTTTCTTGGATCAACCCGCTCAATGCCTGGAGATTTGGGCGTGCCCCCGCGAGACTGCTAGC
CGAGTAGTGTTGGGTCGGAAAGGCCTTGTGTACTGCCTGATAGGGTGCTTGCGAGTGCCTCGGGA
GGTCTCGTAGACCGTGCACCTTAATTAATAATTAGTTGAGATTAGTAGTGATATAGTTATCTACCTCAA
GCTAACACTACACTCAATGCACACAGCACTTAGCTG*TCTAGA* — XBaI SITE

FIG. 11E

G DELETED IN BVDV SEQUENCE
CLONE

FIG. 12

HCV VS. BVDV-NON-CP7-HCV 5'NTR CHIMERA
AS CALIBRATORS

HCV
$y = -3.8196X + 44.319$
$R^2 = 0.9911$

BVDV-HCV CHIMERA
$y = -3.8043X + 43.98$
$R^2 = 0.9772$

Legend:
- ◇ HCV
- ○ BVDV-HCV CHIMERA
- – ·· – ·· – LINEAR HCV
- – – – – – LINEAR BVDV-HCV CHIMERA Axes: Ct vs. Log concentration (IU/ml)

FIG. 13

WNV ASSAY WITH A BVDV-NON-CP7-HCV 5'NTR CHIMERA QS

REPLICATION STABLE AND RNASE RESISTANT CHIMERAS OF *PESTIVIRUS* WITH INSERTION IN 3' NONTRANSLATED REGION (3'NTR)

CROSS-REFERENCE TO RELATED APPLICATIONS

This application is a continuation of U.S. application Ser. No. 12/277,282, filed Nov. 24, 2008 now abandoned, which disclosures are herein incorporated by reference in their entirety.

BACKGROUND OF THE INVENTION

An RNA virus has RNA (ribonucleic acid) as its genetic material, and infects host cells from bacteria, plants or animals, such as livestock and humans. The major criteria of how RNA viruses are classified are the sense and organization of the viral genome that determines the mode of viral RNA replication, including whether the viral RNA genome has positive (message) or negative sense, whether it is single or double stranded, and whether it is non-segmented or segmented.

Regulatory agencies often require that assays for detection of nucleic acids utilize quality control materials, including standards, calibrators and controls (Molecular Diagnostic Methods for Infectious Diseases; Approved Guideline, 2nd ed., Clinical and Laboratory Standards Institute, vol 26 (8), 2006). Quality control materials insure optimum performance and reliability of test results, including nucleic acid test (NAT) assays. Laboratories are required to demonstrate that assays for detection of viral RNA function properly as intended and are not affected by inhibition or other forms of interference. Controls for qualitative assays provide assurance of true negative and positive results while minimizing the chance for false positive and false negative results. In quantitative assays controls help ensuring accuracy of results. Validation and verification panels are frequently used to check if diagnostic assays or systems (hardware, software and reagents) perform as intended. A panel consists of more than one vial of material useful to improve or check, verify or validate the performance or quality of a diagnostic assay. A panel can, for example, be made from a dilution series that contains different concentrations of an analyte. Calibrators are used to calibrate and recalibrate a diagnostic system, usually after an element of the diagnostic system was changed (e.g. new lot of reagents) or after a predetermined time interval.

Ideally, the quality control material is as similar as possible in structure and morphology to the target analyte so both behave the same when tested. If NAT controls, calibrators or standards behave like a patient sample on different diagnostic systems, they are considered "commutable" amongst these systems. Commutability is a key property of quality control materials that is especially important for calibrators and standards. The quality control material, however, should still be able to generate a signal that is distinguishable from that of the target analyte. Typically, viral RNA assays may have external run controls (positive or negative control) (EC), various types of internal controls (IC), or internal quantification or quantitation standards (QS), as well as calibrators. Internal and external control concepts are further described in CLSI Guideline MM3-A2 and U.S. Pat. Nos. 7,183,084 B2 and 7,192,745.

While PCR and other NAT techniques can test both DNA and RNA, there are technical challenges especially with quality control for RNA assays: 1) RNA is generally more labile than DNA, presenting additional technical difficulties for analytical RNA assays as compared to DNA assays. Naked RNA is sensitive to degradation through RNases, ubiquitously present RNA digesting enzymes. RNases can be found almost everywhere in the environment, however, they are especially prevalent in animal cells and fluids. In order to fully quality control all steps of an RNA assay, it is best to protect the RNA of the quality control material from potential degradation. An intact naturally occurring RNA virus, which does protect its RNA inside the virus, may be used as a calibrator or external positive run control, as long as its RNA sequence contains the primer and probe regions of the target virus. It may not be combined, however, with the test sample to be used as an internal control or quantitative standard, because it would cause a false positive signal. 2) It is desirable that a RNA quality control material should be capable of monitoring the entire diagnostic process and serve as a "full process control", including nucleic acid isolation, reverse transcription, amplification and detection. 3) The use of materials potentially infectious for humans is not desirable in a diagnostic kit due to safety concerns and shipping regulations. 4) Internal Quality Standards (IQS) like Internal Controls (IC) and internal Quantification or Quantitation standards (QS) materials often can not be obtained from naturally occurring sources. The term "QS" is used in the literature as abbreviation for Quantification Standard, Quantitation Standard, internal Quantification Standard or internal Quantitation Standard, essentially all describing the same type of standard (see Clinical and Laboratory Standards Institute, CLSI Guideline MM3-A2 for details of QS use). This is particularly true for any IQS used as a "competitive" control, which utilizes the same primer sequence as the target RNA, but can be distinguished by a probe sequence different from the target sequence. Such IQS materials usually need to be artificially created. 5) RNA itself is not as amenable to recombinant genetic engineering as DNA and usually requires a DNA intermediate. While it is known to transcribe RNA sequences from recombinant DNA sequences, it is difficult to package and protect these RNA transcript sequences from degradation by RNases.

One approach to solve the issues of RNA instability for quality control materials for RNA viral testing has been the use of "armored RNA," recombinant RNA packaged in MS2 bacteriophage (e.g., see U.S. Pat. Nos. 5,677,124, and 7,033, 749). Armored RNA has a single strand of MS2 RNA containing a recombinant heterologous RNA encapsidated by MS2 bacteriophage proteins to form a pseudo-viral particle.

Armored RNA offers several advantages over naked RNA as a quality control material: 1) It is stable, non-infectious and RNase resistant, and 2) It is useful both as a positive control, an internal control (IC) and quantification standard (QS), and an extraction control. Armored RNA has been useful for the quantification of RNA viruses such as HIV and HCV from human blood. Armored RNA also is utilized as a high titer HCV surrogate material, since it is not possible to grow all different HCV subtypes in culture.

Armored RNA has several disadvantages for use as a quality control material in analytical assays. Ideally, quality control materials should react like the tested analyte in an assay in order to monitor meaningfully all aspects of the procedure. The structure and infected host for armored RNA, however, is very different from that of many animal RNA viruses, e.g. HCV or HIV. A bacteriophage, which infects bacteria, is genetically distant to animal or other eukaryotic viruses. MS2 bacteriophage is not detergent sensitive, because it has a protein coat instead of a lipid bilayer. Many diagnostically relevant enveloped viruses causing harm to humans and livestock (e.g. HIV, *Pestiviruses*, West Nile Virus (WNV) or HCV) possess detergent sensitive outer envelopes. Because the armored RNA protein coat is very different biochemically from the lipid envelope of these animal viruses, the MS2 bacteriophage particles may behave differently from the targeted animal viral particles in analytical assays. It is conceivable that an Armored RNA QS used to monitor a reaction would fail to indicate that HIV had been destroyed by detergent which contaminated a blood donor test sample. In this case the result could be a false negative blood screening result for HIV resulting in the transfusion of HIV positive CD4 blood cells to several recipients. Armored RNA has never been shown to be commutable, meaning that it behaves like the virus it is supposed to mimic as a quality control. 4) Recovery efficiency of RNA with the most commonly used silica based sample preparation methods is to a certain degree dependent on the length of the RNA. Most human RNA viruses, such as HCV, HIV or WNV, have about three times longer RNA genomes than armored RNA.

Although armored RNA has been useful as a control in analytical assays, it would be preferable to have a quality control material for in vitro diagnostic assays that more closely resembles the targeted animal or human RNA virus than a bacteriophage derived pseudo-viral particle. It would be preferable to have quality control material that is structurally and morphologically similar to the target RNA virus and thus behaves more like e.g. HCV, West Nile Virus (WNV) or HIV viruses. Finally, it would be preferable to have the option of being able to insert heterologous sequences into replication competent viruses.

Chimeric RNA viruses that are similar in structure to the virus being tested would be an ideal quality control material for RNA assays if they were genetically stable and could be grown in culture. In this method, a region of a targeted virus is inserted into the genome of another virus to form a chimeric virus. By testing for the inserted target region, the chimeric virus can function as a quality control material.

In designing a stable viral chimera, it is important to identify a point of insertion in the compact viral genome that does not interfere with the viability of the virus. It is known that the choice of the target region to be inserted, as well as the site for the insertion can dramatically affect chimeric RNA viral functions, especially RNA replication, packaging of the RNA genome, virion stability, and virus infectivity. If the chimeric viral RNA replicates improperly, spontaneous sequence changes, such as deletions or frameshifts, may occur during replication in the RNA sequence of the virus chimera to form useless sequence revertants or pseudo-revertants. The ultimate genomic sequence of the revertant virus is unpredictable and may exclude part or parts of the applied insert. Unstable chimeric RNA virus, therefore, is usually not useful as a quality control material in an analytical RNA assay.

Examples of positive-strand ssRNA chimeras are known that utilize the 5' nontranslated region (5'NTR) and the open reading frame (ORF). Martin disclosed chimeric GBV-B/HCV (U.S. Pat. No. 7,141,405; US2006/0160067; US2006/0105365). Ilya et al. disclosed chimeric Eastern Equine Encephalitis virus and Sindbis virus (WO 2007/002793). Hong et al. describe HCV/BVDV chimeric constructs where the $N^{pro}$ protease gene is replaced (U.S. Pat. No. 6,326,137). Nam et al. disclosed HCV/BVDV constructs involving exchange of structural genes, especially E1, E2 or C. (U.S. Pat. No. 7,009,044). Rice and Kolykhalov (U.S. Pat. No. 6,127,116) disclosed that functional HCV clones can be used for the assay of HCV by constructing chimeric viruses using components of the IRES, proteases, RNA helicase, polymerase, or 3'NTR to create chimeric derivatives of BVDV whose productive replication is dependent on one or more of these HCV elements. None of these examples, however, disclosed stable *Pestivirus* RNA chimeras with insertion within the 3'NTR.

While the general concept of chimeric RNA viral constructs is known, no functional examples are provided in the prior art that utilize intentional insertion of heterologous sequences within the 3'NTR of a *Pestivirus* to obtain a chimeric virus that is replication stable and forms infectious viral particles at titers comparable to that of a wild type virus.

Rice et al. disclosed a concept of constructing BVDV chimeras with inserted sequences from HCV (WO 99/55366; see also Frolov et al., 1998, RNA 4, 1418-1435). No data were given, however, that showed their chimeric constructs involving the 3'NTR were genetically stable. In Example 5 (WO 99/55366), Rice et al described a tandem 3'NTR construct where an HCV 3'NTR insert was placed downstream of the ORF and immediately followed by the intact 3'NTR of BVDV (FIG. 19). Rice et al. reported this 3'NTR HCV-BVDV tandem construct replicated poorly and revertants formed, which showed deletions when sequenced (FIG. 20). Significantly, Rice et al placed the HCV 3'NTR insert precisely downstream of the stop codon of the ORF of BVDV, not within the 3'NTR of BVDV. Rice et al., therefore, did not construct a replication competent BVDV chimera with insertion within the 3'NTR that was genetically stable and could be grown in culture.

Recently, progress has been made in the development of (copy) cDNA clones of full-length BVDV genomes. These so-called "infectious BVDV cDNA clones" allow the in vitro transcription of infectious BVDV RNA genomes (Meyers, et al., J. Virology, 1996, 70: 8606-8613, erratum in J. Virol. 1997, 7 (2): 1735; Vassilev, et al., J. Virology, 1997, 71: 471-478; U.S. Pat. No. 6,001,613).

There is a need in RNA viral testing of Flaviviridae and other RNA viruses to have viral quality control material that is similar in genomic composition and virion composition to the RNA virus being tested.

There is a need in nucleic acid test assays (NAT) for QC materials, standards, calibrators, reference materials, validation and verification material that behave like the target material.

There is a need for such RNA viral quality control materials to be stable in sequence, to be replication stable and to be resistant to degradation by RNases.

It would be useful to have a known region within the 3'NTR of a Flaviviridae/*Pestivirus* virus defined that allows the stable insertion of heterologous sequences.

SUMMARY OF THE INVENTION

This invention provides the identification of the location of a region within the 3'NTR of the genomic RNA of a Flaviviridae member, the *Pestivirus* BVDV, where a heterologous RNA sequence can be inserted to generate stable viral RNA chimeras and stable chimeric virus particles. Similar to the wild-type BVDV virus particles, the chimeric virus particles with a heterologous insertion in the 3'NTR of the viral RNA genome are sequence stable, replication-competent, resistant to RNases, and infectious.

Useful and stable *Pestivirus* RNA chimeras are constructed from an understanding of the viral RNA genome to identify areas within the 3'NTR for stable insertion of heterologous sequences. In this invention, a defined area within the 3'NTR of the genomic RNA of a Flaviviridae member, the *Pestivirus* BVDV, is used to create a stable chimeric virus, which was demonstrated to be useful in an analytical viral assay. A stable chimeric *Pestivirus* can be utilized similar to the ways in which armored RNA is used in diagnostic and analytical assays. Current armored RNA applications are known, and also have been described in U.S. Pat. Nos. 5,677,124, and 7,033,749 and their dependent patents. Unlike armored RNA, however, the chimeric *Pestivirus* is viral quality control material that is similar in genomic composition and virion composition to the RNA virus being tested.

In this invention we used our current understanding of the detailed "signal" function of the different elements of the 3'NTR of *Pestivirus* genomic RNA to generate a stable replication competent BVDV chimera containing a heterologous sequence within the 3'NTR of the genomic RNA. In a preferred embodiment, the heterologous insertion is made within the 3' NTR variable region (3'V). Most preferably, the insertion is made in a defined sequence region located downstream of the UGA$_{pos.cons.}$ box (Isken et al., 2004). This insertion site is located downstream of the region that was experimentally shown with the BVDV DI9c replicon RNA (Isken et al., 2004) to form the SL$_{stop}$(SLIII) structure and that is proposed by RNA folding programs such as mfold 3-1 (http://www.bioinfo.rpi.edu/~zukerm/export/) to form SL$_{stop}$ (SLIII) with the genomic RNA of all other *Pestivirus* members. The insertion site is located upstream of the region that was experimentally shown with the BVDV DI9c replicon RNA to form the SLII structure and that is proposed by the RNA folding program mfold 3-1 to fold SLII with the genomic RNA of all other *Pestivirus* members. (Grassmann, C., Yu, H., Isken, O., and Behrens, S.-E. (2005). Hepatitis C virus and the related bovine viral diarrhea virus considerably differ in the functional organization of the 5' non-translated region: implications for the viral life cycle. Virology 333: 349-366; Isken, O., Grassmann, C. W., Sarisky, R. T., Kann, M., Zhang, S., Grosse, F., Kao, P. N., and Behrens, S.-E. (2003). Members of the NF90/NFAR protein group are involved in the life cycle of a positive-strand RNA virus. EMBO J. 22: 5655-5665; Isken, O., Grassmann, C. W., Yu, H., and Behrens, S.-E. (2004). Complex signals in the genomic 3' non-translated region of bovine viral diarrhea virus coordinate translation and replication of the viral RNA. RNA 10: 1637-52; Isken, O., Baroth, M., Grassmann, C. W., Weinlich, S., Ostareck, D. H., Ostareck-Lederer, A. and Behrens, S.-E. (2007). Nuclear factors are involved in hepatitis C virus RNA replication. RNA 13: 1675-1692.)

The location of the UGA$_{pos.cons.}$ box is conserved in the genomes of all *Pestivirus*3'NTRs (Becher, et al., J. Virology, 1998, 72 (6): 5165-73; Isken, et al., 2003; Isken, et al., 2004). Given the general structural alignment of the UGA$_{pos.cons.}$ box, the stem-loop structures SL$_{stop}$ (SLIII), SLII and SLI, and other structural elements within the 3'NTR of *Pestivirus*, the construction of chimeric virus is not only applicable to the *Pestivirus* BVDV but to all *Pestivirus* embers.

This invention provides RNA viral chimeras with insertions in the 3'NTR as quality control material, including use as controls, standards and calibrators in RNA viral analytical NAT assays.

BRIEF DESCRIPTION OF THE FIGURES AND TABLES

FIG. 1 shows a comparison of the genomic organization of *Hepacivirus* HCV and *Pestivirus* BVDV viruses. The 5' NTR (IRES) and 3'NTRs are indicated as single lines, and the open reading frame (ORF) for the viral polyprotein is schematized as boxes, with the different viral proteins indicated within the boxes. The enzymatic activities that proteolytically mature the viral polyprotein are designated as autoprotease (A); cellular signalase (closed oval), and viral protease (arrow).

FIG. 2 is a schematic diagram of the secondary structures of the HCV and BVDV NTRs flanking the ORF, which is shown as a box. The area of the HCV 5'NTR is enclosed with a long-dashed line, and the area of the BVDV 3'NTR is indicated with a dotted line. An arrow indicates that the HCV 5'NTR was inserted within the region of the 3'NTR of BVDV.

FIG. 3 shows a schematic of the secondary structure of the 3'NTR of *Pestivirus* BVDV (SEQ ID NO: 19) and of proposed functions of this region during viral replication. The sequence (taken from the BVDV replicon construct D19c; Behrens et al., 1998; Behrens, S.-E., Grassmann, C.W., Thiel, H. -J., Meyers, G., and Tautz, N. 1998 Characterization of an autonomous RNA replicon of a *Pestivirus*. J. Virol. 72: 2364-2372) reads 5' to 3' in direction. The UGA translational stop codon and the so-called "pseudo-stop codons" are boxed with a thin line, and the UGA boxes found in this isolate are boxed with a heavy line. The stem-loop structures, which were determined experimentally, are labeled SLstop, SLII and SLI (Isken et al., 2004, Yu et al., 1999; Yu, H., Grassmann, C. W., and Behrens, S. -E. 1999 Sequence and structural elements at the 3' terminus of the bovine viral diarrhea virus: functional role during RNA replication. J. Virol. 73: 3638-3648). The 3' variable (V) region and the 3' constant (C) region are indicated; the border is indicated by an arrow (according to sequence alignments by Deng and Brock, 1993 (Deng R, Brock KV. Nucleic Acids Res. 1993 Apr 25:21(8):1949-57). A translating ribosome is indicated by a double structure at the 5' end of the 3'NTR, indicating that ribosomes terminate at the position of the translation termination codon. The following double line indicates that the 3'V region is involved in efficient termination of translation at the translational stop codon (Isken et al., 2004). The NFAR protein binding site is indicated by a group of circles, and the site where the viral replication complex presumably forms is indicated by a large oval (Isken et al., 2004. The heterologous RNA sequence may be inserted within the 3'NTR. A preferred site of insertion of the HCV 5'NTR within the 3'NTR is indicated by a thick arrow.

FIG. 4 is a schematic diagram of the 3'NTR of *Pestivirus* BVDV (SEQ ID NO: 19). As in FIG. 3, the sequence and secondary structure information are derived from the BVDV D19c replicon (Behrens et al., 1998; Yu et al., 1999). The 3' variable [3'V (1-90 nt)] and the 3' constant [3'C regions (91-192 nt)] are indicated. The stem-loop structures: SLSTOP, SLII and SLI are labeled. The UGA translational stop codon and the pseudo-stop codons are boxed. The UGA box motifs within the 3'V are shown boxed with a heavy line, including the 5'UGA box, the UGApos.cons. box and the 3'UGA-like box (Isken et al., 2003; Isken et al., 2004). A preferred site of insertion of the HCV 5'NTR within the 3'NTR is indicated by a thick arrow.

FIG. 5A shows a schematic sequence alignment of the 3'NTRs of various *Pestivirus*strains, including BDV X818 (SEQ ID NO: 13), CSFV C-strain (SEQ ID NO: 14), CSFV Alfort-T (SEQ ID NO: 15), BVDV type 1 NADL (SEQ ID NO: 16), BVDV type 1 Osloss (SEQ ID NO: 17) and BVDV type 2 890 (SEQ ID NO: 18) . For all these *Pestivirus* strains, the positions that form the stem-loop structures SLstop (SLIII) and SLII are indicated. Nucleotides that are 100% conserved between the different strains are indicated with an asterisk (*). The UGApos.cons. box is boxed. A thin arrow indicates a preferred site between the SLstop (SLIII) and SLII stem-loop structures for the insertion of heterologous RNA sequence within the 3'NTR. A thick arrow indicates the border between the 3'V and 3'C regions within the 3'NTRs (Deng and Brock, 1993). FIG. 5B shows a sequence alignment of UGA box sequences in the 3'NTRs of various *Pestivirus* strains (SEQ ID NOS: 20-31)(Isken et al., 2003). 100% conserved nucleotides are boxed. The consensus sequence for the twelve nucleotides from this sequence alignment of the UGA boxes is indicated.

FIG. 7 shows the cDNA sequence of the BVDV-non-CP7+ cloning site chimera (SEQ ID NO: 4) with the restriction endonuclease sites for ClaI, part of SmaI, SnaBI and PacI indicated.

FIG. 8 shows the sequence compositions of the 3'NTR for: (A)*Pestivirus* BVDV-non-CP7(SEQ ID NO: 5), (B) the BVDV-non-CP7+cloning site chimera (SEQ ID NO: 6), and (C) BVDV-non-CP7-HCV 5'NTR chimera (SEQ ID NO: 7). Provided are the sequences of the 3' non-translated regions (3'NTRs) of: the BVDV non-CP7 cDNA (starting material; wild type) (FIG. 8A), the BVDV non-CP7 cDNA+cloning site chimera (FIG. 8B), which is a recombinant cDNA containing the inserted SnaBI and PacI restriction sites at pos 12134-12148), and) the recombinant cDNA of the *Pestivirus* BVDV-non-CP7-HCV 5'NTR chimera (FIG. 8C) containing the inserted HCV 5'NTR (HCV sequence subtype Ib (Lohmann et al., Science 1999 Jul 2: 285 (5424): 110-3) plus SnaBI and PacI sites inserted at pos. 12134-12492. Note that two SmaI sites in the HCV insert were inactivated by two site-directed nucleotide exchanges (c to t exchanges at positions 12269 and 12456 of the BVDV-non-CP7-HCV 5'NTR chimera sequence; see SEQ ID NO: 2 for the cDNA of HCV 5'NTR). This was done to enable linearization of the chimeric BVDV cDNA construct by a single SmaI site at the 3'-end of the cDNA for run-off in vitro transcription by SP6 RNA polymerase. The translation stop codon (tga) is boxed; pseudo-stop codons are underlined; restriction endonuclease sites are bracketed, the restriction endonuclease sites SnaBI (tacgta) and PacI (ttaattaa) are indicated; the UGA-box motif sequences are shown in bold and boxed with dashed lines; the 5'NTR HCV insert is shown in a large boxed region. Sites that were added or modified, such as the taa site following the Pac site, are indicated in italics.

Figure 9:
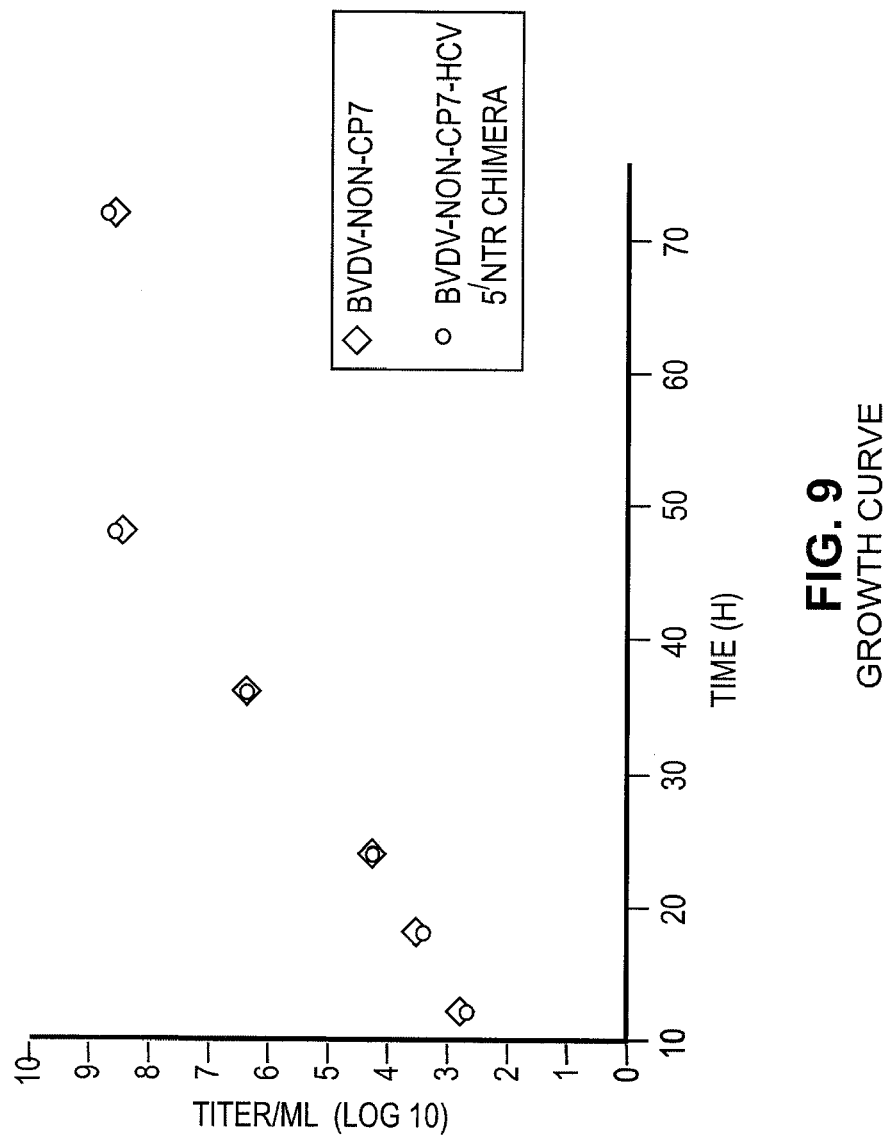

FIG. 9 shows growth curves obtained for the BVDV-non-CP7 (open diamonds) and the BVDV-non-CP7-HCV 5'NTR chimera (open circles).

Figure 10:
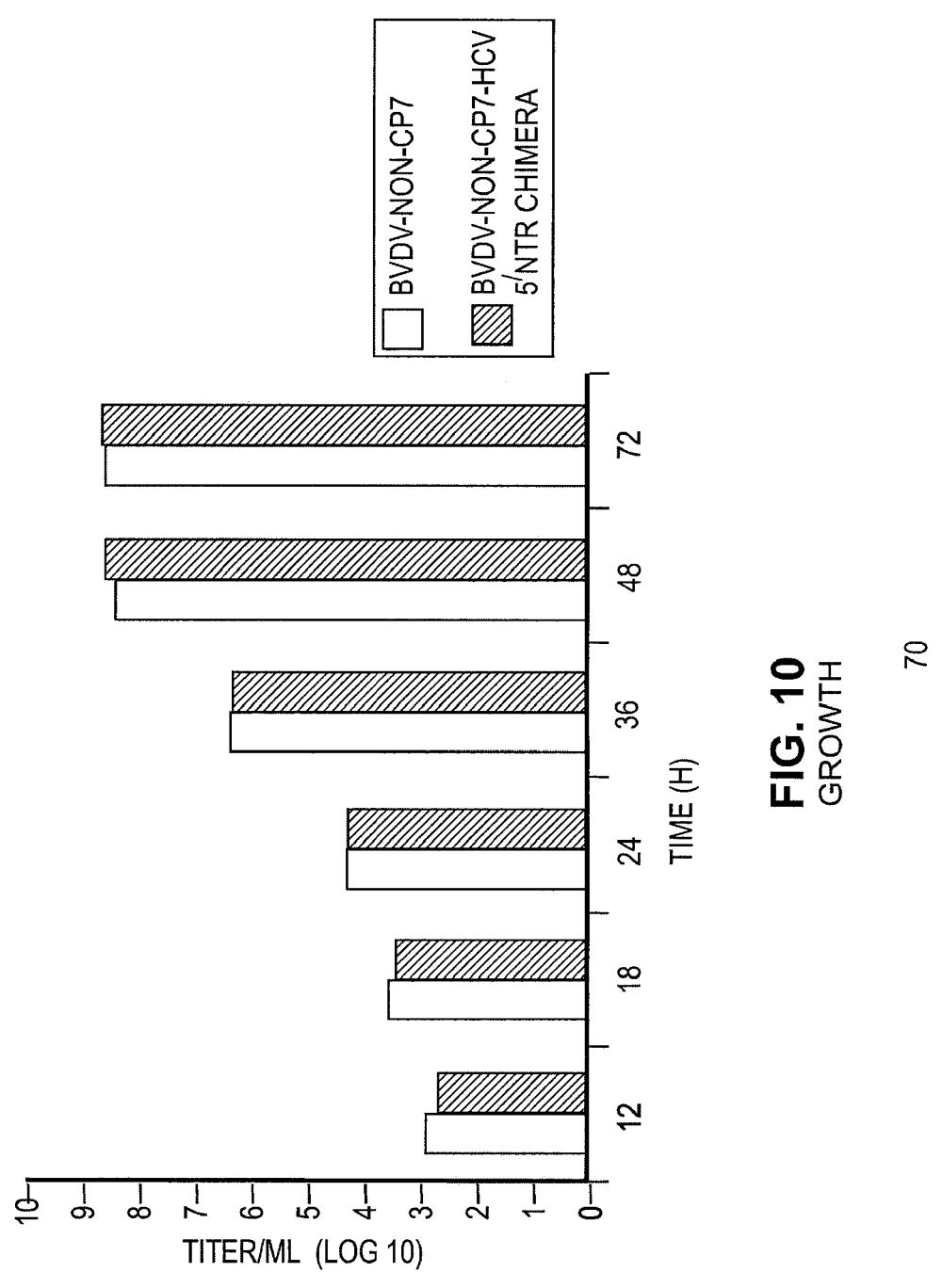

FIG. 10 shows growth curve data in bar graph format for the BVDV-non-CP7 (open bar) and the BVDV-nonCP7-HCV-5'NTR chimera (cross-hatched bar).

Figure 11B:
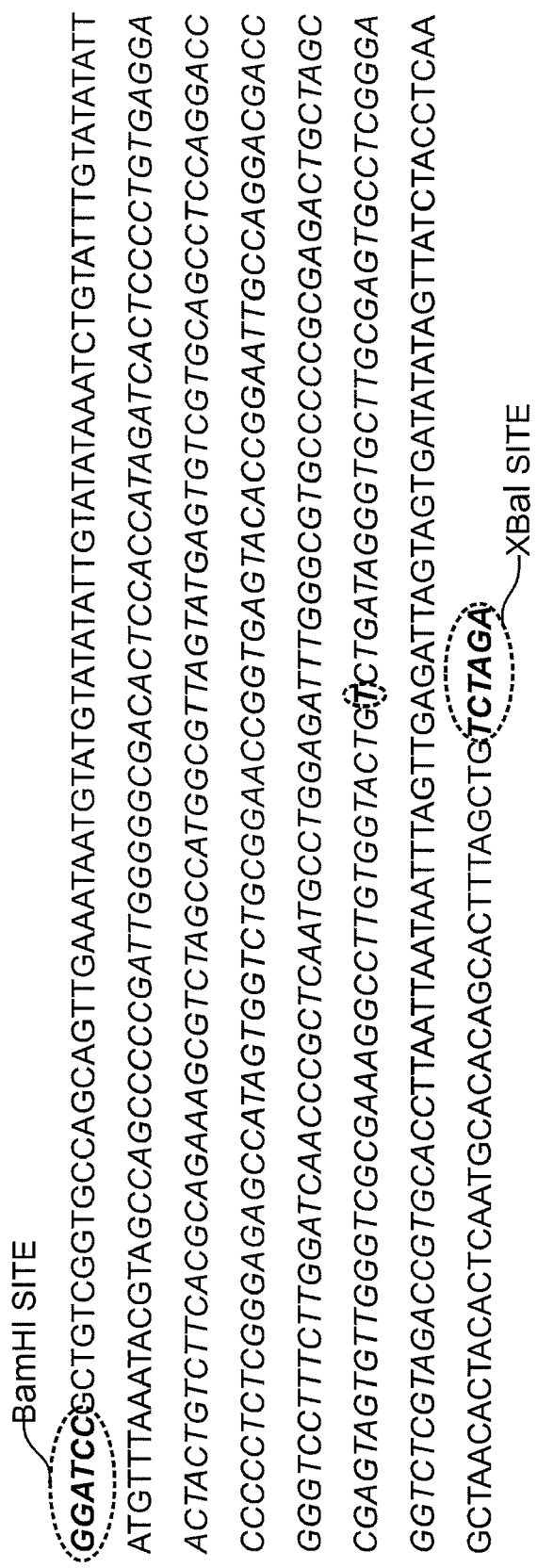

FIG. 11 shows sequence information obtained for five viral isolates following seven passages of re-infections. Following RT-PCR of total viral RNA isolated from infected cells after seven (7) passages of re-infections, the PCR fragment was cloned using BamHI and XbaI. Five clones were sequenced. The details of the sequence changes observed in these five clones are shown in FIGS. 11A-11E (SEQ ID NOS: 8-12, respectively).

FIG. 12 shows the signals obtained for the use of *Pestivirus* BVDV-non-CP7-HCV 5'NTR chimera and a known HCV control as a calibrator. The measured Ct values for both calibration panels were plotted against the log of the expected international units (IU). The equations of the linear regression fit lines were equivalent within the measurement error: y=−3.80 x+44.0 for HCV-BVDV; y=−3.82x+44.3 for Opti-Quant HCV.

Figure 13:
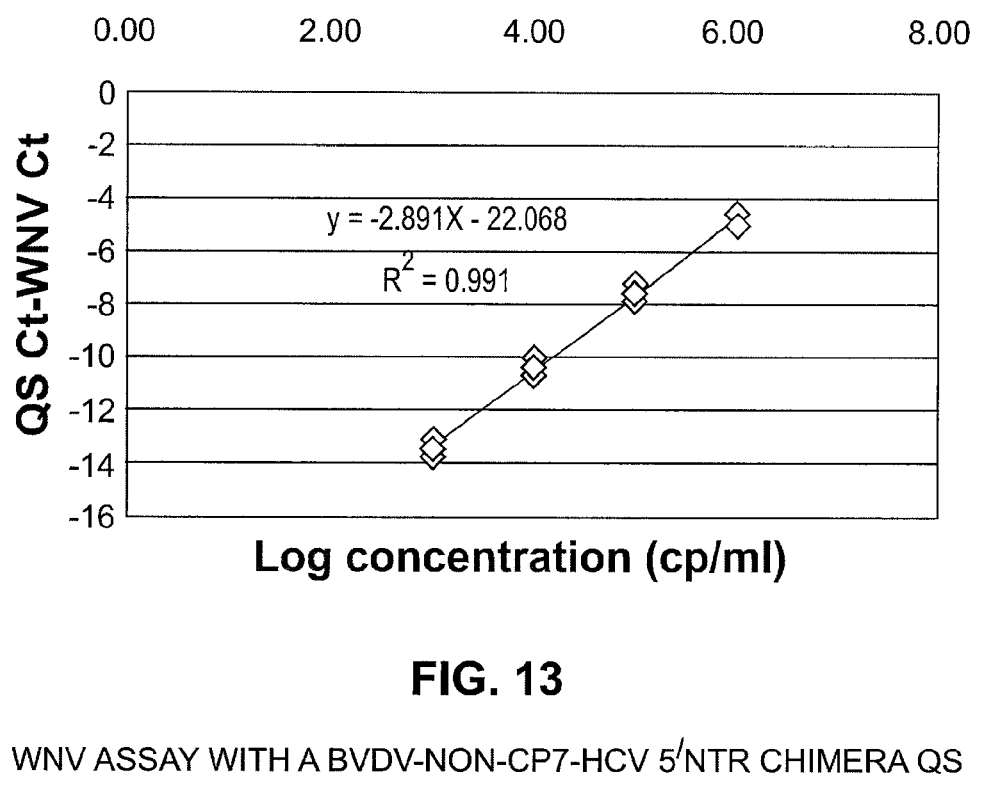

FIG. 13 shows the results of linear regression analysis of a West Nile Virus (WNV assay) with HCV-BVDV chimeric RNA as an internal quantification standard (QS). A slope of 2.891 and a coefficient of determination of 0.996 was obtained.

Table 1 shows virus titers obtained for BVDV-non-CP7 and BVDV-non-CP7+cloning site chimera at three days post infection (1st re-infection).

Table 2 shows virus titers obtained for BVDV-non-CP7 and the BVDV-non-CP7-HCV 5'NTR chimera at three days post transfection of viral RNA into MDBK cells. Moreover, virus titers are shown at three days post infection of MDBK cells measured in the course of several re-infection experiments with virus-containing supernatant as indicated. Up to seven re-infection experiments were performed.

Table 3 shows the data for growth curves shown in FIGS. 10 and 11.

Table 4 shows the non-infectivity data obtained for the BVDV-non-CP7-HCV-5'NTR chimera at various times and at three different temperatures of treatment with indicated concentrations of β-propiolactone. Immunofluorescence data (IF) measuring viral replication are indicated as + (viral replication detectable) and − (no viral replication detectable due to inactivation by the indicated concentration of β-propiolactone).

Table 5 shows the determination of the titer of the HCV signal of a Pestivirus BVDV-non-CP7-HCV 5'NTR chimera culture. Positive HCV signal was obtained using real-time PCR amplification for two Pestivirus RNA chimeras (BVDV-nonCP7-HCV 5'NTR, K4 and K8) and an HCV control. K4 and K8 Pestivirus RNA chimeras both showed an early Ct high titer HCV signal, indicating successful integration of the HCV 5'NTR into BVDV.

Table 6 shows the HCV signal obtained using real-time PCR amplification for two Pestivirus RNA chimeras and an HCV control with and without reverse transcriptase (RT) Results of a reverse transcriptase (RT) based PCR demonstrated that Pestivirus RNA chimera HCV signal was derived from RNA, not DNA.

Table 7 shows the resistance of the Pestivirus chimera BVDV-non-CP7-HCV 5'NTR to ribonuclease (RNase) digestion. Ct values are shown for two Pestivirus RNA chimeras and an HCV control without RNase treatment, and when RNase was present before or after extraction.

DETAILED DESCRIPTION OF THE INVENTION

RNA viruses are prevalent human and animal pathogens. Analytical NAT assays have been developed to allow detection of RNA viruses in infected individuals. A large group of RNA viruses are the positive-strand ssRNA viruses (Baltimore Group IV), which have their viral genome directly utilized as an mRNA. Positive-strand ssRNA viruses include many families of viruses that severely impact health and function in livestock and humans, such as the common cold virus (Rhinovirus), Poliovirus, the Hepatitis A and C viruses, the Dengue and Yellow fever viruses, and the SARS virus. Currently, safe and reliable analytical assays for the detection of RNA viruses are needed, including quality control materials for these assays.

The family Flaviviridae in Group IV includes three known genera, two of which affect humans. The genus *Flavivirus* includes, for example, Yellow fever virus, West Nile virus, Dengue fever virus, St. Louis encephalitis virus, Tick-borne encephalitis virus, and Japanese encephalitis virus. The genus *Hepacivirus* includes the Hepatitis C viruses (HCVs). The third genus *Pestivirus* affects livestock, and includes Classical Swine Fever Virus (CSFV), Border Disease Virus (BDV) and Bovine Viral Diarrhea Virus (BVDV). While each Flaviviridae member has a definitive host (cell) tropism and disease specifics, each also shares a significant degree of structural relatedness for the family Flaviviridae. In particular, each such member has a similar virus morphology and high degree of conservation of the genomic organization.

Recognition of the genomic structural similarities within the Flaviviridae family has allowed the opportunity of cross-utilization of intact Flaviviridae viral genomes for research and medical diagnosis purposes. For example, BVDV has been widely accepted as a surrogate virus for HCV inactivation studies. HCV infects humans, but, so far, only certain genomic subtypes or hybrid forms of these subtypes grow well in cell culture. The genome structure of BVDV, however, is generally similar to that of HCV, and BVDV does not infect humans. The use of a genome of a surrogate virus as quality control (QC) material in analytical assays, however, is not always applicable. Quality control materials for diagnostic RNA nucleic acid tests (target or signal amplification based) are often based on purified "naked" RNA or surrogate materials like Armored RNA. It would be preferable to have a quality control material that is as similar as possible to the target analyte so that all steps of the analytical process are mimicked as closely as possible.

The genome of the members of the Flaviviridae family is a single stranded, non-segmented RNA ranging in length from about 10 kb to 16 kb. The viral RNA contains a long open reading frame (ORF) encoding at least three major viral structural proteins and at least six nonstructural proteins. The ORF is flanked by 5' and 3'-nontranslated regions (5'NTR and 3'NTR) that range in length from about 100 to several hundred nucleotides (Lindenbach et al., Flaviviridae: the viruses and their Replication, in Fields virology, 5th ed., Knipe et al., eds., Lippincott, 2007, p 1101-52).

There is complexity in the functions of the Flaviviridae RNA. The viral RNA genome interacts with the host cell translation machinery to serve as a messenger RNA for the translation of viral proteins, as well as functioning as a template for viral RNA replication. Both the 5'NTR and 3'NTR are rich in defined RNA structure motifs known to be important for both the viral RNA translation and viral RNA replication functions (Lindenbach et al., see above). Along both processes, the NTRs are believed to functionally interact with each other as well as with host-cell encoded regulatory factors, such as the NFAR proteins (Isken et al., 2003; 2004; 2007). The 3'NTR of Flaviviridae is generally composed of a variable (less conserved) region (3'V) and a constant (conserved) region (3'C) (Deng and Brock, 1993). With different members of each Flaviviridae genus, the 3'C was shown to contain RNA elements that are essential for viral RNA replication while parts of the 3'V region were indicated to be dispensable for replication (reviewed by Isken and Behrens, 2006, in Molecular Biology of the Flavivirus; Horizonbioscience, p 101-134). Detailed investigations of the 3'V region of the BVDV genome revealed that 3'V, as a whole, is not dispensable for viral replication and that it acts as an important modulator of the viral translation and replication process (Isken et al., 2003; Isken et al. 2004).

The 3'NTRs of Pestiviruses have a length of approximately 190-230 nucleotides and display a high degree of similarity between the different virus members. The 3'V portion of the Pestivirus 3'NTR has defined recognizable regions. Structurally, while there is sequence heterogeneity between different Pestivirus strains, the pestiviral 3'V region generally forms two thermodynamically unstable stem-loop structures, termed $SL_{stop}$ (also SLIII) and SLII. It also contains at least one copy of a 12 nucleotide consensus sequence designated as a UGA box motif (Isken et al 2003; 2004; Pankratz et al., 2005, J Virol. 79:9119-27). Further, there is conservation within the pestiviral (and all Flaviviridae) 3'V regarding the presence of so-called pseudo-stop codons. The pseudo-stop codons are nucleotide triplets in the 3'V region of the 3'NTR that resemble translational stop codons, which are present 'in frame' (following the translational triplet code) with the viral open reading frame. Mutational and structural analysis showed that the integrity of the 3'V region and the presence of UGA boxes and pseudo-stop codons are important for the binding of the NFAR host proteins and for accurate termination of translation of the viral RNA, respectively. In summary, these factors were demonstrated to represent essential determinants of the viral RNA replication process (Isken et al, 2003; Isken et al., 2004).

The structurally complex and conserved 5'NTR and 3'NTR of Flaviviridae present target regions that may be utilized for the detection of these RNA viruses in analytical assays. This is particularly true for analytical methods based on target amplification, such as polymerase chain reaction (PCR) or transcript mediated amplification (TMA). The 5' NTR of the genus Flavivirus has here been commonly used as a target sequence for assays like HCV (Nolte F S, Green A M, Fiebelkorn K R, Caliendo A M, Sturchio C, Grunwald A, Healy M. Clinical evaluation of two methods for genotyping hepatitis C virus based on analysis of the 5' noncoding region. J Clin Microbiol. 2003 April; 41(4):1558-64) or West Nile virus (WNV). (Detection, Validation and Quantification of West Nile Virus RNA by the Alternative NAT WNV Assay V. Shyamala, S. Pichuantes, B. Jaitner, D. Madriaga, P. Arcangel, J. Cottrell, S. Nguyen, H. Huang, A. Medina-Selby, D. Coit, C. McCoin, D. Chien, B. Phelps. AABB Poster 2003 (http://www.chiron.com/docs/library/posters/aabb2003posters/aabb2003posters_5.pdf)

The detection of Group IV animal viruses uses known nucleic acid amplification techniques, such as polymerase chain reaction (PCR), Nucleic Acid Sequence Based Amplification (NASBA), Transcription-Mediated Amplification (TMA), other nucleic acid amplification technologies. Also signal amplification technologies like bDNA, can be used in medical research and in clinical diagnosis. Modern NAT testing allows sensitive detection of small amounts of RNA or DNA from viruses, bacteria and other cells or tissues. NAT testing usually consist of a series of sequential steps: sample preparation (purification and concentration of RNA or DNA), amplification of DNA (e.g. by PCR or TMA) and detection (e.g. by using signal generating fluorescence probes, bound free separation and detection of amplicon or gel band analysis). In the case of RNA, an additional reverse transcription step converting RNA into cDNA is required before amplification. Meaningful quality control of NAT assays requires monitoring of every step of this process. Typically, external and internal controls are used to quality control NAT assays.

One embodiment provides for the formation of stable virus chimeras by insertion of donor heterologous sequences into the 3' nontranslated region (3'NTR) of the RNA genome of the Flaviviridae Pestivirus. The chimeric RNA genomes of the Flaviviridae Pestivirus are sequence stable, replication competent, infectious and the genome encoded and assembled chimeric virus particles are RNase resistant.

The heterologous insert can be located within the Pestivirus 3'NTR. In a preferred embodiment, the insertion is within the 3' variable region (3'V) of the 3'NTR. Most preferably, the heterologous insert of the chimera is located between two stem-loop structures ($SL_{STOP}$ and SLII) within the 5'-terminal portion of the 3'NTR of the PestivirusRNA. The 3'NTR of the

*Pestivirus* chimera viral RNA contains pseudo stop-codons. The 3'NTR of the *Pestivirus* chimera viral RNA contains binding sites for the NF/NFAR proteins. The 3'NTR of the *Pestivirus* chimera viral RNA contains at least one UGA box motif, preferably the $UGA_{pos.cons.}$ motif.

These *Pestivirus* chimeras may be utilized as quality control materials in analytical RNA assays, including use as external positive controls (EC or PC), internal quality standards (IQS), internal controls (IC), internal quantification standards (QS), parallel complementary controls (PCC), calibrators, standards and in validation and verification panels. IC and QS are also referred to as IQS, since they can be the same substance. A difference between IC and QS is the way the signal generated by the substance is analyzed. The invention is useful for any detection assays including but not limited to target amplification technologies (e.g., PCR, TMA, NASBA, etc.) and signal amplification technologies (e.g., bDNA, etc.).

The same *Pestivirus* chimera can be used as EC, PC, calibrator or standard. This includes but is not limited to: standards traceable to an SI unit (e.g. mol), international standards, national standards (e.g. those provided by national measurement standards laboratories which establish standards for a country or organization like NIST in the USA or PTB (Physikalisch Technische Bundesantalt) in Germany) reference standards, certified reference materials, certified reference standards, JCTLM (Joint Committee for Traceability in Laboratory Medicine) approved materials, higher order reference materials and WHO standards (e.g. a WHO standard for HCV NAT assays). This substance contains target analyte sequences.

An RNA assay using e.g. a *Pestivirus* Chimera positive control and a *Pestivirus*Chimera QS would require two different chimeras. The inserted sequence would be different for the PC control material and QS control material.

An external control (EC), e.g. a positive control (PC), utilizes a composition that is the same or very similar to the target analyte sequence, but is assayed separately in an independent reaction from the target analyte sample. The EC or PC quality controls the same sequence as the target. In PCR, NASBA, TMA or other amplification technologies, an amplification product is formed identical or similar to the target, and the measurement signal generated is identical to the target signal. The external run control's purpose is to verify the EC test results fall within a predetermined acceptance criteria. The EC or PC are an integral part of a nucleic acid detection system (e.g. a PCR based diagnostic system) quality control and can be supplied as part of a reagent kit. See e.g. package insert for Roche COBAS AmpliPrep/COBAS TaqMan HIV-1 Test, Roche COBAS AmpliPrep/COBAS TaqMan HCV Test, ABBOTT RealTime HIV-1 test (69-6672/R1) or ABBOTT RealTime HCV test (69-6675/R1). These type of controls are, however, not necessarily part of a kit and can also be supplied as independent external run controls (e.g. OptiQual controls by AcroMetrix). Substances useful as external run control can also be used as calibrators for quantitative assays. While positive and negative controls indicate the general performance of the assay and allow a decision on reliability, calibrators help to measure the correct quantity of an analyte (e.g. the amount of HIV-1 in a patient's blood). Control and calibrator concepts for NAT assays are well known and have been described in e.g. ISO standard 17511:2003 and Section III G. of FDA's (1999) "Guidance for Industry In the Manufacture and Clinical Evaluation of In Vitro Tests to Detect Nucleic Acid Sequences of Human Immunodeficiency Viruses Types 1 and 2" and CLSI Guideline MM3-A2 Section 11.4.

Internal Quality Standards like Internal Controls (IC) and internal Quantification Standards (QS) are used as follows according to the Clinical and Laboratory Standards Institute, CLSI Guideline MM3-A2, Section 7: "Inhibition of a nucleic acid test results from the presence of substances that lead to a failure to achieve a positive signal. Interference of a nucleic acid test results in a reduction in assay performance leading to a false-negative or false-positive result. Inhibitors of amplification can be detected by the use of internal control templates, also referred to as recovery templates, or simply, internal controls. The control template can be added to the sample either prior to, or after sample preparation. If it is added prior to sample preparation, it can also serve as a control for the nucleic acid extraction." Due to its resistance to RNase degradation this invention can be added prior to sample preparation and serve as a control for the nucleic acid extraction. It could be even useful as a full process control including even earlier steps than sample preparation like sample collection and sample transport. The same guideline specifies a number of different control types useful for "Detection of Inhibitors and Interfering Substances" (Section 7.1, CLSI Guideline MM3-A2). A RNA virus chimera described in this invention can be used to provide the substances useful to serve as the internal controls described in the guideline. These controls are known in the art also as "unmodified target controls" (section 7.1.1., CLSI Guideline MM3-A2), "modified target controls" (section 7.1.2) and "Heterologous Internal Controls" (section 7.1.3, CLSI Guideline MM3-A2).

Internal quality standards (IQS) like IC or QS, are assayed simultaneously in the same reaction vessel as the target analyte. A negative patient result (e.g. for HIV or HCV) is only reported as "negative" or as "target not detected" if the IC or QS result falls within an acceptable range. In case the IQS results falls outside of the acceptance range the result is considered invalid and the sample should be retested.

An internal quantification standard (QS) is a type of IQS that allows precise quantification of the target analyte even in the presence of inhibitors. Both QS and Internal control (IC) generate signals distinguishable from the target signal. In the case of PCR, the amplification product and the generated signal are different and distinguishable from the target signal. IC and QS are used to detect and compensate (QS) for inhibition. They help to distinguish between a true negative and a false negative result. QS and IC sequences are often synthetic materials since they are usually designed to be different from the target, however, they should still behave like the target anayte (e.g. a virus) and go through the entire diagnostic process from sample preparation to detection. Ideally an IQS would in addition also monitor sample collection and transport.

U.S. Pat. Nos. 7,183,084 B2 and 7,192,745 describe a specialized type of internal quality control. The parallel complementary control (PCC) has the same thermodynamic properties as the target amplicon and therefore behaves in PCR like the target nucleic acid. The parallel complementary control provides one component to ensure an IQS behaves like the target analyte, however as a piece of naked RNA it would not be resistant to degradation by RNases when added into e.g. human plasma. To fully achieve that the PCC behaves like the target analyte during sample preparation, it needs to be encapsulated in a particle that behaves like the target analyte and can be added to the patient sample without being degraded. This invention is useful to provide RNase resistant parallel complementary internal controls formulated in a patient sample like matrix.

The chimeric RNA genome of the chimeric Pestivurs is useful to provide the RNA based internal controls and quantification standards described in U.S. Pat. No. 7,192,745.

This invention can further be used as a standard for the quantification of RNA as described in U.S. Pat. No. 7,183,084 B2 and further provide an RNase resistant form of a parallel complementary QS as described in U.S. Pat. No. 7,192,745.

Quantification Standards are commonly used in commercial NAT assay kits. Two examples are the Roche COBAS AmpliPrep/COBAS TaqMan HIV-1 Test kit or Roche COBAS AmpliPrep/COBAS TaqMan HCV Test kit. The QS material is described in the Roche COBAS AmpliPrep/COBAS TaqMan HIV-1 Test (P/N: 03542998 190) package insert (May 2007 Doc Rev. 1.0) as "HIV-1 QS (HIV-1 Quantification Standard). An HCV QS is used with the Roche COBAS AmpliPrep/COBAS TaqMan HCV Test and described in the package insert.

Two different *Pestivirus* chimeras could be used as a RNase resistant QS (Chimera Roche-1) and a positive control and a calibrator material (Chimera Roche-2) for the Roche COBAS AmpliPrep/COBAS TaqMan HIV-1 Test. Chimera Roche-2 would contain a heterologous HIV sequence detectable by the assay. Two additional chimeras would be required for the same purpose for the Roche COBAS AmpliPrep/COBAS TaqMan HCV Test kit (Chimera Roche-3 as HCV PC and Chimera Roche-4 as HCV QS).

Internal Controls are commonly used in commercial NAT assay kits. The *Pestivirus* chimeras could serve as an internal control (IC) for the detection of inhibition as used in the ABBOTT RealTime HIV-1 test kit (69-6672/R1) or ABBOTT RealTime HCV test kit (69-6675/R1). The Abbott Internal Controls are described in the package insert under "Reagents" List No. 2G31Y for the HIV-1 test and List No. 4J86Y for the HCV test. The IC target sequence for both tests was derived from the hydroxypyruvate reductase gene from *Cucurbita* pepo and delivered as an Armored RNA particle in negative human plasma. A *Pestivirus* RNA chimera could be used to provide the same sequence from the hydroxypyruvate reductase gene from *Cucurbita* pepo. A *Pestivirus* RNA chimera based internal control would mimic the target analyte better than Armored RNA, because it resembles HIV and HCV more than the MS2 bacteriophage.

A *Pestivirus* chimera could be used as a RNase resistant IC (Chimera Abbott-1) and a separate *Pestivirus*-HIV Chimera could be provided to serve as low and high positive control in the Abbott RealTime HIV-1 Control Kit (List No. 2G31-80) (Chimera Abbott-2). Chimera Abbott-2 could also be used as calibrator material in the Abbott realTime HIV-1 Calibrator Kit (List No. 2G31-70). One additional *Pestivirus*-HCV chimera (Chimera Abbott-3) would be required for controls and calibrators of the ABBOTT RealTime HCV test. Unlike the Roche TaqMan assays, which use separate Quantification Standards sequences for their HIV and HCV assay, the Abbott realTime PCR assays, use a common IC sequence for their HIV-1 and HCV assays.

The *Pestivirus* chimeras can be used as IC, QS, positive control and calibrator in commercial RNA NAT assays. For example, the chimeric RNA genome of the chimeric *Pestivirus* can be used as Positive control and calibrator in commercial RNA NAT assays. A second chimera would be required to serve as IC or QS. These controls can be packaged together or separate from the other required reagents. The materials can be lot specific or lot independent.

FIG. 1 shows a schematic alignment of the genomes of the *Pestivirus* BVDV virus and the *Hepacivirus* HCV virus. BVDV and HCV display a similar genomic organization. Both viral RNAs contain a long open reading frame (ORF; indicated as box) that is flanked by nontranslated regions (NTRs) at the 5' and 3' ends (single lines). The BVDV and HCV 5'NTRs contain internal ribosomal entry sites (IRES) that mediate translation of a viral polyprotein. Inspection of FIG. 1 shows that both viral RNAs encode a similar polyprotein (C, E1, E2, p7, NS2, NS3, NS4A, NS4B, NS5A, NS5B-COOH) that is co- and post-translationally processed by cellular and viral proteases to give rise to structural (C, E1, E2, p7) and nonstructural (NS2-NS5B) viral proteins (Lindenbach et al., 2007). The BVDV genome contains an additional nonstructural protein, the autoprotease $N^{PRO}$ and an additional envelope protein, $E^{RNS}$. The BVDV genome has a length of approximately 13 kb, while the HCV genome has a genome size of ca. 10 kb.

FIG. 2 shows in diagram form the strategy for the insertion of a heterologous sequence (HCV 5'NTR, amplicon) within the 3'NTR of the *Pestivirus* BVDV. FIG. 2 shows the insertion within the 3'NTR into a region between the two stem-loop structures $SL_{STOP}$ and SLII. This region was rather tolerant to the insertion of a variable sequence. However, the HCV 5'NTR should not be able to re-initiate translation as this would interfere with the initiation of replication at the immediate Tend. For that purpose, sequence elements in the BVDV 3'NTR that ensure immediate translation termination are left intact (Isken et al., 2004) The 5'NTR region of the HCV is circled in FIG. 2, and an arrow indicates the insertion of this sequence within the 3'NTR of *Pestivirus* BVDV. The structure of the stem-loops found in the 5'NTR and the 3'NTR of the HCV and the BVDV viruses is indicated. The known functions of the different regions of the viral NTRs during translation and RNA replication are indicated (Grassmann et al., 2005). The open reading frame (ORF) is shown as a box.

Figure 3:
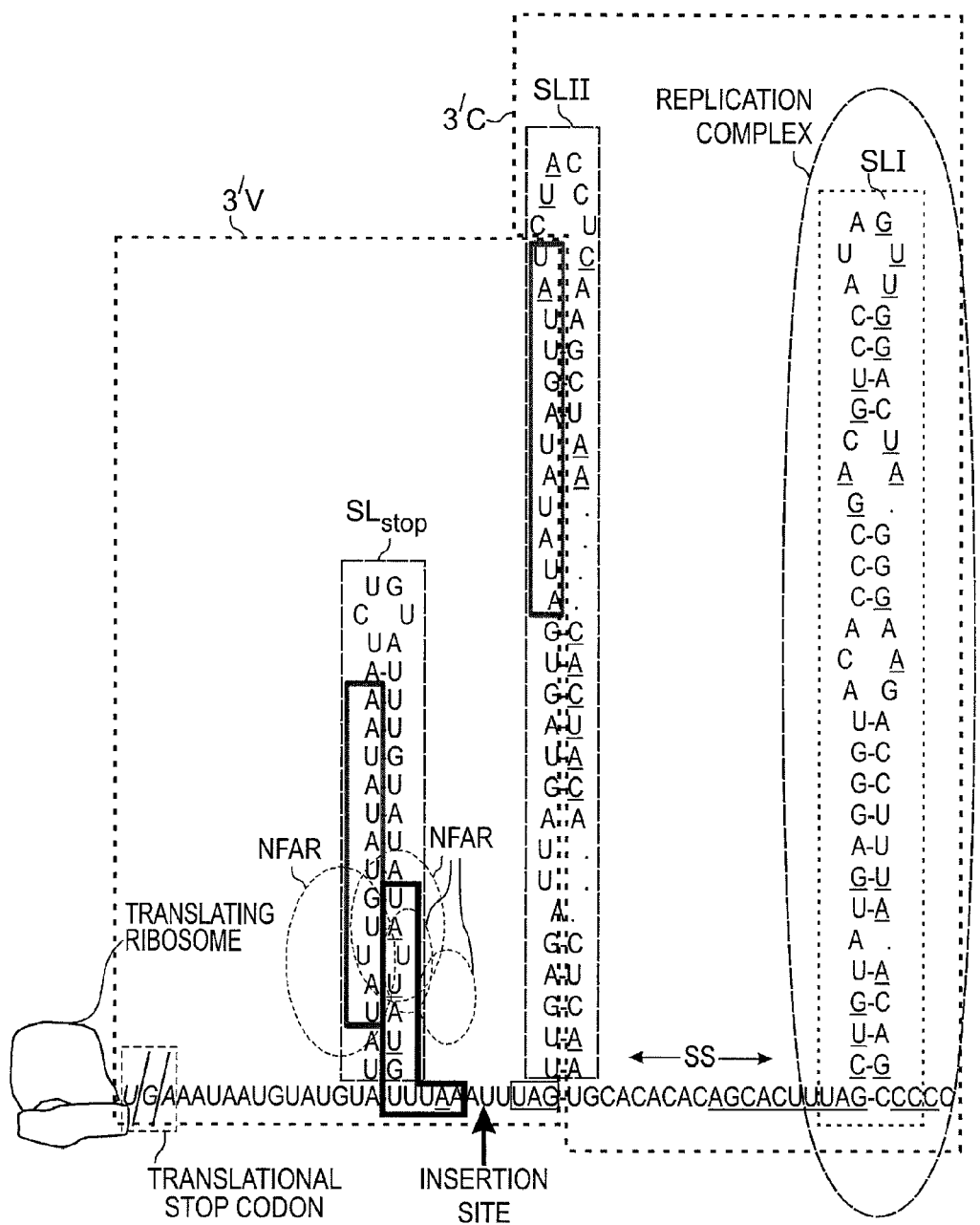

FIG. 3 shows a diagrammatic model of the structure and functions of the *Pestivirus* BVDV 3'NTR (Yu, et al., 1999; Isken et al., 2004). A representative sequence of the 3'NTR from BVDV (BVDV replicon DI9c, which is highly homologous to the 3'NTR of BVDV non-CP7; Behrens et al., J. Virol., 1998) is shown. The variable region (3'V) is involved in the coordination of translation and RNA replication by efficiently terminating translation. For this activity, binding of NFAR proteins to the 3'V region involving the UGA boxes is needed. The 3' variable region (3'V) and the 3' constant region (3'C) are each shown boxed with dashed lines. The 3'V represents the sequence following the translational stop codon (shown boxed; a stopping ribosome is schematized by a double structure); the border between the 3'V and the following 3'C region is indicated by juxtaposition of the dashed line boxes near the top of SLII. The constant region (3'C) is shown as the remainder of the 3'NTR. The 3'C is the region where the replication complex assembles, which is indicated by a large oval. The functional interactions of the 3'NTR are indicated diagrammatically for: the translating ribosome (double structure), the NFAR proteins (collection of circles), and the replication complex (large oval). SS indicates a highly conserved intervening region located between SLII and SL I. The large arrow indicates an insertion site for the heterologous RNA sequence for the formation of a stable and functional *Pestivirus* RNA chimera.

Figure 4:
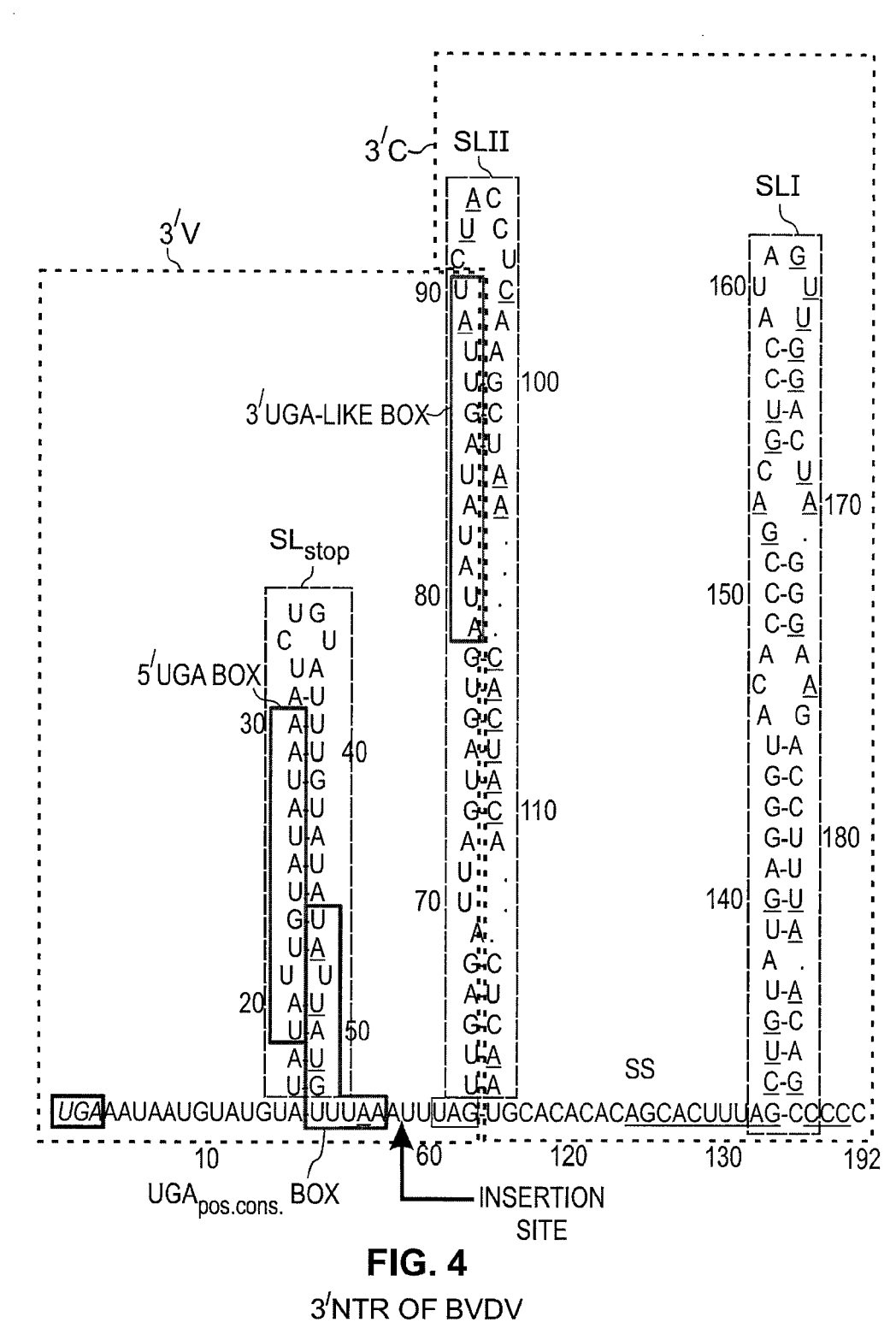

FIG. 4 discloses a more detailed diagram of the 3'NTR sequence of *Pestivirus*BVDV-DI9c, which is highly homologous to the 3'NTR of BVDV non-CP7 showing the 3'V and the 3'C regions. As in FIG. 3, the 3'V and the 3'C regions are indicated with dashed-line boxes. The 3'V region contains the $SL_{STOP}$ (SLIII) stem-loop and a portion of the SLII stem-loop, which ends after the end of the 3'UGA-like box and is marked by a juxtaposition of the dashed line boxes (at nucleotide 90; Deng and Brock, 1993). In FIG. 4, the 3'V region contained UGA box motifs, including: the 5'UGA box (nucleotides 19-30), the $UGA_{pos.cons.}$ box (nucleotides 46-57) and the 3'UGA-like box (nucleotides 79-90). As in FIG. 3, the large arrow indicates a preferred insertion site immediately following the SL$_{STOP}$ (SLIII) where a heterologous RNA sequence may be inserted for the formation of a stable and functional *Pestivirus* RNA chimera.

Figure 5A:
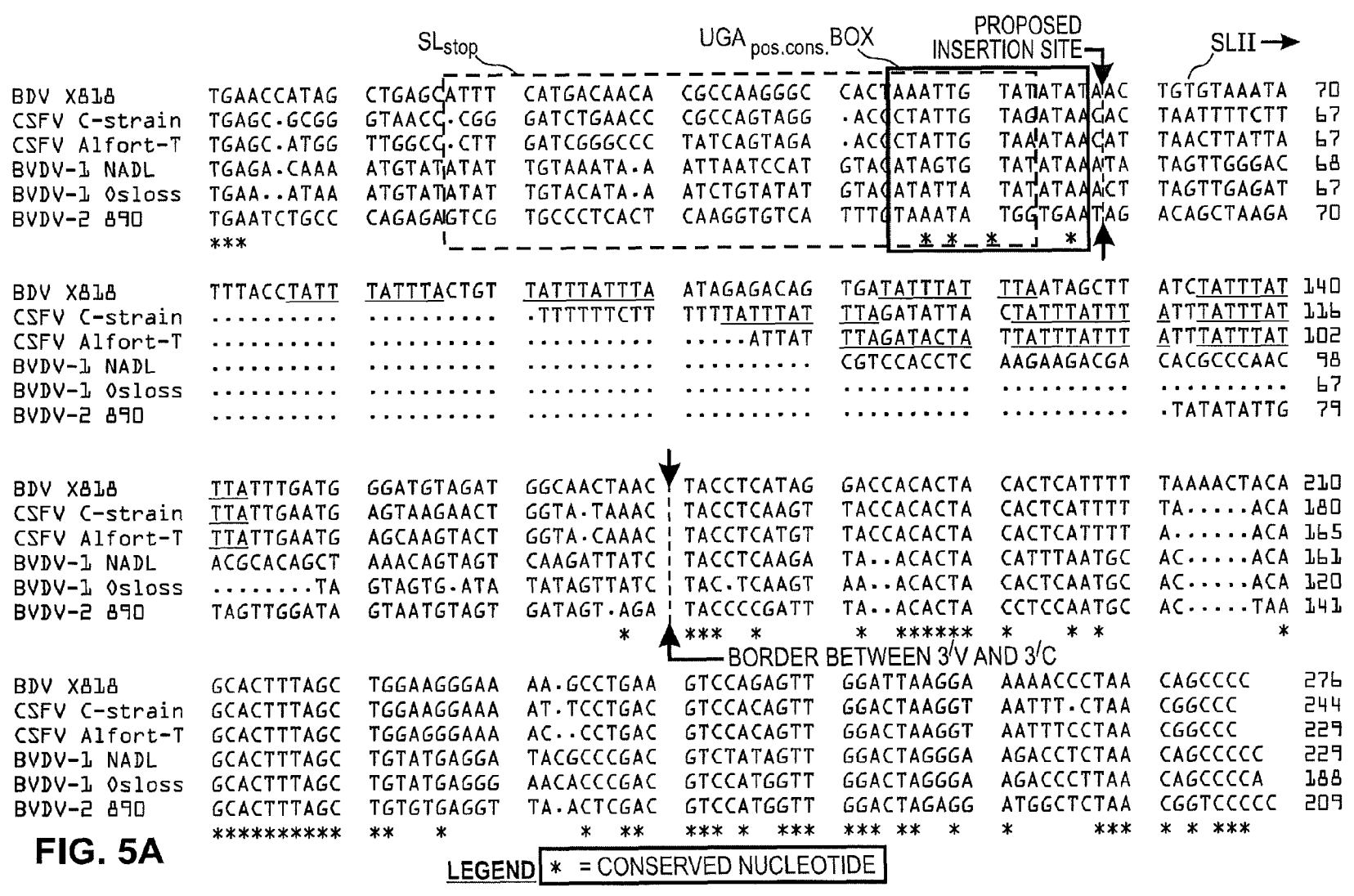

FIG. 5A shows an alignment of the 3'NTR for various strains of *Pestivirus*. On the left is an alignment of the 3'NTRs of different *Pestivirus* strains (Becher et al. J. Virol. 1998 72: 5165-5173). The sequences forming SL$_{STOP}$ (SLIII) and SLII are indicated. With all of the different *Pestivirus* strains, the predictions of the structural similarity of SLII and SLstop (SLIII) are analogous. The boxed area indicates the position of the UGA$_{pos.cons}$. box, which is located within the 3'V region and contains four nucleotides that are 100% conserved between all known *Pestivirus* strains (marked by asterisks). A thick arrow indicates the proposed border of the 3'V and 3'C regions of the 3'NTR of all these *Pestivirus* strains (Deng and Brock, 1993). The UGA$_{pos.cons}$. box has been found to be present at nearly identical positions in all pestiviral genomes, i.e. about 39-42 residues downstream of the ORF (Isken, 2003). The arrow indicates a preferred site where the heterologous insert was introduced into BVDV-non-CP7. FIG. 5B details the consensus sequence and conserved positions of the UGA box sequences of different *Pestivirus* strains (Isken et al., 2003). Given the analogous structural similarity of the stem-loop structures within the 3'V and the consensus of sequences within the UGA$_{pos.cons}$. box, the 3'NTR, therefore, may be commonly used for insertion of a heterologous sequence with all *Pestivirus*. The site immediately following the UGA$_{pos.cons}$. box is an example of a preferred site for all *Pestivirus* strains for insertion of a heterologous RNA sequence. The procedure described for the construction of a 3'NTR viral chimera can be used with all *Pestivirus* to create functional chimeric viruses that may be, for example, used as standards and controls for analytical assays.

EXAMPLE 1

Construction of BVDV-non-CP7 cDNA and Generation of Infectious Non-Cytopathic Viral RNA A modified cDNA of BVDV (type-1) strain CP7 was generated as a starting material for all subsequent procedures (Becher et al., 2000 J. Virol. 74: 7884-7894). The modification was performed such that the CP7 insert (Tautz et al., J. Virol. 1996 November; 70(11):7851-8) was removed to create a cDNA containing plasmid that encoded a BVDV "non-CP7" RNA biotype (M. Behrens, unpublished data). A similar construct was published earlier by Makoschey et al., (Vaccine, 2004, Sep. 3; 22(25-26):3285-94.) The complete sequence of the cDNA for the BVDV-non-CP7 is given as SEQ ID NO: 1.

The plasmid encoding the BVDV-non-CP7 cDNA was linearized by restriction digestion with the restriction endonuclease SmaI. In vitro transcripts were generated by run-off transcription using SP6 RNA polymerase. The viral RNA was generated by in vitro transcription using SP6 RNA polymerase. The in vitro generated BVDV-non-CP7 RNAs were transfected into Marbin Darby Bovine Kidney (MDBK) cells using standard protocols. Three (3) days post transfection, the cell culture supernatant was collected and used to either titrate the contained infectious virus particles or to re-infect other MDBK cells. Three days after re-infection, virus titers were determined and the cells examined for a cytopathic effect using standard procedures (Tautz et al., J. Virology, 1996, 70 (11):7851-8). Thus, the non-cytopathic nature of the generated virus was confirmed. The titrations revealed that 5×10$^6$ to 5×10$^7$ infectious virus particles were detectable per ml of cell culture supernatant (see also Table 1 and Table 2, data for BVDV-non-CP7).

EXAMPLE 2

Generation of Chimeric BVDV-non-CP7 cDNAs

The plasmid including the BVDV-non-CP7 cDNA (SEQ ID NO: 1) was then used to introduce the HCV 5'NTR sequence (HCV Coni cDNA; Lohmann et al., 1999) within the BVDV 3'NTR to obtain a functional chimeric viral sequence (BVDV-non-CP7-HCV 5'NTR).

For that purpose, a synthetic DNA fragment was generated commercially. This DNA fragment corresponded to the ClaI (initiating at pos. 11047 of the BVDV-non-CP7 cDNA sequence)/SmaI (initiating at pos. 12264 of BVDV-non-CP7 cDNA sequence) fragment of the BVDV-non-CP7 cDNA (SEQ ID NO:1), but also included an HCV 5'NTR insert (Con 1 subtype 1b isolate; Lohmann et al., 1999, Science. July 2: 285 (5424): 110-3) flanked by two restriction sites (SnaBI and PacI) and an additional TAA trinucleotide. The cDNA sequence of the HCV 5'NTR is given in SEQ ID NO: 2. This heterologous insert was positioned such that in corresponding RNA transcripts it was located between the UGA$_{pos.cons}$. box and the SLII stem-loop structure in the 3'V of the BVDV non-CP7 3'NTR (see FIGS. 3 and 4 for diagram of a preferred insertion site).

Figures 6D, 6E:
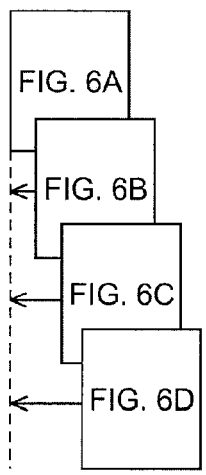
FIG. 6 shows the cDNA sequence of the BVDV-non-CP7-HCV 5'NTR chimera (SEQ ID NO: 3) with the restriction endonuclease sites for ClaI, part of SmaI, SnaBI and PacI indicated. The nucleotide exchanges (c changed into t) are also indicated.

Using standard recombinant cloning techniques, the respective ClaI/SmaI fragment was cloned into the BVDV-non-CP7 cDNA (SEQ ID NO:1) containing plasmid that was cut with the same restriction sites. Performing several independent ligations and screening of several hundred clones yielded recombinant plasmids encoding the chimeric cDNA. The resultant chimeric cDNA clone was termed BVDV-non-CP7-HCV 5'NTR cDNA (SEQ ID NO: 3). It thus encoded a heterologous sequence at position 12134, i.e., essentially two novel restriction sites and the HCV 5'NTR (SEQ ID NO: 2) placed within the sequence encoding the BVDV 3'NTR to yield the BVDV-non-CP7-HCV 5'NTR chimera (SEQ ID NO: 3, FIG. 6). Note that the introduced HCV 5'NTR sequence was modified at two single nucleotide positions to remove internal SmaI sites (c→t at position 12269 and c→t at pos. 12456 of the BVDV-non-CP7-HCV 5' NTR cDNA) These nucleotide exchanges were necessary to allow linearization of the BVDV-non-CP7-HCV 5' NTR cDNA encoding plasmid by SmaI for run off transcription by SP6 RNA polymerase to generate viral RNA molecules that ended with the correct 3' terminus. FIG. 6 shows the cDNA sequence of the BVDV-non-CP7-HCV 5'NTR chimera with the restriction endonuclease sites indicated for ClaI, part of SmaI, SnaBI and PacI. The nucleotide exchanges (c changed into t) are also indicated.

Applying the same strategy, an insert encoding two restriction sites, SnaBI and PacI) was introduced into the BVDV-non-CP7 cDNA containing plasmid (SEQ ID NO: 1) at the same position (insertion at position 12134). This construct was termed BVDV-non-CP7+ cloning site, and the cDNA sequence is given in SEQ ID No: 4. FIG. 7 shows the cDNA sequence of the BVDV-non-CP7+cloning site chimera with the restriction endonuclease sites indicated for ClaI, part of SmaI, for SnaBI and PacI.

The correctness of the respective inserts was verified by restriction analysis of the cDNA encoding plasmids and sequencing as shown in FIG. 8. FIG. 8 shows sequence details of the 3'NTR region for the construction of the *Pestivirus* chimera sequences (given as DNA sequence). FIG. 8 (A+B)

shows a comparison of the cDNA sequences of the 3'NTR of the BVDV-non-CP7+cloning site chimera and the sequence of the 3'NTR of BVDV-non-CP7.) FIG. 8 (A+C) shows a comparison of the sequence of the 3' NTR of the BVDV-non-CP7-HCV5'NTR chimera and the sequence of the 3'NTR of BVDV-non-CP7.

In FIG. 8, the translational stop-codon (tga) at the end of the open reading frame (ORF) is boxed, and pseudo-stop codons are underlined. Additional and specifically changed sequences (taa) are shown in italics. The SnaBI restriction site (tacgta) and the PacI restriction site (ttaattaa) are shown in brackets. The 5'UGA box (tattgtatataa)(SEQ ID NO: 32) and the UGApos.cons. box (tattatgtttaa)(SEQ ID NO: 33) are indicated by the small dashed-line boxes. FIG. 8A shows the 3' NTR of BVDV-non-CP7 (SEQ ID NO: 5), which corresponds to that for the wild type starting material. (As noted above, the complete sequence of the BVDV-non-CP7 is given as SEQ ID NO: 1.) FIG. 8B shows the 3' NTR of the BVDV-non-CP7+cloning site chimera, which has the SnaBI/PacI restriction endonuclease cloning site insert (SEQ ID NO: 6). (As noted above, the complete sequence of the BVDV-non-CP7+cloning site is given in SEQ ID NO: 4, FIG. 7.) FIG. 8C shows the sequence of the 3'NTR region for the BVDV-non-CP7-HCV 5'NTR chimera (SEQ ID NO: 7). The sequence of the HCV 5'NTR insert (SEQ ID NO. 2) is indicated by the large, dashed-line box. (As noted above, the complete sequence of the BVDV-non-CP7-HCV-5'NTR chimera is given as SEQ ID NO: 3, FIG. 6.)

EXAMPLE 3

Stability of the cDNA Plasmid Constructs of the Newly-Generated *Pestivirus*BVDV Chimeras Several individually isolated cDNA plasmids encoding either BVDV-non-CP7 (SEQ ID NO: 1), the BVDV-non-CP7+cloning site chimera (SEQ ID NO: 4), or the BVDV-non-CP7-HCV 5'NTR chimera (SEQ ID NO: 3) were grown in *E. coli*. The plasmids were prepared using standard procedures and the authenticity of the inserts was verified by DNA sequencing. The overall stabilities of the plasmids through several passages in *E. coli* were verified by performing restriction analysis using multiple restriction enzymes and sequencing.

EXAMPLE 4

The *Pestivirus* BVDV Chimeric RNAs are Replication Competent and Generate Infectious Virus Particles at Similar Titers as the Original BVDV-non-CP7 RNA The plasmids encoding the chimeric cDNAs were linearized with the restriction endonuclease SmaI. In vitro transcription was performed with SP6 RNA polymerase using standard protocols. The viral RNA then was transfected into Marbin Darby bovine kidney cells (MDBK) using standard procedures. Three (3) days post transfection, the virus titer contained in the cell culture supernatant was measured by a standard titration protocol. The transfection supernatant was then used to re-infect cells and to re-harvest and re-titrate virus at 3 day intervals. As shown in Table 1, the virus titers obtained after the initial transfection and re-infection were found to be similar with experiments that were performed with the RNAs of BVDV-non-CP7 and two BVDV-non-CP7+ cloning site chimeras (K17 and K25), respectively.

TABLE 1

Virus titers for BVDV-non-CP7 and BVDV-non-CP7 + cloning site chimera after transfection and 1st re-infection.

|  | BVDV-non-CP7 | BVDV-non-CP7 + cloning site chimera, K17 | BVDV-non-CP7 + cloning site chimera, K25 | Days post infection |
|---|---|---|---|---|
| Titer (/ml) | 6.30E+05 | 9.40E+06 | 1.30E+06 | 3 (1st re-infection) |

As shown in Table 2 (line 1) similar virus titers to those found in Table 1 were also obtained with transfection and first re-infection experiments when the BVDV-non-CP7 and the BVDV-non-CP7-HCV 5'NTR chimera were tested, respectively. As also shown in Table 2, similar virus titers were found throughout subsequent re-infection experiments (up to 7 re-infection passages) for the BVDV-non-CP7 and the BVDV-non-CP7-HCV 5'NTR chimera, respectively.

TABLE 2

Virus titers at various times post-infection for BVDV-non-CP7 and BVDV-non-CP7-HCV 5'NTR chimera Titer (/ml)

| BVDV-non-CP7 | BVDV-nonCP7-HCV 5'NTR chimera | Days post trasfection | Days post infection |
|---|---|---|---|
| 1.20E+06 | 5.10E+06 | 3 |  |
| 2.10E+07 | 1.30E+07 |  | 3 (1st re-infection) |
| 2.20E+05 | 4.90E+05 |  | 3 (2nd re-infection) |
| 1.70E+06 | 6.10E+06 |  | 3 (3rd re-infection) |
| 4.30E+06 | 3.20E+07 |  | 3 (4th re-infection) |
| 7.40E+07 | 9.30E+07 |  | 3 (7th re-infection) [1] |

[1] Titrations of 5th and 6th re-infections were not performed

To test for viral protein synthesis, cells that were infected with virus (see above) were investigated by immunofluorescence (IF) to detect newly synthesized NS3 protein. IF-detectable synthesis of NS3 protein unambiguously indicated RNA replication. Protein synthesis that occurred by translation of the viral RNA within the cell was not detectable. In other words, only if the RNA amplified would sufficient protein be synthesized and thus become detectable by IF testing (Behrens et al., 1998; J Virol. 1998 March; 72(3):2364-72). We detected NS3 synthesis with both chimeras (BVDV-nonCP7+ cloning site and BVDV-nonCP7-HCV 5'NTR), as well as with the BVDV-non-CP7 throughout all of the performed transfection/infection experiments that are shown in Tables 1 and 2. In sum, these results showed that following transfection of the RNAs into host cells, the *Pestivirus* chimeras BVDV-non-CP7+cloning sites and BVDV-non-CP7-HCV 5'NTR showed identical rates of viral protein synthesis and of infectious viral particle formation.

EXAMPLE 5

Growth of BVDV-non-CP7 and the BVDV-non-CP7-HCV 5'NTR Chimera

The growth characteristics of the BVDV-non-CP7-HCV 5'NTR chimera was compared with that of the BVDV-non-CP7. As shown in FIGS. 9 and 10, the growth behavior of the newly generated BVDV-non-CP7-HCV 5'NTR chimera (measured by one-step growth curves over a 72 hour time period) was indistinguishable from that obtained for the BVDV-non-CP7. The data for FIGS. 9 and 10 is given in Table 3.

TABLE 3

Growth curve data for BVDV-non-CP7 and BVDV-non-CP7-HCV 5'NTR chimera (see FIGS. 9 and 10)

| | Titer/ml | |
|---|---|---|
| TIME (hr) | BVDV-non-CP7 | BVDV-non-CP7-HCV 5'NTR chimera |
| 12 | 7.50E+02 | 4.50E+02 |
| 18 | 3.70E+03 | 2.50E+03 |
| 24 | 1.90E+04 | 1.90E+04 |
| 36 | 2.30E+06 | 2.20E+06 |
| 48 | 3.00E+08 | 4.00E+08 |
| 72 | 4.00E+08 | 5.00E+08 |

EXAMPLE 6

Long Term Stability of the *Pestivirus* BVDV-non-CP7-HCV 5'NTR Chimera (7 Passages)

The *Pestivirus* BVDV-non-CP7-HCV 5' NTR chimera was passaged (performing subsequent re-infection experiments) for up to seven times (several weeks), without loss of titer (see Table 2; see Example 4). As shown in Table 2, measuring the virus titers after seven passages revealed no significant differences in the titer of the BVDV-non-CP7-HCV 5'NTR chimera with respect to the titer of BVDV-non-CP7 (commonly, average titers of $5 \times 10^7$/ml cell culture supernatant were measured). These findings allowed stable manufacturing of larger amounts (>1 liter) of virus in culture.

To determine the stability of the genomic sequence of the BVDV non-CP7-HCV 5'NTR chimera, after three passages as well as after seven passages, total viral RNA was isolated from the infected cells (using a standard procedure; Behrens et al., 1998; J Virol. 1998 March; 72(3):2364-72) and the BVDV 3'NTR amplified by RT-PCR. After cloning of the PCR fragments (cloning site BamHI, XbaI), five different clones were sequenced. The clones generated from the $3^{rd}$ passage showed no nucleotide exchanges (data not shown). The clones generated from the $7^{th}$ passage showed very few changes: Two of five clones that were obtained after the $7^{th}$ passage displayed one nucleotide exchange within the HCV insert, while two clones showed mutations within the genomic BVDV sequence, and one clone showed no changes. FIG. 11 shows the sequence details for these five clones obtained after the $7^{th}$ passage: clone 1 (FIG. 11A) (SEQ ID NO: 8) had a g-t exchange in the HCV insert; clone 2 (FIG. 11B) (SEQ ID NO: 9) had a c-t exchange in the HCV insert; clone 3 (FIG. 11C) (SEQ ID NO: 10) had a t-c exchange in the BVDV sequence; clone 4 (FIG. 11D) (SEQ ID NO: 11) had no sequence changes, and clone 5 (FIG. 11E) (SEQ ID NO: 12) had g deleted in the BVDV sequence. The HCV insert in the BVDV non-CP7-HCV 5'NTR chimera, therefore, had approximately the same stability as the surrounding genomic BVDV sequence.

EXAMPLE 7

Inactivation of the *Pestivirus* BVDV Chimera with β-propiolactone

Inactivation experiments of the BVDV-non-CP7-HCV 5'NTR virus particles were performed. The culture supernatant of BVDV-non-CP7-HCV 5'NTR infected MDBK cells (7th re-infection, virus titer approximately $1 \times 10^8$ per ml) was incubated with various concentrations of β-propiolactone for various times at three different temperatures (4° C., 25° C. and 37° C.) as indicated in Table 4. The β-propiolactone is a protein-modifying agent known to react with amides of the $NH_3$ group of lysine or arginine. Following incubation, the culture supernatants were titrated and tested by immunofluoresence (IF, see Example 4) to detect viral RNA replication, and thus detection of infectious virus for the cultured cells. The data obtained are shown in Table 4. When infectious virus was detectable throughout several titrations (12×1:5 steps), it was scored as (+)-IF. When no infectious virus was detectable throughout several titrations (12×1:5 steps), it was scored (−)-IF. As shown below, when the culture supernatant was incubated at 0.03% β-propiolactone at 37° C. for 120 min, the *Pestivirus* chimeric virus was inactivated, while there was no toxicity for the cultured cells.

TABLE 4

Determination of inactivation of *Pestivirus* BVDV-non-CP7-HVC 5' NTR chimera.

| | | β-propiolactone Concentration | | | | |
|---|---|---|---|---|---|---|
| TIME | ° C. | 0.01% | 0.03% | 0.05% | 0.1% | 0.3% |
| 60 min | 4° C. | IF+ | IF+ | IF+ | nd | nd |
| 120 min | 4° C. | IF+ | IF+ | IF- [2] | nd | nd |
| 240 min | 4° C. | IF+ | IF- [1] | IF- [2] | nd | nd |
| 15 min | 25° C. | IF+ | IF- [1] | IF- [1] | nd | nd |
| 30 min | 25° C. | IF+ | IF- [1] | IF- [1] | nd | nd |
| 60 min | 25° C. | nd | nd | nd | IF- [2] | IF- [3] |
| 120 min | 25° C. | IF+ | IF- [1] | IF- [1] | nd | nd |
| 180 min | 25° C. | IF+ | IF- [1] | IF- [1] | nd | nd |
| 15 min | 37° C. | IF+ | IF- [1] | IF- [1] | nd | nd |
| 30 min | 37° C. | IF+ | IF- [1] | IF- [1] | nd | nd |
| 120 min | 37° C. | IF+ | IF- | IF- [1] | nd | nd |

Legend:
[1] Initial dilution toxic for cells;
[2] Initial dilution and 1:5 dilution toxic for cells;
[3] Initial dilution, 1:5 dilution, and 1:25 dilution toxic for cells. In bold, optimal inactivation condition.

EXAMPLE 8

Testing of HCV-BVDV Chimera for Positive HCV Signal in Real-Time PCR and Estimation of Titer Two DNA plasmid BVDV chimera clones (K4 and K8) expected to contain the HCV 5'NTR sequence were transcribed into full length viral RNA. MDBK cells were transfected with viral RNA and cultured. The cells produced infectious viral particles, which were subsequently harvested and tested for containing the expected HCV 5'NTR RNA sequence (see Example 3).

Viral RNA was extracted from clone K4 and K8 supernatant, as well as a HCV control, using the QIAamp Virus MinElute Kit (QIAGEN). Reverse transcription real time PCR was performed using the Roche TaqMan HCV ASR. K4 and K8 BVDV-HCV chimeras showed high titer HCV signals indicating successful integration of the HCV 5'NTR into BVDV (Table 5). Based on the observed Ct values it was estimated both chimeras produced a signal equivalent to about 300 million HCV IU/mL. One IU has previously been estimated to be roughly equivalent to 2.63 viral particles. The estimated titer of 7.8E+08 virus particles/mL is higher than the observed 9.30E+07 infectious particles/mL (Table 2) because only about one in 10 viral particles is infectious. HCV patient samples rarely exceed 10 million IU/mL.

It should be noted that International Units (IU) are a different unit of measure than the previously mentioned "infectious particles" in Table 2. The HCV control showed the expected value.

TABLE 5

Estimation of BVDV-non-CP-7-HCV 5'NTR chimera titer using the Roche HCV ASR

| Samples | Ct | QS Ct | Dilution Factor | log IU/ml | Final Conc IU/ml |
|---|---|---|---|---|---|
| HCV-BVDV K8 | 20.3 | 31.4 | 10 | 7.46 | 2.9.E+08 |
| HCV-BVDV K4 | 20.2 | 31.4 | 10 | 7.49 | 3.1.E+08 |
| HCV control | 26.6 | 31.3 | 1 | 5.30 | 2.0.E+05 |

EXAMPLE 9

The HCV Signal for BVDV-nonCP7-HCV 5'NTR Chimera was from RNA

We tested whether the positive HCV signal in Example 6 was generated from RNA or an unlikely DNA contamination from the cDNA plasmid encoding the BVDV-non-CP7-HCV 5'NTR chimera RNA. The BVDV-nonCP7-HCV 5'NTR K4 and K8 chimera samples were extracted using a QIAamp Virus MinElute Kit (QIAGEN). PCR amplifications were performed using two separate preparations of the TaqMan One-Step RT-PCR Master Mix Reagents (ABI) and a reverse transcription PCR was performed using an HCV PCR assay based on real time detection. One master mix was prepared with no reverse transcriptase (RT), while the other master mix contained the reverse transcriptase enzyme. The RT enzyme is required for converting RNA into cDNA, which can be used during PCR by a thermostable DNA polymerase as substrate for amplification. RNA is no substrate for the DNA polymerase. Without the RT, it was expected if RNA were the source of the HCV signal, no DNA template would be made, and thus no amplification by DNA polymerase could occur. However without RT, if DNA were the source of the HCV signal, it would serve as the template for DNA polymerase and a HCV signal would be generated.

BVDV-non-CP7-HCV 5 NTR chimera samples were prepared with both master mixes, and run on the same 96-well plate on the ABI 7300. As shown in Table 6, the BVDV-non-CP7-HCV 5 NTR chimera samples and HCV samples only amplified when the reverse transcriptase (RT) was present. This allowed the conclusion that the BVDV-non-CP7-HCV 5 NTR chimera samples contain RNA, not DNA. Also, the HCV control signal originated as expected from RNA.

TABLE 6

BVDV-non-CP7-HCV 5'NTR chimera signal is derived from RNA

| sample | Ct with RT | Ct without RT |
|---|---|---|
| BVDV-non-CP7-HCV-5'NTR chimera, K8 | 26.5 | no signal |
| BVDV-non-CP7-HCV-5'NTR chimera, K4 | 26.7 | no signal |
| HCV control | 33.1 | no signal |

EXAMPLE 10

The BVDV-non-CP7-HCV 5'NTR Chimera is RNase Resistant

We tested to determine whether the BVDV-non-CP7-HCV 5'NTR chimera RNA was resistant to RNase degradation because its RNA was protected within an intact virion, or if it existed as non-encapsulated, free RNA vulnerable to enzymatic digestion with RNase.

The two BVDV-non-CP7-HCV 5'NTR chimeras K4 and K8 and an HCV control were tested under two conditions. In one experiment, an RNase digest was done prior to extraction (QIAamp Virus MinElute Kit (QIAGEN)). Loss of signal in PCR amplification would indicate free, unprotected RNA. In a second control condition, no RNase was added to the HCV-BVDV chimera samples before extraction. If the chimeric RNA was non-encapsulated, the RNase digest would degrade the free RNA. This degradation would either eliminate the HCV signal completely, or shift the Ct to a significantly higher value.

As shown in Table 7, the Ct values for the BVDV-non-CP7-HCV 5 NTR chimeras K4 and K8 did not significantly change after RNase treatment, indicating the RNA is encapsulated, and therefore protected from RNA degradation. To control RNase digestion was working, we extracted the HCV RNA and treated it with RNase prior to amplification. The HCV signal was eliminated completely, confirming the RNase digest was working as expected.

TABLE 7

Resistance of BVDV-non-CP7-HCV 5'NTR chimera RNA to RNase

| Sample | Ct: No RNase Treatment | Ct: RNase Digest Before Extraction | Ct: RNase Digest After Extraction |
|---|---|---|---|
| BVDV-non-CP7-HCV 5'NTR chimera K8 | 34.9 | 34.8 | Not tested |
| BVDV-non-CP7-HCV 5'NTR chimera K4 | 34.0 | 35.2 | Not tested |
| HCV | 38.1 | 37.7 | Negative |

EXAMPLE 11

Use of BVDV-non-CP7-HCV 5'NTR Chimera as an HCV Calibrator for HCV NAT Amplification Assays The performance of a known HCV calibrator (AcroMetrix OptiQuant HCV) consisting of intact naturally occurring HCV virions in plasma was compared with the performance of a BVDV-non-CP7-HCV 5 NTR chimeric HCV calibrator, which also consisted of intact virions in plasma. First, a value assignment of the 0.05% β-propiolactone inactivated BVDV-non-CP7-HCV 5 NTR stock material in plasma was conducted using an HCV Acrometrix Primary Standard (APS). The HCV APS is metrologically traceable to the Second HCV WHO Standard (NIBSC code: 96/798). The BVDV-non-CP7-HCV 5 NTR chimera sample was diluted to the same levels as the OptiQuant HCV panel members: 5E6, 5E5, 5E4, 5E3, 5E2, 5E1 IU/ml. The OptiQuant HCV panel had also been value assigned using the HCV APS. RNA extraction for the calibrators was performed using the QIAamp Virus MinElute Kit (QIAGEN) on the automated QIAcube instrument (QIAGEN). Real-time PCR was performed using a reverse transcription PCR HCV assay based on real time detection.

As shown in FIG. 12, the measured Ct values were plotted against the log of HCV IU/ml. The linear regression lines were equivalent for HCV and BVDV-non-CP7-HCV 5 NTR chimera panels within the measurement error: y=−3.80x+44.0 for BVDV-non-CP7-HCV 5 NTR chimera, and y=−3.82x+44.3 for OptiQuant HCV. The slopes of the two calibrators showed approximately equivalent PCR efficiencies: 87% for the BVDV-non-CP7-HCV 5 NTR chimera calibrator and 86% for the OptiQuant HCV calibrator. The coefficients of determination indicated a high degree of linearity: 0.98 for HCV-BVDV, and 0.99 for the OptiQuant HCV calibrator. The use of BVDV-non-CP7-HCV 5 NTRchimeric calibrator gave equivalent data compared to a known HCV calibrator that closely resembles patient samples, such as the AcroMetrix OptiQuant HCV panel.

EXAMPLE 12

Use of BVDV-non-CP7-HCV 5'NTR Chimera as an Internal Quantification Standard (QS)

In this experiment the HCV signal generated with the BVDV-non-CP7-HCV 5 NTR chimera functioned as QS for a quantitative West Nile Virus (WNV) assay. Four replicates of a WNV panel at 1E6, 1E5, 1E4, and 1E3 copies/ml were extracted using the Qiagen QIAcube with the Qiagen QIAamp MinElute Virus Spin Kit. 19.4 µl of BVDV at a concentration of 1E4 IU/ml was added as an internal quantification standard (QS) to the carrier RNA solution following the MinElute sample extraction protocol. 12.34 µl of the RNA eluate was amplified using WNV assay reagents, which also contained HCV-5'NTR primers and probes. The PCR reaction was run on an Applied Biosystems, ABI PRISM 7300. The data were analyzed using the Applied Biosystems Sequence Detection Software version 1.4.

The results of the linear regression analysis are shown in FIG. 13. A slope of 2.891 and a coefficient of determination of 0.996 was obtained from the equation of the line.

This experiment demonstrated usefulness of a BVDV chimera as an internal Quantification Standard (QS) in a quantitative NAT assay. The calibration curve for a quantitative WNV assay was generated by subtracting the WNV Ct value from the QS (BVDV-non-CP7-HCV 5 NTR) Ct and plotting the difference in Ct against the known WNV concentration in copies/mL (cp/mL).

EXAMPLE 12

Generation of a cDNA or Plasmid from Purified Chimeric Pesitvirus RNA

Donis and Vassilev described in U.S. Pat. No. 6,001,613 the generation of plasmid containing the cDNA of BVDV and producing infectious BVDV. The same methods and more recent methods known in the art can be used to purify viral RNA from the pestivirus-chimera and use the purified RNA to generate cDNA of this chimera. The cDNA can be cloned into a plasmid. The cDNA or plasmid would be useful as the starting point for generating new virus as described in Examples 3 and 4.

What is claimed is:

1. A chimeric viral RNA sequence comprising: first virus RNA sequence from *Pestivirus*, and second RNA sequence inserted within a variable region of a 3' non translated region between a $SL_{STOP}$ stem-loop structure and a SLII stem-loop structure in the 3' non translated region, NTR, of the first *Pestivirus* RNA sequence, wherein the chimeric viral RNA sequence is stable in RNA replication and forms a ribonuclease resistant viral particle, and wherein the first virus RNA sequence is from a bovine viral diarrhea virus (BVDV).

2. The chimeric RNA viral sequence of claim 1, wherein the first virus RNA sequence is from a non-CP7 clone of the bovine viral diarrhea virus (BVDV).

3. The chimeric RNA viral sequence of claim 1, wherein the second RNA sequence is inserted between a $UGA_{pos.cons.}$ box and the SLII stem-loop structure in the 3'V of the 3' non translated region, NTR.

4. The chimeric RNA viral sequence of claim 1, wherein the second RNA sequence is a portion of an Hepatitis C Virus, HCV, virus.

5. The chimeric RNA viral sequence of claim 4, wherein the portion of the Hepatitis C Virus, HCV, virus is comprised of at least 8 nucleotides.

6. The chimeric RNA viral sequence of claim 4, wherein the second RNA sequence is a 5' non translated region, NTR, region of the Hepatitis C Virus, HCV virus.

7. The chimeric RNA viral sequence of claim 1, wherein the second RNA sequence is a multiplex sequence comprising sequences from more than one RNA virus.

8. The chimeric RNA viral sequence of claim 1, wherein the second RNA sequence is selected from the group consisting of Hepatitis C Virus (HCV), Hepatitis C Virus (HCV) genotypes 1-7, Human Immunodeficiency Virus (HIV), Human Immunodeficiency Virus-1 (HIV-1), Human Immunodeficiency Virus-2 (HIV-2), Human T-lymphotrophic Virus-1 (HTLV-1), Human T-lymphotrophic Virus-2 (HTLV-2), hepatitis G, an enterovirus, a respiratory virus and a blood borne virus.

9. A vector comprising: DNA sequence of a chimeric viral RNA sequence comprising: vector DNA sequence, a first DNA sequence complementary to a first *Pestivirus* RNA sequence, and a second DNA sequence complementary to a second RNA sequence, wherein the second RNA sequence is inserted within a variable region of a 3' non translated region between a $SL_{STOP}$ stem-loop structure and a SLII stem-loop structure in the 3' non translated region, NTR, of the first *Pestivirus* RNA sequence, and wherein the sequence of a chimeric RNA virus generated by transcription of the DNA vector is stable in replication, and forms a RNase resistant viral particle, and wherein the first virus RNA sequence is from a bovine viral diarrhea virus (BVDV).

10. The chimeric RNA viral sequence of claim 9, wherein the second RNA sequence is at least a portion of an Hepatitis C Virus, HCV, virus.

11. The chimeric RNA viral sequence of claim 10, wherein the second RNA sequence is at least 8 nucleotides of the Hepatitis C Virus, HCV, virus.

12. The chimeric RNA viral sequence of claim 10, wherein the second RNA sequence is from a 5' non translated region, NTR, region of the Hepatitis C Virus, HCV, virus.

13. A culture of cells containing RNA virus comprising: host cell harboring chimeric first and second RNA virus sequence, wherein the first RNA virus is *Pestivirus* and a second RNA sequence is inserted in a variable region of a 3' non translated region between a $SL_{STOP}$ stem-loop structure and a SLII stem-loop structure in the 3' non translated region, NTR, of the first *Pestivirus* RNA sequence, wherein the chimeric RNA viral sequence is stable in RNA replication, and ribonuclease resistant viral particles comprising the first and second RNA virus sequences when cultured, and wherein the first virus RNA sequence is from a bovine viral diarrhea virus (BVDV).

14. The culture of claim 13, wherein the second RNA sequence is from an Hepatitis C Virus, HCV, virus.

15. The culture of claim 14, wherein the second RNA sequence is at least 8 nucleotides of the Hepatitis C Virus, HCV, virus.

16. The culture of claim 14, wherein the second RNA sequence is from a 5' non translated region, NTR, region of the Hepatitis C Virus, HCV, virus.

17. The culture of claim 13, wherein the viral particles are infectious.

18. The culture of claim 13, wherein the viral particles are non-infectious.

* * * * *

SEQUENCE LISTING

```
<160> NUMBER OF SEQ ID NOS: 33

<210> SEQ ID NO 1
<211> LENGTH: 12267
<212> TYPE: DNA
<213> ORGANISM: Pestivirus type 1
<220> FEATURE:
<221> NAME/KEY: misc_feature
<223> OTHER INFORMATION: BVDV-non-CP7

<400> SEQUENCE: 1
gtatacgagg ttaggcaagt tctcgtatac atattggaca ctctaaaaat aattaggcct      60
aggggacaaa aatcctcctt agcgaaggcc gaaaagaggc taaccatgcc cttagtagga    120
ctagcaaaat aaggggggta gcaacagtgg cgagttcgtt ggatggctga agccctgagt    180
acagggtagt cgtcagtggt tcgacgcttt ggaggacaag cctcgagatg ccacgtggac    240
gagggcatgc ccacagcaca tcttaacctg dacagggtc gttcaggtga aaacggttta    300
accaaccgct acgaatacag tctgatagga tgctgcagag gcccactgta ttgctactga    360
aaatctctgc tgtacatggc acatggagtt gatcacaaat gaacttttat acaaaacata    420
caaacaaaaa cccgctggag tggaggaacc agtatacgac caagctggta acccttttgtt   480 tggagaaaga ggagtgattc atccgcagtc aacgctaaaa cttccacata aaagagggga    540
gcgtgaagtc cccaccaatc tggcttcttt accaaaaaga ggtgactgca ggtcgggtaa    600
cagcaagggg cctgtgagtg gaatctactt aaaaccaggg ccgttattct accaagatta    660
taaaggacct gtctatcata gagccccatt ggagtttttt gaggaggcgt ctatgtgtga    720
gacaactaaa agaatagdga gagtaactgg tagtgacagc agattatacc acatttacgt    780
```

```
gtgtattgat gggtgcataa tagtcaagag tgctacaaaa gaccgccaga aagtactcaa    840
gtgggtccac aacaagctaa actgccccct atgggtttca agctgctccg acacaaaaga    900
tgaaggggtg gtgaggaaga agcaacaaaa gccagatagg ttggaaaagg ggagaatgaa    960
gataacacct aaggagtcag agaaagacag taagaccaag ccgccagatg ctacgatagt   1020
ggtagatgga gtcaagtatc aggtaaagaa aaaggaaaa gtcaagagca agaacaccca   1080
ggacggctta taccacaaca aaataaaacc tcaagagtcg cgcaagaaac tagagaaagc   1140
cctattggcc tgggcaataa tagccctggt tttctttcaa gtcacaatgg gagagaacat   1200
aacgcaatgg aacttacaag ataatggaac ggaaggcata caacgagcca tgtttcaaag   1260
aggagtgaat agaagtttac atgggatctg gccagagaaa atctgtacag gtgttccttc   1320
ccacctggcc actgacacag aattgaaggc aattcatggt atgatggatg caagtgagaa   1380
gacaaattat acgtgctgca gactccaacg ccatgaatgg aacaaacatg gttggtgcaa   1440
ctggtacaac attgaacctt ggatcctcct tatgaataaa actcaggcca accttactga   1500
gggtcagcca ctaagggagt gtgccgtcac atgccgggtat gatcgagata gtgacctgaa   1560
tgtagtaaca caagccaggg atagccccac accattaaca ggttgcaaga aaggcaaaaa   1620
cttttccttt gcaggcatat tggtacaagg gccttgcaac tttgaaatag ccgtaagtga   1680
tgtgctgttc aaagagcatg attgcactag tgtgattcaa gacacagctc actacctcgt   1740
agacgggatg accaactccc tagagagtgc caggcaaggg accgcgaaac taacaacttg   1800
gctgggcagg cagcttggga tactaggaaa gaaactggaa aacaagagta agacatggtt   1860
tgggcatat gcagcctctc cctattgtga ggtagaacgg aagcttggtt acatctggta   1920
tacaaagaat tgcactccag cctgtttgcc taggaataca aagatcatcg gccccggtag   1980
gtttgacacc aatgccgagg atggtaaaat actgcatgag atgggggtc acttgtcgga   2040
ggtgctacta ctctcagtgg tagtgctgtc cgatttcgct ccagagacag ccagtgtgat   2100
atacttgatt cttcatttct ccatcccaca aggacacact gatatacaag attgtgacaa   2160
aaaccaacta aacctcaccg tagaactcac aacagcagaa gtaataccag gctcagtttg   2220
gaacttgggt aaatatgttt gtgtaagacc agattggtgg cctatgagaa cagccacagt   2280
cctggtgatt gaagaggtgg gtcaagtaat taaggttgtc ttaagggcgt taaaagatct   2340
gacgcgcatt tggaccgctg ctacaaccac tgcattcttg gtttgtctgg tgaaggtagt   2400
gagaggccaa gtgttacaag gtatactgtg gctgatgctc ataacagggg cgcaagggta   2460
cccagactgc aaacccggct tttcatacgc catagccaaa aatgatgaga ttggcccact   2520
tggagctaca ggcctcacca ctcagtggta cgaatactcg gatgggatgc ggctgcagga   2580
ctcagtagtt gaagtttggt gtaaaaatgg agagatcaaa tatctaatca gatgcgggag   2640
ggaagccagg tatctggctg ttctacacac gagagccttg ccgacatctg tagtatttga   2700
aaaattttt gatgggaaag aacaagagga catagtagaa atggatgaca actttgaatt   2760
cggtctttgc ccgtgtgatg ctagacccct gataagggga aaatttaata caacacttct   2820
aaatgggcca gccttccaga tggtttgccc tataggatgg acagggactg taagctgtac   2880
actggccaat aaggatacgt tagccacaat cgttgtgaga acgtataaga gggtcaggcc   2940
ttttccatat aggcaggact gtgtcaccca gaaaaccatc ggggaagacc tctacgactg   3000
tgccttagga gggaattgga cttgtgtgcc ggggatgca ctacgatatg tagctgggcc   3060
cgttgagtct tgtgagtggt gtggttacaa gttttaaaaa agtgagggtc tgccgcattt   3120
cccaatcggc aaatgcaggc tgaagaatga gagtggctat agacaagtgg atgagacttc   3180
```

```
ttgcaacaga aacggcgtgg ctatagtgcc atctggcacg gtcaaatgca agatagggga   3240
cacggtggtg caagtcattg caatggatga taaactaggg cctatgcctt gcaaaccaca   3300
tgaaatcata tccagtgagg ggccagtgga aaagacggca tgcaccttca actacacaag   3360
aacattaaaa aacaagtact ttgagcccag ggataactat tttcaacaat acatgttaaa   3420
gggggagtac caatattggt ttgacctaga gatcactgac caccaccgag attacttcgc   3480
tgagtccctg ttggtgatag tagttgcact cctgggtggc aggtacgtgc tttggctgct   3540
ggtcacatac atgatcttat cagaacagat ggcctcgggt gtccagtatg ggcaggtga   3600
aatagtgatg atgggcaact tgttaacaca tgacagtgtt gaagtggtga catatttctt   3660
actactatac ctactactaa gagaggaaaa caccaaaaaa tgggtcatac ttatatacca   3720
catcatagta atgcatcctc taaaatcggt gacggtgata ttgctaatgg ttgggggat   3780
ggcaaaggct gaaccaggtg cccaggggta cctagagcag gtagacctta gttttacgat   3840
gattacgatc atcgtaatag gtctggttat agctaggcgt gatcccactg tggtgccact   3900
agtcactata gtcgcggcac tgaagatcac aggactaggc tttgggcccg gagtggatgc   3960
agctatggca gttctcacct taaccctact gatgactagt tatgtgacag actacttcag   4020
gtataaaagg tggatacaat gtatcctcag cttagtagcc ggggtgttcc ttatccggac   4080
cctcaaacat ctaggtgaac tcaaaacccc tgagctgacc ataccaaatt ggaggccact   4140
aaccttcata ctattatacc tgacttcagc aacagttgtt acaagatgga aaattgatat   4200
agctggcata ttcctgcaag gggccctat cctttgatg atcgccaccc tatgggctga   4260
cttcttgact cttgttctga tcctacccac ctacgaatta gccaagctgt actacctaaa   4320
gaacgtcaag actgacgtgg agaagagttg gctgggggg ttagactaca ggacaattga   4380
ctctgtctat gatgtggatg aaagtggaga aggcgtgtac ctcttcccgt ccagacagaa   4440
gaaaaataag aatatcagca tactcttgcc cctcatcaga gctacgctaa taagttgtat   4500
tagcagcaaa tggcagatgg tgtatatggc ttacttaacc ctggactta tgtactacat   4560
gcacagaaag gttattgaag agatatcagg gagtaccaat gtgatgtcta gagtgatagc   4620
agcacttata gaattaaact ggtccatgga agaagaagag agcaagggct taaagaagtt   4680
ttttatacta tctggaaggt tgaggaacct tataataaag cataaggtta ggaaccagac   4740
tgtggcaagc tggtatgggg aggaagaagt ctacggcatg ccaaaagtcg taaccataat   4800
aagggcctgc acgctaaaca agaacaaaca ttgcataata tgcacagtat gtgaggctag   4860
aaaagtggaag ggaggcaact gccctaaatg cggccgccac gggaagccca tcatttgtgg   4920
gatgactcta gcggattttg aagaaggca ctacaagaga atttttataa gggaaggtaa   4980
cttttgaagga ccccttcaggc aggaatacaa tgggtttgta caatacaccg ctagggggca   5040
attgttcctg agaaatttac ccatattggc aaccaaagta aaaatgatca tggtaggcaa   5100
cctaggagag gaaatcggtg atctagaaca cctaggatgg atcctaaggg gacctgccgt   5160
gtgcaagaaa ataactgagc acgaaaaatg ccatgtcaac atactggaca agctgactgc   5220
gttttttgga gttatgccaa gagggactac accaagggct ccggtgagat tcccaacagc   5280
actactaaag gtaaggaggg gattggaaac cggttgggct tacacgcatc aaggtggcat   5340
aagctcagta gaccatgtga ccgctggcaa ggatctattg gtttgtgaca gtatgggtag   5400
aactagagtg gtttgccaaa gcaacaacaa gttaactgat gagacagaat atggtgtcaa   5460
gacggactcc ggatgtccag atggtgccag atgctatgta ttaaacccag aggcagtaaa   5520
```

-continued

```
tatatcaggg tccaagggag ctgtcgtaca cctccaaaaa acgggtgggg aatttacatg      5580
tgttactgca tcaggtacac cggccttctt cgacctgaaa aatttgaaag gatggtcggg      5640
tctacccata tttgaagcct ccagcggcag agtggttggc agagtcaaag tgggaaagaa      5700
tgaggaatcc aaacccacaa aattaatgag tggtatccaa actgtttcta aaaatacggc      5760
cgatttaaca gaaatggtca agaagataac cagcatgaac agggggact ttaggcagat       5820 aacccttgca acaggggcag ggaagaccac tgagctccca aaagcagtga tagaggagat      5880
aggacgacac aaacgggtac tagtgctcat accattaaga gcagcagctg agtcagtcta     5940
tcaatacatg agattgaaac acccaagtat ctcctttaac ctgagaatag gggacatgaa      6000
agaaggggat atggcaaccg ggatcaccta cgcctcatat ggatatttt gccaaatgcc       6060 acaaccaaag ctcagagcag caatgataga gtattcatac atatttctgg atgagtatca      6120
ctgcgctact cctgagcagt tggctgttat aggaaaaatt cacagatttt ctgagagcat      6180
aagagtggtt gccatgactg ccaccccagc agggtcagta accacaacag ggcaaaaaca      6240
cccaatagaa gaattcatag cccctgaggt gatgaaaggg gaggaccttg gaagccagtt      6300
ccttgacata gcggggttaa agatccctgt agaggagatg aagggtaaca tgttggtttt      6360
cgtgcccacg aggaacatgg cagttgaagt agccaagaaa ctaaaagcca agggctacaa      6420
ctcagggtat tactcagtg ggaagaccc agctaacttg agagtggtaa catcacagtc        6480
cccatacgtc gtggtagcca ctaatgccat cgagtcaggg gtaacgctgc cagatttaga     6540
tacagttgtt gacacaggtc tgaaatgtga agagggtg agggtgtctt ccaaaatacc        6600
ctttatagta acaggcctta agagaatggc tgtcactgtg ggcgaacagg ctcagcggag      6660
aggcagggta ggtagagtga aacccggtag gtattataga agtcaggaaa cagcaaccgg      6720
gtcaaaggac taccactatg acttgttaca ggcacagagg tacgggatcg aagatgggat      6780
caacgtaaca aagtccttta gggagatgaa ttatgactgg agcctgtatg aggaagacag      6840
cttgctgata acccagctgg agatactgaa caatctactc atctctgaag atttaccagc      6900
agctgttaaa acatcatgg caagaactga tcacccagag cctatccagc ttgcatataa       6960
cagttatgag gtccaagtcc ctgtgctgtt cccaaaaata aggaatgggg aggtcacaga      7020
cacttacgag aactactcat tcctaaatgc aaggaaacta ggggaagacg tgcccgtgta     7080
cgtttatgcc accgaagatg aagatctggc tgtggacctt ctaggcttgg actggccaga     7140
cccagggaat cagcaagtag tggagactgg gaaggcactg aagcaagtgg taggactgtc     7200
ctctgccgaa aatgccttgc tcatagccct atttgggtat gtaggatacc aagccttgtc    7260
aaaaagacac gtcccaatga tcacagacat atacactata aagatcaaa gactagagga      7320 cacaacccac cttcaatatg cgcccaatgc cataagaact gaggggaagg agactgaact     7380
aaaggaatta gcagtgggtg acttggacaa aatcatgggt tccatctcgg actatgcatc    7440
agagggattg aatttcgtaa ggtcccaagc agaaagatg agatctgccc ccgctttcaa      7500
agaaaacgtg gaagctgcta aagggtacgt ccaaaagttt attgattctc tcatagaaaa     7560
taaagaaacc ataatcagat atggcctgtg gggaacacac acggcactct acaagagtat     7620
tgccgcgaga ttgggtcatg aaactgcatt cgctacacta gtgataaagt ggctggcctt     7680 cggggggtgag tcggtgtcag accacatgag acaagcagct gtcgacctgg ttgtttatta   7740
tgtgatcaat aagccctcct tcccagggga ttctgaaacc caacaggaag gaaggcgatt   7800
cgtcgccagc ctgttcatct ccgctttggc aacctacaca tacaaaactt ggaattacaa    7860
caacctctcc aaggtagtag aaccagcctt agcatacctc ccctatgcta ccaatgcact    7920
```

```
aaaaatgttt accccgacca gactggagag cgtagttata cttagtacca caatatacaa   7980
aacttacctc tcaataagga agggaaagag tgatggactg ttgggtacag ggatcagtgc   8040
agcaatggag attctatcac agaacccagt gtcggtaggt atatctgtca tgctgggggt   8100
gggggcgatt gccgcgcaca atgccattga gtctagtgaa caaaaaagga ccctgttgat   8160
gaaagtgttt gtaaaaaact tcctggacca ggcggcaaca gatgagctgg taaaggaaaa   8220
cccagagaaa ataataatgg ccctatttga agcagtccag acaattggca accccttgag   8280
gctcatatat cacctgtatg gggtttacta caaaggctgg gaagcaaaag aactatcaga   8340
gagaacagca ggcaggaacc tgttcacctt gataatgttc gaagccttcg aactactagg   8400
gatggactct gaagggaaga taaggaacct gtctgggaat tatgtcctgg atttgatcta   8460
cagcctacat aaacagataa atagaggctt gaaaaaaata gtcttggggt gggctcccgc   8520
accatttagt tgcgactgga ctcctagtga tgagagaatt aggttaccca caaacaacta   8580
tctaagagta gaaactaagt gtccatgtgg ctatgagatg aaagcactaa ggaacgttgg   8640
tggcagtctt accaaagtgg aggagaaagg acctttctc tgcaggaaca ggcttggtag   8700
agggccggtc aactatagag tcacaaagta ctatgatgac aacctcaaag agataaaacc   8760
agttgctaaa ctagaaggat tgtggatca ctattacaaa ggtgttacag caaggataga   8820
ttatggcaga gggaaaatgc tattagctac tgataaatgg gaggtggagc acggtgttgt   8880
cactaggttg gcaaagagat ataccggagt tggattcaag ggagcatacc tgggtgatga   8940
acccaaccac cgcgacctag tagaaagaga ctgtgcaact ataacaaaaa atacagtgca   9000 gttttttaaaa atgaagaaag gctgtgcatt tacctatgac ttaaccctgt ccaatttaac   9060
caggttaatt gaattggtac acaaaaataa cctagaagag aaagacatac cagcagccac   9120
agtaacgaca tggctggctt atactttgt aaatgaagat attgggacta taaaaccagt   9180
actaggagag agagtggtca ccgacccagt ggtggatgtt aacttacaac agaagtaca   9240 agtggataca tcagaggttg ggatcacttt agttggtagg gcagccttaa tgacgacagg   9300
tactacaccc gtagtcgaaa aaacagagcc caatgctgat ggtggtccaa gctccataaa   9360
gattgggttg gatgaaggaa gatacccagg acctggactg caagaccgca ccttgaccga   9420
tgaaatacat tctagggatg aaaggccctt tgttctagtc ctgggctcaa aaaattctat   9480
gtcaaataga gctaaaactg ctagaaacat caacttatac aagggaata accccaggga   9540 gattagagat ctgatggcac aggggcgtat gctagttgtg gccttaaagg attttaaccc   9600
tgagttgtct gaactagttg atttcaaggg actttcctta gacagggaag ccttggaagc   9660
tctcagcctg gggcggccaa agtccaagca ggtgaccaca gccacagtta gggagttatt   9720
agagcaggag gtacaagttg agatcccag ttggtttgga gcaggtgatc cagtcttctt   9780
ggaagtgact ttgaagggtg acagatatca cttagtagga gatgtagata gagtgaaaga   9840
tcaagcgaag gagcttgggg ccacggacca gacaagaata gtgaaggaag tgggtgcaag   9900
aacctatacc atgaagctgt ctagttggtt tcttcaggca acaaataaac agatgagctt   9960 gacccctta tttgaggagc tattgctacg ttgccccccct aaaataaaga gcaataaagg  10020
gcacatggca tcagcttacc aactagcaca gggaaactgg agcccccttg actgtggagt  10080
tcacctgggc accatacctg ccaggagggt aaaaatccac ccatatgaag cttacctgaa  10140
actgaaggat ttattggaag aagaagaaaa gaaaccaaag tgtagagaca cagtaataag  10200
agaacacaac aagtggatcc tcaaaaaagt gaggcaccag ggtaatctca atacaaagaa  10260
```

| | | | | | |
|---|---|---|---|---|---|
| aatcctcaac | cctggaaagc | tatcagaaca | gctagataga | gaagggcata | aagaaacat 10320 |
| ttataacaat | cagattggca | ccataatgac | ggaagcagga | agtaggttgg | aaaaattacc 10380 |
| agtcgtcaga | gcccaaactg | acactaaaag | cttccatgag | gcaatcagag | ataagataga 10440 |
| caagaatgaa | aatcagcaga | gcccaggact | gcatgataaa | ttgttagaga | tctttcatac 10500 |
| aatagcccaa | cccagcctaa | gacacaccta | cagtgacgtg | acgtgggagc | aacttgaggc 10560 |
| aggggttaat | agaaaggggg | ctgctggctt | tctagagaag | aagaatgttg | agaagtact 10620 |
| ggactcagag | aagcacctgg | tggaacaact | gatcagagat | ttgaaaacag | gaaggaagat 10680 |
| aagatattat | gagacagcaa | taccaaaaaa | tgaagagaa | gatgtcagtg | atgattggca 10740 |
| atcaggggac | ttagtagatg | agaagaaacc | aagggtgatt | caataccctg | aagctaaaac 10800 |
| aagactagcc | atcactaaag | taatgtacaa | ctgggtgaaa | cagcagcccg | tcgtgatccc 10860 |
| agggtatgaa | gggaagaccc | cattatttaa | cattttcaac | aaggtgagga | aggaatggga 10920 |
| tttgttcaat | gaaccagtag | ctgtgagttt | cgacactaag | gcttgggaca | cccaagtaac 10980 |
| tagtagagat | ctacggctta | ttggtgaaat | tcaaaaatat | tactacagga | aagagtggca 11040 |
| caaattcatc | gataccatta | ctgaccatat | ggtggaggtg | cccgtcataa | cggcagatgg 11100 |
| tgaggtatac | ataagaaatg | gacaaagggg | tagtggccag | ccagacacaa | gtgcaggcaa 11160 |
| tagcatgcta | aacgtgttaa | caatgatgta | tgccttctgt | gaaagtacgg | gggttccata 11220 |
| caagagtttc | aataggggttg | caaggatcca | tgtctgtggg | gatgacggct | tcctaataac 11280 |
| agagaagggg | ctgggattaa | agtttgccaa | caatgggatg | caaattctgc | acgaagcagg 11340 |
| caagcctcaa | aagataactg | agggggaaag | aatgaaagtt | gcctataggt | tcgaggacat 11400 |
| agaattctgc | tctcatacac | cagtccccgt | taggtggtct | gataacacca | gcagttacat 11460 |
| ggccggcaga | gacactgccg | ttatattatc | aaagatggca | acaagattgg | attcaagtgg 11520 |
| agaaaggggt | actatagcat | atgaaaaagc | agtggccttt | agttttttgc | tgatgtactc 11580 |
| ctggaatcct | cttgtgagga | ggatctgtct | actggtcctt | tcacagcagc | cagagacaac 11640 |
| tccatcaacc | cagaccactt | actattataa | aggagaccca | ataggagcct | acaaagatgt 11700 |
| aataggtaag | aatttgtgtg | aattaaaaag | gacgggtttt | gaaaaattgg | ccaatttaaa 11760 |
| cctaagcctg | tccacgttag | gaatctggtc | caaacataca | agtaaaagaa | tcatccaaga 11820 |
| ctgtgtaacc | atcgggaaag | aggaaggcaa | ttggctggtc | aatgccgaca | ggttgatatc 11880 |
| tagcaaaact | ggccatttgt | acatacctga | caaaggttat | acattacaag | ggaaacatta 11940 |
| tgaacaactt | caactgcagg | caagaactag | cccagtcacg | ggagtaggga | cggagagata 12000 |
| taaactaggc | cctatagtaa | acctgctgct | gaggaggttg | agagttctgc | ttatggcagc 12060 |
| tgtcggtgcc | agcagttgaa | ataatgtatg | tatatattgt | atataaatct | gtatttgtat 12120 |
| atattatgtt | taaatttagt | tgagattagt | agtgatatat | agttatctac | ctcaagctaa 12180 |
| cactacactc | aatgcacaca | gcactttagc | tgtatgaggg | tacacccgac | gtccacggtt 12240 |
| ggactaggga | aaacccttaa | cagcccc | | | 12267 |

<210> SEQ ID NO 2
<211> LENGTH: 341
<212> TYPE: DNA
<213> ORGANISM: Hepatitis C virus
<220> FEATURE:
<221> NAME/KEY: misc_feature
<223> OTHER INFORMATION: HCV 5' NTR

<400> SEQUENCE: 2

```
gccagccccc gattggggc gacactccac catagatcac tccctgtga ggaactactg      60 tcttcacgca gaaagcgtct agccatggcg ttagtatgag tgtcgtgcag cctccaggac     120 ccccctctc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgcctcggg aggtctcgta gaccgtgcac c                        341

<210> SEQ ID NO 3
<211> LENGTH: 12625
<212> TYPE: DNA
<213> ORGANISM: Pestivirus type 1
<220> FEATURE:
<221> NAME/KEY: misc_feature
<223> OTHER INFORMATION: BVDV non-CP7-HCV 5'NTR chimera

<400> SEQUENCE: 3
gtatacgagg ttaggcaagt tctcgtatac atattggaca ctctaaaaat aattaggcct      60
aggggacaaa atcctccttt agcgaaggcc gaaaagaggc taaccatgcc cttagtagga    120
ctagcaaaat aaggggggta gcaacagtgg cgagttcgtt ggatggctga agccctgagt    180
acagggtagt cgtcagtggt tcgacgcttt ggaggacaag cctcgagatg ccacgtggac    240
gagggcatgc ccacagcaca tcttaacctg gacaggggtc gttcaggtga aacggttta    300 accaaccgct acgaatacag tctgatagga tgctgcagag gcccactgta ttgctactga    360
aaatctctgc tgtacatggc acatggagtt gatcacaaat gaactttat acaaaacata    420 caaacaaaaa cccgctggag tggaggaacc agtatacgac caagctggta accctttgtt    480
tggagaaaga ggagtgattc atccgcagtc aacgctaaaa cttccacata aagaggggga    540
gcgtgaagtc cccaccaatc tggcttcttt accaaaaaga ggtgactgca ggtcgggtaa    600
cagcaagggg cctgtgagtg aatctactt aaaaccaggg ccgttattct accaagatta    660
taaaggacct gtctatcata gagccccatt ggagttttt gaggaggcgt ctatgtgtga    720
gacaactaaa agaatagggga gagtaactgg tagtgacagc agattatacc acatttacgt    780
gtgtattgat gggtgcataa tagtcaagag tgctacaaaa gaccgccaga aagtactcaa    840
gtgggtccac aacaagctaa actgccccct atgggtttca agctgctccg acacaaaaga    900
tgaaggggtg gtgaggaaga agcaacaaaa gccagatagg ttggaaaagg ggagaatgaa    960
gataacacct aaggagtcag agaaagacag taagaccaag ccgccagatg ctacgatagt   1020
ggtagatgga gtcaagtatc aggtaaagaa aaaggaaaa gtcaagagca agaacaccca   1080
ggacggctta taccacaaca aaaataaacc tcaagagtcg cgcaagaaac tagagaaagc   1140
cctattggcc tggcaataa tagccctggt tttctttcaa gtcacaatgg gagagaacat   1200
aacgcaatgg aacttacaag ataatggaac ggaaggcata caacgagcca tgtttcaaag   1260
aggagtgaat agaagtttac atgggatctg gccagagaaa atctgtacag tgttccttc    1320 ccacctggcc actgacacag aattgaaggc aattcatggt atgatggatg caagtgagaa   1380
gacaaattat acgtgctgca gactccaacg ccatgaatgg aacaaacatg gttggtgcaa   1440
ctggtacaac attgaacctt ggatcctcct tatgaataaa actcaggcca accttactga   1500
gggtcagcca ctaagggagt gtgccgtcac atgccggtat gatcgagata gtgacctgaa   1560
tgtagtaaca caagccaggg atagccccac accattaaca ggttgcaaga aaggcaaaaa   1620 ctttttccttt gcaggcatat tggtacaagg gccttgcaac tttgaaatag ccgtaagtga   1680
```

```
tgtgctgttc aaagagcatg attgcactag tgtgattcaa gacacagctc actacctcgt    1740
agacgggatg accaactccc tagagagtgc caggcaaggg accgcgaaac taacaacttg    1800
gctgggcagg cagcttggga tactaggaaa gaaactggaa aacaagagta agacatggtt    1860
tggggcatat gcagcctctc cctattgtga ggtagaacgg aagcttggtt acatctggta    1920
tacaaagaat tgcactccag cctgtttgcc taggaataca aagatcatcg gccccggtag    1980
gtttgacacc aatgccgagg atggtaaaat actgcatgag atggggggtc acttgtcgga    2040
ggtgctacta ctctcagtgg tagtgctgtc cgatttcgct ccagagacag ccagtgtgat    2100
atacttgatt cttcatttct ccatcccaca aggacacact gatatacaag attgtgacaa    2160
aaaccaacta aacctcaccg tagaactcac aacagcagaa gtaataccag gctcagtttg    2220
gaacttgggt aaatatgttt gtgtaagacc agattggtgg ccttatgaga cagccacagt    2280
cctggtgatt gaagaggtgg gtcaagtaat taaggttgtc ttaagggcgt taaaagatct    2340
gacgcgcatt tggaccgctg ctacaaccac tgcattcttg gtttgtctgg tgaaggtagt    2400
gagaggccaa gtgttacaag gtatactgtg gctgatgctc ataacagggg cgcaagggta    2460
cccagactgc aaacccggct tttcatacgc catagccaaa aatgatgaga ttggcccact    2520
tggagctaca ggcctcacca ctcagtggta cgaatactcg gatgggatgc ggctgcagga    2580
ctcagtagtt gaagtttggt gtaaaaatgg agagatcaaa tatctaatca gatgcgggag    2640
ggaagccagg tatctggctg ttctacacac gagagccttg ccgacatctg tagtatttga    2700
aaaaatttt gatgggaaag aacaagagga catagtagaa atggatgaca actttgaatt    2760
cggtcttgc ccgtgtgatg ctagacccct gataagggga aaatttaata caacacttct    2820
aaatgggcca gccttccaga tggtttgccc tataggatgg acagggactg taagctgtac    2880
actggccaat aaggatacgt tagccacaat cgttgtgaga acgtataaga gggtcaggcc    2940
ttttccatat aggcaggact gtgtcaccca gaaaaccatc ggggaagacc tctacgactg    3000
tgccttagga gggaattgga cttgtgtgcc ggggatgca ctacgatatg tagctgggcc    3060
cgttgagtct tgtgagtggt gtggttacaa gttttttaaaa agtgagggtc tgccgcattt    3120
cccaatcggc aaatgcaggc tgaagaatga gagtggctat agacaagtgg atgagacttc    3180
ttgcaacaga acggcgtgg ctatagtgcc atctggcacg gtcaaatgca agataggga    3240
cacggtggtg caagtcattg caatggatga taaactaggg cctatgcctt gcaaaccaca    3300
tgaaatcata tccagtgagg ggccagtgga aaagacggca tgcaccttca actacacaag    3360
aacattaaaa aacaagtact ttgagcccag ggataactat tttcaacaat acatgttaaa    3420
gggggagtac caatattggt ttgacctaga gatcactgac caccaccgag attacttcgc    3480
tgagtccctg ttggtgatag tagttgcact cctgggtggc aggtacgtgc tttggctgct    3540
ggtcacatac atgatcttat cagaacagat ggcctcgggt gtccagtatg gggcaggtga    3600
aatagtgatg atgggcaact tgttaacaca tgacagtgtt gaagtggtga catatttctt    3660
actactatac ctactactaa gagaggaaaa caccaaaaaa tgggtcatac ttatatacca    3720
catcatagta atgcatcctc taaaatcggt gacggtgata ttgctaatgg ttggggggat    3780
ggcaaaggct gaaccaggtg cccaggggta cctagagcag gtagacctta gtttttacgat    3840
gattacgatc atcgtaatag gtctggttat agctaggcgt gatcccactg tggtgccact    3900
agtcactata gtcgcggcac tgaagatcac aggactaggc tttgggcccg gagtggatgc    3960
agctatggca gttctcacct taacccctact gatgactagt tatgtgacag actacttcag    4020
gtataaaagg tggatacaat gtatcctcag cttagtagcc ggggtgttcc ttatccggac    4080
```

```
cctcaaacat ctaggtgaac tcaaaacccc tgagctgacc ataccaaatt ggaggccact    4140
aaccttcata ctattatacc tgacttcagc aacagttgtt acaagatgga aaattgatat    4200
agctggcata ttcctgcaag gggccctat ccttttgatg atcgccaccc tatgggctga    4260
cttcttgact cttgttctga tcctacccac ctacgaatta gccaagctgt actacctaaa    4320
gaacgtcaag actgacgtgg agaagagttg gctgggggg ttagactaca ggacaattga    4380
ctctgtctat gatgtggatg aaagtggaga aggcgtgtac ctcttcccgt ccagacagaa    4440
gaaaaataag aatatcagca tactcttgcc cctcatcaga gctacgctaa taagttgtat    4500
tagcagcaaa tggcagatgg tgtatatggc ttacttaacc ctggacttta tgtactacat    4560
gcacagaaag gttattgaag agatatcagg gagtaccaat gtgatgtcta gagtgatagc    4620
agcacttata gaattaaact ggtccatgga agaagaagag agcaagggct taaagaagtt    4680
ttttatacta tctggaaggt tgaggaacct tataataaag cataaggtta ggaaccagac    4740
tgtggcaagc tggtatgggg aggaagaagt ctacggcatg ccaaaagtcg taaccataat    4800
aagggcctgc acgctaaaca agaacaaaca ttgcataata tgcacagtat gtgaggctag    4860
aaagtggaag ggaggcaact gccctaaatg cggccgccac gggaagccca tcatttgtgg    4920
gatgactcta gcggattttg aagaaaggca ctacaagaga attttataa gggaaggtaa    4980 ctttgaagga cccttcaggc aggaatacaa tgggtttgta caatacaccg ctaggggca    5040 attgttcctg agaaatttac ccatattggc aaccaaagta aaatgatca tggtaggcaa    5100 cctaggagag gaaatcggtg atctagaaca cctaggatgg atcctaaggg gacctgccgt    5160
gtgcaagaaa ataactgagc acgaaaaatg ccatgtcaac atactggaca agctgactgc    5220
gttttttgga gttatgccaa gagggactac accaagggct ccggtgagat cccaacagc    5280 actactaaag gtaaggaggg gattggaaac cggttgggct tacacgcatc aaggtggcat    5340
aagctcagta gaccatgtga ccgctggcaa ggatctattg gtttgtgaca gtatgggtag    5400
aactagagtg gtttgccaaa gcaacaacaa gttaactgat gagacagaat atggtgtcaa    5460
gacggactcc ggatgtccag atggtgccag atgctatgta ttaaacccag aggcagtaaa    5520
tatatcaggg tccaagggag ctgtcgtaca cctccaaaaa acgggtgggg aattacatg    5580 tgttactgca tcaggtacac cggccttctt cgacctgaaa aatttgaaag gatggtcggg    5640
tctacccata tttgaagcct ccagcggcag agtggttggc agagtcaaag tgggaaagaa    5700
tgaggaatcc aaacccacaa aattaatgag tggtatccaa actgtttcta aaaatacggc    5760
cgatttaaca gaaatggtca agaagataac cagcatgaac aggggggact ttaggcagat    5820 aaccccttgca acaggggcag ggaagaccac tgagctccca aaagcagtga tagaggagat    5880
aggacgacac aaacgggtac tagtgctcat accattaaga gcagcagctg agtcagtcta    5940
tcaatacatg agattgaaac acccaagtat ctccttaac ctgagaatag gggacatgaa    6000 agaagggat atgcaaccg ggatcaccta cgcctcatat ggatattttt gccaaatgcc    6060
acaaccaaag ctcagagcag caatgataga gtattcatac atatttctgg atgagtatca    6120
ctgcgctact cctgagcagt tggctgttat aggaaaaatt cacagatttt ctgagagcat    6180
aagagtggtt gccatgactg ccacccagc agggtcagta accacaacag gcaaaaaca    6240 cccaatagaa gaattcatag cccctgaggt gatgaaaggg gaggaccttg aagccagtt    6300 ccttgacata gcggggttaa agatccctgt agagagatg aagggtaaca tgttggtttt    6360
cgtgcccacg aggaacatgg cagttgaagt agccaagaaa ctaaaagcca agggctacaa    6420
```

```
ctcagggtat tactacagtg gggaagaccc agctaacttg agagtggtaa catcacagtc    6480
cccatacgtc gtggtagcca ctaatgccat cgagtcaggg gtaacgctgc cagatttaga    6540
tacagttgtt gacacaggtc tgaaatgtga gaagagggtg agggtgtctt ccaaaatacc    6600
ctttatagta acaggcctta agagaatggc tgtcactgtg ggcgaacagg ctcagcggag    6660
aggcagggta ggtagagtga aacccggtag gtattataga agtcaggaaa cagcaaccgg    6720
gtcaaaggac taccactatg acttgttaca ggcacagagg tacggatcg  aagatgggat    6780 caacgtaaca aagtccttta gggagatgaa ttatgactgg agcctgtatg aggaagacag    6840
cttgctgata acccagctgg agatactgaa caatctactc atctctgaag atttaccagc    6900
agctgttaaa aacatcatgg caagaactga tcacccagag cctatccagc ttgcatataa    6960
cagttatgag gtccaagtcc ctgtgctgtt cccaaaaata aggaatgggg aggtcacaga    7020
cacttacgag aactactcat tcctaaatgc aaggaaacta ggggaagacg tgcccgtgta    7080
cgtttatgcc accgaagatg aagatctggc tgtggacctt ctaggcttgg actggccaga    7140
cccagggaat cagcaagtag tggagactgg gaaggcactg aagcaagtgg taggactgtc    7200
ctctgccgaa aatgccttgc tcatagccct atttgggtat gtaggatacc aagccttgtc    7260
aaaaagacac gtcccaatga tcacagacat atacactata gaagatcaaa gactagagga    7320
cacaacccac cttcaatatg cgcccaatgc cataagaact gagggaagg  agactgaact    7380 aaaggaatta gcagtgggtg acttggacaa aatcatgggg tccatctcgg actatgcatc    7440
agagggattg aatttcgtaa ggtcccaagc agaaaagatg agatctgccc ccgctttcaa    7500
agaaaacgtg gaagctgcta aagggtacgt ccaaaagttt attgattctc tcatagaaaa    7560
taaagaaacc ataatcagat atggcctgtg gggaacacac acggcactct acaagagtat    7620
tgccgcgaga ttgggtcatg aaactgcatt cgctacacta gtgataaagt ggctggcctt    7680 cggggggtgag tcggtgtcag accacatgag acaagcagct gtcgacctgg ttgtttatta    7740
tgtgatcaat aagcccctcc tcccagggga ttctgaaacc caacaggaag gaaggcgatt    7800
cgtcgccagc ctgttcatct ccgctttggc aacctacaca tacaaaactt ggaattacaa    7860
caacctctcc aaggtagtag aaccagcctt agcatacctc ccctatgcta ccaatgcact    7920
aaaaatgttt accccgacca gactggagag cgtagttata cttagtacca caatatacaa    7980
aacttacctc tcaataagga agggaaagag tgatggactg ttgggtacag ggatcagtgc    8040
agcaatggag attctatcac agaacccagt gtcggtaggt atatctgtca tgctggggt    8100 gggggcgatt gccgcgcaca atgccattga gtctagtgaa caaaaaagga ccctgttgat    8160
gaaagtgttt gtaaaaaact tcctggacca ggcggcaaca gatgagctgg taaaggaaaa    8220
cccagagaaa ataataatgg ccctatttga agcagtccag acaattggca accccttgag    8280
gctcatatat cacctgtatg gggtttacta caaaggctgg gaagcaaaag aactatcaga    8340
gagaacagca ggcaggaacc tgttcacctt gataatgttc gaagccttcg aactactagg    8400
gatggactct gaagggaaga taaggaacct gtctgggaat tatgtcctgg atttgatcta    8460
cagcctacat aaacagataa atagaggctt gaaaaaaata gtcttgggg  gggctcccgc    8520 accatttagt tgcgactgga ctccagtga  tgagagaatt aggttaccca caaacaacta    8580
tctaagagta gaaactaagt gtccatgtgg ctatgagatg aaagcactaa ggaacgttgg    8640
tggcagtctt accaaagtgg aggagaaagg acctttctc  tgcaggaaca ggcttggtag    8700
agggccggtc aactatagag tcacaaagta ctatgatgac aaccctcaaag agataaaacc    8760 agttgctaaa ctagaaggat tgtggatcca ctattacaaa ggtgttacag caaggataga    8820
```

```
ttatggcaga gggaaaatgc tattagctac tgataaatgg gaggtggagc acggtgttgt   8880
cactaggttg gcaaagagat ataccggagt tggattcaag ggagcatacc tgggtgatga   8940
acccaaccac cgcgacctag tagaaagaga ctgtgcaact ataacaaaaa atacagtgca   9000
gtttttaaaa atgaagaaag gctgtgcatt tacctatgac ttaaccctgt ccaatttaac   9060
caggttaatt gaattggtac acaaaaataa cctagaagag aaagacatac cagcagccac   9120
agtaacgaca tggctggctt atactttgt aaatgaagat attgggacta taaaaccagt    9180
actaggagag agagtggtca ccgacccagt ggtggatgtt aacttacaac cagaagtaca   9240
agtggataca tcagaggttg ggatcacttt agttggtagg gcagccttaa tgacgacagg   9300
tactacaccc gtagtcgaaa aaacagagcc caatgctgat ggtggtccaa gctccataaa   9360
gattgggttg gatgaaggaa gatacccagg acctggactg caagaccgca ccttgaccga   9420
tgaaatacat tctagggatg aaaggccctt tgttctagtc ctgggctcaa aaaattctat   9480
gtcaaataga gctaaaactg ctagaaacat caacttatac aaggggaata accccaggga   9540
gattagagat ctgatggcac aggggcgtat gctagttgtg gccttaaagg attttaaccc   9600
tgagttgtct gaactagttg atttcaaggg gactttctta gacagggaag ccttggaagc   9660
tctcagcctg gggcggccaa agtccaagca ggtgaccaca gccacagtta gggagttatt   9720
agagcaggag gtacaagttg agatccccag ttggtttgga gcaggtgatc cagtcttctt   9780
ggaagtgact ttgaagggtg acagatatca cttagtagga gatgtagata gagtgaaaga   9840
tcaagcgaag gagcttgggg ccacggacca gacaagaata gtgaaggaag tgggtgcaag   9900
aacctatacc atgaagctgt ctagttggtt tcttcaggca acaaataaac agatgagctt   9960
gacccctta tttgaggagc tattgctacg ttgccccccct aaaataaaga gcaataaagg  10020
gcacatggca tcagcttacc aactagcaca gggaaactgg gagcccttg actgtggagt   10080
tcacctgggc accatacctg ccaggagggt aaaaatccac ccatatgaag cttacctgaa  10140
actgaaggat ttattggaag aagaagaaaa gaaaccaaag tgtagagaca cagtaataag  10200
agaacacaac aagtggatcc tcaaaaaagt gaggcaccag ggtaatctca atacaaagaa  10260
aatcctcaac cctggaaagc tatcagaaca gctagataga aagggcata aaagaaacat   10320
ttataacaat cagattggca ccataatgac ggaagcagga agtaggttgg aaaaattacc  10380
agtcgtcaga gcccaaactg acactaaaag cttccatgag gcaatcagag ataagataga  10440
caagaatgaa aatcagcaga gcccaggact gcatgataaa ttgttagaga tctttcatac  10500
aatagcccaa cccagcctaa gacacaccta cagtgacgtg acgtgggagc aacttgaggc  10560
agggggttaat agaaaggggg ctgctggctt tctagagaag aagaatgttg gagaagtact  10620
ggactcagag aagcacctgg tggaacaact gatcagagat ttgaaaacag gaaggaagat  10680
aagatattat gagacagcaa taccaaaaaa tgagaagaga gatgtcagtg atgattggca  10740
atcagggac ttagtagatg agaagaaacc aaggtgatt caatacctg aagctaaaac     10800
aagactagcc atcactaaag taatgtacaa ctgggtgaaa cagcagcccg tcgtgatccc  10860
agggtatgaa gggaagaccc cattatttaa cattttcaac aaggtgagga aggaatggga  10920
tttgttcaat gaaccagtag ctgtgagttt cgacactaag gcttgggaca cccaagtaac  10980
tagtagagat ctacggctta ttggtgaaat tcaaaaatat tactacagga agagtggca   11040
caaattcatc gataccatta ctgaccatat ggtggaggtg cccgtcataa cggcagatgg  11100
tgaggtatac ataagaaatg gacaaggggg tagtggccag ccagacacaa gtgcaggcaa  11160
```

```
tagcatgcta aacgtgttaa caatgatgta tgccttctgt gaaagtacgg gggttccata   11220
caagagtttc aatagggttg caaggatcca tgtctgtggg gatgacggct tcctaataac   11280
agagaagggg ctgggattaa agtttgccaa caatgggatg caaattctgc acgaagcagg   11340
caagcctcaa aagataactg aggggggaaag aatgaaagtt gcctataggt tcgaggacat   11400
agaattctgc tctcatacac cagtccccgt taggtggtct gataacacca gcagttacat   11460
ggccggcaga gacactgccg ttatattatc aaagatggca acaagattgg attcaagtgg   11520 agaaagggt actatagcat atgaaaaagc agtggccttt agttttttgc tgatgtactc   11580
ctggaatcct cttgtgagga ggatctgtct actggtcctt tcacagcagc cagagacaac   11640
tccatcaacc cagaccactt actattataa aggagaccca ataggagcct acaaagatgt   11700
aataggtaag aatttgtgtg aattaaaaag gacgggtttt gaaaaattgg ccaatttaaa   11760
cctaagcctg tccacgttag gaatctggtc caaacataca agtaaaagaa tcatccaaga   11820
ctgtgtaacc atcgggaaag aggaaggcaa ttggctggtc aatgccgaca ggttgatatc   11880
tagcaaaact ggccatttgt atacctga caaaggttat acattacaag gaaacatta   11940 tgaacaactt caactgcagg caagaactag cccagtcacg ggagtaggga cggagagata   12000
taaactaggc cctatagtaa acctgctgct gaggaggttg agagttctgc ttatggcagc   12060
tgtcggtgcc agcagttgaa ataatgtatg tatatattgt atataaatct gtatttgtat   12120
atattatgtt taaatacgta gccagccccc gattgggggc gacactccac catagatcac   12180
tcccctgtga ggaactactg tcttcacgca gaaagcgtct agccatggcg ttagtatgag   12240
tgtcgtgcag cctccaggac ccccctctc gggagagcca tagtggtctg cggaaccggt    12300
gagtacaccg gaattgccag gacgaccggg tcctttcttg gatcaacccg ctcaatgcct   12360
ggagatttgg gcgtgccccc gcgagactgc tagccgagta gtgttgggtc gcgaaaggcc   12420
ttgtggtact gcctgatagg gtgcttgcga gtgcctcggg aggtctcgta gaccgtgcac   12480
cttaattaat aatttagttg agattagtag tgatatatag ttatctaccct caagctaaca   12540 ctacactcaa tgcacacagc actttagctg tatgagggta caccccgacgt ccacggttgg   12600 actagggaaa acccttaaca gcccc                                        12625
```

<210> SEQ ID NO 4
<211> LENGTH: 12281
<212> TYPE: DNA
<213> ORGANISM: Pestivirus type 1
<220> FEATURE:
<221> NAME/KEY: misc_feature
<223> OTHER INFORMATION: BVDV-non-CP7 + cloning site; BVDV-non-CP7 with
     SnaBI, PacI restriction endonuclease insert

<400> SEQUENCE: 4

```
gtatacgagg ttaggcaagt tctcgtatac atattggaca ctctaaaaat aattaggcct     60
aggggacaaa aatcctcctt agcgaaggcc gaaagaggc taaccatgcc cttagtagga    120
ctagcaaaat aaggggggta gcaacagtgg cgagttcgtt ggatggctga agccctgagt    180
acagggtagt cgtcagtggt tcgacgcttt ggaggacaag cctcgagatg ccacgtggac    240
gagggcatgc ccacagcaca tcttaacctg gacaggggtc gttcaggtga aacggttta    300 accaaccgct acgaatacag tctgatagga tgctgcagag gcccactgta ttgctactga    360
aaatctctgc tgtacatggc acatggagtt gatcacaaat gaacttttat acaaaacata    420
caaacaaaaa cccgctggag tggaggaacc agtatacgac caagctggta accctttgtt    480
tggagaaaga ggagtgattc atccgcagtc aacgctaaaa cttccacata aagagggga    540
```

```
gcgtgaagtc cccaccaatc tggcttcttt accaaaaaga ggtgactgca ggtcgggtaa    600
cagcaagggg cctgtgagtg gaatctactt aaaaccaggg ccgttattct accaagatta    660
taaaggacct gtctatcata gagccccatt ggagtttttt gaggaggcgt ctatgtgtga    720
gacaactaaa agaataggga gagtaactgg tagtgacagc agattatacc acatttacgt    780
gtgtattgat gggtgcataa tagtcaagag tgctacaaaa gaccgccaga aagtactcaa    840
gtgggtccac aacaagctaa actgcccct  atgggtttca agctgctccg cacaaaaga    900 tgaaggggtg gtgaggaaga agcaacaaaa gccagatagg ttggaaaagg ggagaatgaa    960
gataacacct aaggagtcag agaaagacag taagaccaag ccgccagatg ctacgatagt   1020
ggtagatgga gtcaagtatc aggtaaagaa aaaggaaaa  gtcaagagca agaacaccca   1080
ggacggctta taccacaaca aaaataaacc tcaagagtcg cgcaagaaac tagagaaagc   1140
cctattggcc tgggcaataa tagccctggt tttctttcaa gtcacaatgg gagagaacat   1200
aacgcaatgg aacttacaag ataatggaac ggaaggcata caacgagcca tgtttcaaag   1260
aggagtgaat agaagtttac atgggatctg ccagagaaa  atctgtacag gtgttccttc   1320
ccacctggcc actgacacag aattgaaggc aattcatggt atgatggatg caagtgagaa   1380
gacaaattat acgtgctgca gactccaacg ccatgaatgg aacaaacatg gttggtgcaa   1440
ctggtacaac attgaacctt ggatcctcct tatgaataaa actcaggcca accttactga   1500
gggtcagcca ctaagggagt gtgccgtcac atgccggtat gatcgagata gtgacctgaa   1560
tgtagtaaca caagccaggg atagccccac accattaaca ggttgcaaga aaggcaaaaa   1620
cttttccttt gcaggcatat tggtacaagg ccttgcaac  tttgaaatag ccgtaagtga   1680
tgtgctgttc aaagagcatg attgcactag tgtgattcaa  gacacagctc actacctcgt   1740
agacgggatg accaactccc tagagagtgc caggcaaggg accgcgaaac taacaacttg   1800
gctgggcagg cagcttggga tactaggaaa gaaactggaa  acaagagta agacatggtt   1860 tgggcatat  gcagcctctc cctattgtga ggtagaacgg aagcttggtt acatctggta   1920
tacaaagaat tgcactccag cctgtttgcc  taggaataca aagatcatcg gccccggtag   1980
gtttgacacc aatgccgagg atggtaaaat actgcatgag atggggggtc acttgtcgga   2040
ggtgctacta ctctcagtgg tagtgctgtc cgatttcgct ccagagacag ccagtgtgat   2100
atacttgatt cttcatttct ccatcccaca aggacacact gatatacaag attgtgacaa   2160
aaaccaacta aacctcaccg tagaactcac aacagcagaa gtaataccag gctcagtttg   2220
gaacttgggt aaatatgttt gtgtaagacc agattggtgg cctttatgaga cagccacagt   2280 cctggtgatt gaagaggtgg gtcaagtaat taaggttgtc ttaagggcgt taaaagatct   2340
gacgcgcatt tggaccgctg ctacaaccac tgcattcttg gtttgtctgg tgaaggtagt   2400
gagaggccaa gtgttacaag gtatactgtg gctgatgctc ataacagggg cgcaagggta   2460
cccagactgc aaacccggct tttcatacgc catagccaaa aatgatgaga ttggcccact   2520
tggagctaca ggcctcacca ctcagtggta cgaatactcg gatgggatgc ggctgcagga   2580
ctcagtagtt gaagtttggt gtaaaaatgg agagatcaaa tatctaatca gatgcgggag   2640
ggaagccagg tatctggctg ttctacacac gagagccttg ccgacatctg tagtatttga   2700
aaaaattttt gatgggaaag aacaagagga catagtagaa atggatgaca actttgaatt   2760
cggtctttgc ccgtgtgatg ctagaccctt gataagggga aaatttaata caacacttct   2820
aaatgggcca gccttccaga tggtttgccc tataggatgg acagggactg taagctgtac   2880
```

| | |
|---|---|
| actggccaat aaggatacgt tagccacaat cgttgtgaga acgtataaga gggtcaggcc | 2940 |
| ttttccatat aggcaggact gtgtcaccca gaaaaccatc ggggaagacc tctacgactg | 3000 |
| tgccttagga gggaattgga cttgtgtgcc gggggatgca ctacgatatg tagctgggcc | 3060 |
| cgttgagtct tgtgagtggt gtggttacaa gttttttaaaa agtgagggtc tgccgcattt | 3120 |
| cccaatcggc aaatgcaggc tgaagaatga gagtggctat agacaagtgg atgagacttc | 3180 |
| ttgcaacaga aacggcgtgg ctatagtgcc atctggcacg gtcaaatgca agatagggga | 3240 |
| cacggtggtg caagtcattg caatggatga taaactaggg cctatgcctt gcaaaccaca | 3300 |
| tgaaatcata tccagtgagg ggccagtgga aagacggca tgcaccttca actacacaag | 3360 |
| aacattaaaa aacaagtact ttgagcccag ggataactat tttcaacaat acatgttaaa | 3420 |
| gggggagtac caatattggt ttgacctaga gatcactgac caccaccgag attacttcgc | 3480 |
| tgagtccctg ttggtgatag tagttgcact cctgggtggc aggtacgtgc tttggctgct | 3540 |
| ggtcacatac atgatcttat cagaacagat ggcctcgggt gtccagtatg ggcaggtga | 3600 |
| aatagtgatg atgggcaact tgttaacaca tgacagtgtt gaagtggtga catatttctt | 3660 |
| actactatac ctactactaa gagaggaaaa caccaaaaaa tgggtcatac ttatatacca | 3720 |
| catcatagta atgcatcctc taaaatcggt gacggtgata ttgctaatgg ttgggggat | 3780 |
| ggcaaaggct gaaccaggtg cccaggggta cctagagcag gtagacctta gttttacgat | 3840 |
| gattacgatc atcgtaatag gtctggttat agctaggcgt gatcccactg tggtgccact | 3900 |
| agtcactata gtcgcggcac tgaagatcac aggactaggc tttgggcccg gagtggatgc | 3960 |
| agctatggca gttctcacct taccctact gatgactagt tatgtgacag actacttcag | 4020 |
| gtataaaagg tggatacaat gtatcctcag cttagtagcc ggggtgttcc ttatccggac | 4080 |
| cctcaaacat ctaggtgaac tcaaaacccc tgagctgacc ataccaaatt ggaggccact | 4140 |
| aaccttcata ctattatacc tgacttcagc aacagttgtt acaagatgga aaattgatat | 4200 |
| agctggcata ttcctgcaag ggccccctat ccttttgatg atcgccaccc tatgggctga | 4260 |
| cttcttgact cttgttctga tcctacccac ctacgaatta gccaagctgt actacctaaa | 4320 |
| gaacgtcaag actgacgtgg agaagagttg gctgggggg ttagactaca ggacaattga | 4380 |
| ctctgtctat gatgtggatg aaagtggaga aggcgtgtac ctcttcccgt ccagacagaa | 4440 |
| gaaaaataag aatatcagca tactcttgcc cctcatcaga gctacgctaa taagttgtat | 4500 |
| tagcagcaaa tggcagatgg tgtatatggc ttacttaacc ctggactta tgtactacat | 4560 |
| gcacagaaag gttattgaag agatatcagg gagtaccaat gtgatgtcta gagtgatagc | 4620 |
| agcacttata gaattaaact ggtccatgga agaagaagag agcaagggct taagaagtt | 4680 |
| ttttatacta tctggaaggt tgaggaacct tataataaag cataaggtta ggaaccagac | 4740 |
| tgtggcaagc tggtatgggg aggaagaagt ctacggcatg ccaaaagtcg taaccataat | 4800 |
| aagggcctgc acgctaaaca agaacaaaca ttgcataata tgcacagtat gtgaggctag | 4860 |
| aaagtggaag ggaggcaact gccctaaatg cggccgccac gggaagccca tcatttgtgg | 4920 |
| gatgactcta gcggattttg aagaaggca ctacaagaga attttttataa gggaaggtaa | 4980 |
| ctttgaagga ccccttcaggc aggaatacaa tgggtttgta caatacaccg ctaggggca | 5040 |
| attgttcctg agaaatttac ccatattggc aaccaaagta aaaatgatca tggtaggcaa | 5100 |
| cctaggagag gaaatcggtg atctagaaca cctaggatgg atcctaaggg gacctgccgt | 5160 |
| gtgcaagaaa ataactgagc acgaaaaatg ccatgtcaac atactggaca agctgactgc | 5220 |
| gttttttgga gttatgccaa gagggactac accaagggct ccggtgagat tcccaacagc | 5280 |

-continued

```
actactaaag gtaaggaggg gattggaaac cggttgggct tacacgcatc aaggtggcat   5340
aagctcagta gaccatgtga ccgctggcaa ggatctattg gtttgtgaca gtatgggtag   5400
aactagagtg gtttgccaaa gcaacaacaa gttaactgat gagacagaat atggtgtcaa   5460
gacggactcc ggatgtccag atggtgccag atgctatgta ttaaacccag aggcagtaaa   5520
tatatcaggg tccaagggag ctgtcgtaca cctccaaaaa acgggtgggg aatttacatg   5580
tgttactgca tcaggtacac cggccttctt cgacctgaaa aatttgaaag gatggtcggg   5640
tctacccata tttgaagcct ccagcggcag agtggttggc agagtcaaag tgggaaagaa   5700
tgaggaatcc aaacccacaa aattaatgag tggtatccaa actgtttcta aaaatacggc   5760
cgatttaaca gaaatggtca agaagataac cagcatgaac aggggggact ttaggcagat   5820
aacccttgca cagggggcag ggaagaccac tgagctccca aaagcagtga tagaggagat   5880
aggacgacac aaacgggtac tagtgctcat accattaaga gcagcagctg agtcagtcta   5940
tcaatacatg agattgaaac acccaagtat ctcctttaac ctgagaatag gggacatgaa   6000
agaaggggat atggcaaccg ggatcaccta cgcctcatat ggatattttt gccaaatgcc   6060
acaaccaaag ctcagagcag caatgataga gtattcatac atatttctgg atgagtatca   6120
ctgcgctact cctgagcagt tggctgttat aggaaaaatt cacagatttt ctgagagcat   6180
aagagtggtt gccatgactg ccaccccagc agggtcagta accacaacag ggcaaaaaca   6240
cccaatagaa gaattcatag cccctgaggt gatgaaaggg gaggaccttg aagccagtt   6300 ccttgacata gcggggttaa agatccctgt agaggagatg aagggtaaca tgttggtttt   6360
cgtgcccacg aggaacatgg cagttgaagt agccaagaaa ctaaaagcca agggctacaa   6420
ctcagggtat tactacagtg gggaagaccc agctaacttg agagtggtaa catcacagtc   6480
cccatacgtc gtggtagcca ctaatgccat cgagtcaggg gtaacgctgc cagatttaga   6540
tacagttgtt gacacaggtc tgaaatgtga agagagggtg aggtgtcttc caaaataccc   6600
ctttatagta acaggcctta agagaatggc tgtcactgtg ggcgaacagg ctcagcggag   6660
aggcagggta ggtagagtga aacccggtag gtattataga agtcaggaaa cagcaaccgg   6720
gtcaaaggac taccactatg acttgttaca ggcacagagg tacgggatcg aagatgggat   6780
caacgtaaca aagtccttta gggagatgaa ttatgactgg agcctgtatg aggaagacag   6840
cttgctgata acccagctgg agatactgaa caatctactc atctctgaag atttaccagc   6900
agctgttaaa aacatcatgg caagaactga tcacccagag cctatccagc ttgcatataa   6960
cagttatgag gtccaagtcc ctgtgctgtt cccaaaaata aggaatgggg aggtcacaga   7020
cacttacgag aactactcat tcctaaatgc aaggaaacta ggggaagacg tgcccgtgta   7080
cgtttatgcc accgaagatg aagatctggc tgtggacctt ctaggcttgg actggccaga   7140
cccagggaat cagcaagtag tggagactgg gaaggcactg aagcaagtgg taggactgtc   7200
ctctgccgaa aatgccttgc tcatagccct atttgggtat gtaggatacc aagccttgtc   7260
aaaaagacac gtcccaatga tcacagacat atacactata gaagatcaaa gactagagga   7320
cacaacccac cttcaatatg cgcccaatgc cataagaact gaggggaagg agactgaact   7380
aaaggaatta gcagtgggtg acttggacaa aatcatgggt tccatctcgg actatgcatc   7440
agagggattg aatttcgtaa ggtcccaagc agaaagatg agatctgccc ccgctttcaa   7500
agaaaacgtg gaagctgcta aagggtacgt ccaaaagttt attgattctc tcatagaaaa   7560
taaagaaacc ataatcagat atggcctgtg gggaacacac acggcactct acaagagtat   7620
```

```
tgccgcgaga ttgggtcatg aaactgcatt cgctcacta gtgataaagt ggctggcctt      7680
cgggggtgag tcgtgtcag accacatgag acaagcagct gtcgacctgg ttgtttatta      7740
tgtgatcaat aagccctcct tcccagggga ttctgaaacc aacaggaag gaaggcgatt      7800 cgtcgccagc ctgttcatct ccgctttggc aacctacaca tacaaaactt ggaattacaa      7860
caacctctcc aaggtagtag aaccagcctt agcatacctc ccctatgcta ccaatgcact      7920
aaaaatgttt accccgacca gactggagag cgtagttata cttagtacca caatatacaa      7980
aacttacctc tcaataagga agggaaagag tgatggactg ttgggtacag ggatcagtgc      8040
agcaatggag attctatcac agaacccagt gtcggtaggt atatctgtca tgctgggggt      8100
gggggcgatt gccgcgcaca atgccattga gtctagtgaa caaaaaagga ccctgttgat      8160
gaaagtgttt gtaaaaaact tcctggacca ggcggcaaca gatgagctgg taaaggaaaa      8220
cccagagaaa ataataatgg ccctatttga agcagtccag acaattggca accccttgag      8280
gctcatatat cacctgtatg ggtttacta caaaggctgg gaagcaaaag aactatcaga      8340
gagaacagca ggcaggaacc tgttcacctt gataatgttc gaagccttcg aactactagg      8400
gatggactct gaagggaaga taaggaacct gtctgggaat tatgtcctgg atttgatcta      8460
cagcctacat aaacagataa atagaggctt gaaaaaaata gtcttggggt gggctcccgc      8520
accatttagt tgcgactgga ctccatgta tgagagaatt aggttaccca caaacaacta      8580
tctaagagta gaaactaagt gtccatgtgg ctatgagatg aaagcactaa ggaacgttgg      8640
tggcagtctt accaaagtgg aggagaaagg accttttctc tgcaggaaca ggcttggtag      8700
agggccggtc aactatagag tcacaaagta ctatgatgac aacctcaaag agataaaacc      8760
agttgctaaa ctagaaggat ttgtggatca ctattacaaa ggtgttacag caaggataga      8820
ttatggcaga gggaaaatgc tattagctac tgataaatgg gaggtggagc acggtgttgt      8880
cactaggttg gcaaagagat ataccggagt tggattcaag ggagcatacc tgggtgatga      8940
acccaaccac cgcgacctag tagaaagaga ctgtgcaact ataacaaaaa atacagtgca      9000 gttttttaaaa atgaagaaag gctgtgcatt tacctatgac ttaaccctgt ccaatttaac      9060
caggttaatt gaattggtac acaaaaataa cctagaagag aaagacatac cagcagccac      9120
agtaacgaca tggctggctt atactttgt aaatgaagat attgggacta taaaaccagt      9180
actaggagag agagtggtca ccgacccagt ggtggatgtt aacttacaac cagaagtaca      9240
agtggataca tcagaggttg ggatcacttt agttggtagg gcagccttaa tgacgacagg      9300
tactacaccc gtagtcgaaa aaacagagcc aatgctgat ggtggtccaa gctccataaa      9360
gattgggttg gatgaaggaa gatacccagg acctggactg caagaccgca ccttgaccga      9420
tgaaatacat tctaggatg aaaggccctt tgttctagtc ctgggctcaa aaaattctat      9480
gtcaaataga gctaaaactg ctagaaacat caacttatac aaggggaata accccaggga      9540
gattagagat ctgatggcac aggggcgtat gctagttgtg gccttaaagg atttttaaccc      9600 tgagttgtct gaactagttg atttcaaggg gactttctta gacagggaag ccttggaagc      9660
tctcagcctg gggcggccaa agtccaagca ggtgaccaca gccacagtta gggagttatt      9720
agagcaggag gtacagttg agatccccag tggtttgga gcaggtgatc cagtcttctt      9780
ggaagtgact ttgaagggtg acagatatca cttagtagga gatgtagata gagtgaaaga      9840
tcaagcgaag gagcttgggg ccacggacca gacaagaata gtgaaggaag tgggtgcaag      9900
aacctatacc atgaagctgt ctagttggtt tcttcaggca caaataaaac agatgagctt      9960 gacccctta tttgaggagc tattgctacg ttgcccccct aaaataaaga gcaataaagg     10020
```

```
gcacatggca tcagcttacc aactagcaca gggaaactgg gagccccttg actgtggagt    10080
tcacctgggc accatacctg ccaggagggt aaaaatccac ccatatgaag cttacctgaa    10140
actgaaggat ttattggaag aagaagaaaa gaaaccaaag tgtagagaca cagtaataag    10200
agaacacaac aagtggatcc tcaaaaaagt gaggcaccag ggtaatctca atacaaagaa    10260
aatcctcaac cctggaaagc tatcagaaca gctagataga gaagggcata aagaaacat    10320 ttataacaat cagattggca ccataatgac ggaagcagga gtaggttgg aaaaattacc     10380 agtcgtcaga gcccaaactg acactaaaag cttccatgag gcaatcagag ataagataga    10440
caagaatgaa atcagcaga gcccaggact gcatgataaa ttgttagaga tctttcatac     10500
aatagcccaa cccagcctaa gacacaccta cagtgacgtg acgtgggagc aacttgaggc    10560
aggggttaat agaaagggg ctgctggctt tctagagaag aagaatgttg gagaagtact     10620
ggactcagag aagcacctgg tggaacaact gatcagagat ttgaaaacag gaaggaagat    10680
aagatattat gagacagcaa taccaaaaaa tgagaagaga gatgtcagtg atgattggca    10740
atcaggggac ttagtagatg agaagaaacc aagggtgatt caatacctg aagctaaaac     10800 aagactagcc atcactaaag taatgtacaa ctgggtgaaa cagcagcccg tcgtgatccc    10860
agggtatgaa gggaagaccc cattatttaa cattttcaac aaggtgagga aggaatggga    10920
tttgttcaat gaaccagtag ctgtgagttt cgacactaag gcttgggaca cccaagtaac    10980
tagtagagat ctacggctta ttggtgaaat tcaaaaatat tactacagga aagagtggca    11040
caaattcatc gataccatta ctgaccatat ggtggaggtg cccgtcataa cggcagatgg    11100
tgaggtatac ataagaaatg gacaaggggg tagtggccag ccagacacaa gtgcaggcaa    11160
tagcatgcta aacgtgttaa caatgatgta tgccttctgt gaaagtacgg gggttccata    11220
caagagtttc aatagggttg caaggatcca tgtctgtggg gatgacggct tcctaataac    11280
agagaagggg ctgggattaa agtttgccaa caatgggatg caaattctgc acgaagcagg    11340
caagcctcaa aagataactg agggggaaag aatgaaagtt gcctataggt tcgaggacat    11400
agaattctgc tctcatacac cagtcccccgt taggtggtct gataacacca gcagttacat    11460
ggccggcaga gacactgccg ttatattatc aaagatggca acaagattgg attcaagtgg    11520 agaaagggt actatagcat atgaaaaagc agtggccttt agttttttgc tgatgtactc    11580
ctggaatcct cttgtgagga ggatctgtct actggtcctt tcacagcagc cagagacaac    11640
tccatcaacc cagaccactt actattataa aggagaccca ataggagcct acaaagatgt    11700
aataggtaag aatttgtgtg aattaaaaag gacgggtttt gaaaaattgg ccaatttaaa    11760
cctaagcctg tccacgttag gaatctggtc caaacataca agtaaaagaa tcatccaaga    11820
ctgtgtaacc atcgggaaag aggaaggcaa ttggctggtc aatgccgaca ggttgatatc    11880
tagcaaaact ggccatttgt acatacctga caaggttat acattacaag ggaaacatta    11940
tgaacaactt caactgcagg caagaactag cccagtcacg ggagtaggga cggagagata    12000
taaactaggc cctatagtaa acctgctgct gaggaggttg agagttctgc ttatggcagc    12060
tgtcggtgcc agcagttgaa ataatgtatg tatatattgt atataaatct gtatttgtat    12120
atattatgtt taaatacgta ttaattaatt tagttgagat tagtagtgat atatagttat    12180
ctacctcaag ctaacactac actcaatgca cacagcactt tagctgtatg agggtacacc    12240
cgacgtccac ggttggacta gggaaaaccc ttaacagccc c                        12281
```

<210> SEQ ID NO 5

```
<211> LENGTH: 355
<212> TYPE: DNA
<213> ORGANISM: Pestivirus type 1
<220> FEATURE:
<221> NAME/KEY: misc_feature
<223> OTHER INFORMATION: BVDV-non-CP7 3' NTR

<400> SEQUENCE: 5
tacgtagcca gccccgatt ggggcgaca ctccaccata gatcactccc ctgtgaggaa      60
ctactgtctt cacgcagaaa gcgtctagcc atggcgttag tatgagtgtc gtgcagcctc     120
caggaccccc cctctcggga gagccatagt ggtctgcgga accggtgagt acaccggaat     180
tgccaggacg accgggtcct tcttggatc aacccgctca atgcctggag atttgggcgt      240 gccccgcga gactgctagc cgagtagtgt tgggtcgcga aaggccttgt ggtactgcct      300
gatagggtgc ttgcgagtgc ctcgggaggt ctcgtagacc gtgcacctta attaa         355

<210> SEQ ID NO 6
<211> LENGTH: 205
<212> TYPE: DNA
<213> ORGANISM: Pestivirus type 1
<220> FEATURE:
<221> NAME/KEY: misc_feature
<223> OTHER INFORMATION: BVDV-non-CP7 + cloning site chimera, 3'NTR,
      SnaBI and PacI restriction endonuclease insert

<400> SEQUENCE: 6
tgaaataatg tatgtatata ttgtatataa atctgtattt gtatatatta tgtttaaata      60
cgtattaatt aatttagttg agattagtag tgatatatag ttatctacct caagctaaca    120
ctacactcaa tgcacacagc actttagctg tatgagggta cacccgacgt ccacggttgg    180
actagggaaa acccttaaca gcccc                                           205

<210> SEQ ID NO 7
<211> LENGTH: 549
<212> TYPE: DNA
<213> ORGANISM: Pestivirus type 1
<220> FEATURE:
<221> NAME/KEY: misc_feature
<223> OTHER INFORMATION: BVDV-non-CP7- HCV 5' NTR chimera, 3'NTR

<400> SEQUENCE: 7
tgaaataatg tatgtatata ttgtatataa atctgtattt gtatatatta tgtttaaata      60
cgtagccagc ccccgattgg gggcgacact ccaccataga tcactcccct gtgaggaact    120
actgtcttca cgcagaaagc gtctagccat ggcgttagta tgagtgtcgt gcagcctcca    180 ggacccccc tctcgggaga gccatagtgg tctgcggaac cggtgagtac accggaattg    240
ccaggacgac cgggtccttt cttggatcaa cccgctcaat gcctggagat ttgggcgtgc    300
ccccgcgaga ctgctagccg agtagtgttg gtcgcgaaa ggccttgtgg tactgcctga    360
tagggtgctt gcgagtgcct cgggaggtct cgtagaccgt gcaccttaat taatatttta   420
gttgagatta gtagtgatat atagttatct acctcaagct aacactacac tcaatgcaca   480
cagcacttta gctgtatgag gtacacccg acgtccacgg ttggactagg gaaaaccctt    540
aacagcccc                                                            549

<210> SEQ ID NO 8
<211> LENGTH: 524
<212> TYPE: DNA
<213> ORGANISM: Pestivirus type 1
<220> FEATURE:
<221> NAME/KEY: misc_feature
```

<223> OTHER INFORMATION: BVDV-non-CP7 - HCV 5' NTR chimera, BamHI / XbaI
       cloned PCR fragment, clone 1

<400> SEQUENCE: 8

| | | | | | |
|---|---|---|---|---|---|
| ggatccgctg | tcggtgccag | cagttgaaat | aatgtatgta | tatattgtat | ataaatctgt | 60 |
| atttgtatat | attatgttta | aatacgtagc | cagcccccta | ttggggggcga | cactccacca | 120 |
| tagatcactc | ccctgtgagg | aactactgtc | ttcacgcaga | aagcgtctag | ccatggcgtt | 180 |
| agtatgagtg | tcgtgcagcc | tccaggaccc | ccctctcgg | gagagccata | gtggtctgcg | 240 |
| gaaccggtga | gtacaccgga | attgccagga | cgaccgggtc | ctttcttgga | tcaacccgct | 300 |
| caatgcctgg | agatttgggc | gtgccccgc | gagactgcta | gccgagtagt | gttgggtcgc | 360 |
| gaaaggcctt | gtggtactgc | ctgataggt | gcttgcgagt | gcctcgggag | gtctcgtaga | 420 |
| ccgtgcacct | taattaataa | tttagttgag | attagtagtg | atatatagtt | atctacctca | 480 |
| agctaacact | acactcaatg | cacacagcac | tttagctgtc | taga | | 524 |

<210> SEQ ID NO 9
<211> LENGTH: 524
<212> TYPE: DNA
<213> ORGANISM: Pestivirus type 1
<220> FEATURE:
<221> NAME/KEY: misc_feature
<223> OTHER INFORMATION: BVDV non-CP7 - HCV 5'NTR chimera, BamHI / XbaI
       cloned PCR fragment, clone 2

<400> SEQUENCE: 9

| | | | | | |
|---|---|---|---|---|---|
| ggatccgctg | tcggtgccag | cagttgaaat | aatgtatgta | tatattgtat | ataaatctgt | 60 |
| atttgtatat | attatgttta | aatacgtagc | cagcccccga | ttggggggcga | cactccacca | 120 |
| tagatcactc | ccctgtgagg | aactactgtc | ttcacgcaga | aagcgtctag | ccatggcgtt | 180 |
| agtatgagtg | tcgtgcagcc | tccaggaccc | ccctctcgg | gagagccata | gtggtctgcg | 240 |
| gaaccggtga | gtacaccgga | attgccagga | cgaccgggtc | ctttcttgga | tcaacccgct | 300 |
| caatgcctgg | agatttgggc | gtgccccgc | gagactgcta | gccgagtagt | gttgggtcgc | 360 |
| gaaaggcctt | gtggtactgt | ctgataggt | gcttgcgagt | gcctcgggag | gtctcgtaga | 420 |
| ccgtgcacct | taattaataa | tttagttgag | attagtagtg | atatatagtt | atctacctca | 480 |
| agctaacact | acactcaatg | cacacagcac | tttagctgtc | taga | | 524 |

<210> SEQ ID NO 10
<211> LENGTH: 524
<212> TYPE: DNA
<213> ORGANISM: Pestivirus type 1
<220> FEATURE:
<221> NAME/KEY: misc_feature
<223> OTHER INFORMATION: BVDV-non-CP7- HCV 5' NTR chimera, BamHI / Xba I
       cloned PCR fragment, clone 3

<400> SEQUENCE: 10

| | | | | | |
|---|---|---|---|---|---|
| ggatccgctg | tcggtgccag | cagttgaaat | aatgtatgta | tatattgtat | ataaatctgt | 60 |
| atttgtatat | attatgttta | aatacgtagc | cagcccccga | ttggggggcga | cactccacca | 120 |
| tagatcactc | ccctgtgagg | aactactgtc | ttcacgcaga | aagcgtctag | ccatggcgtt | 180 |
| agtatgagtg | tcgtgcagcc | tccaggaccc | ccctctcgg | gagagccata | gtggtctgcg | 240 |
| gaaccggtga | gtacaccgga | attgccagga | cgaccgggtc | ctttcttgga | tcaacccgct | 300 |
| caatgcctgg | agatttgggc | gtgccccgc | gagactgcta | gccgagtagt | gttgggtcgc | 360 |
| gaaaggcctt | gtggtactgc | ctgataggt | gcttgcgagt | gcctcgggag | gtctcgtaga | 420 |

```
ccgtgcacct taattaataa tttagttgag attagtagtg atatatagtt atctacctca    480
agccaacact acactcaatg cacacagcac tttagctgtc taga                    524
```

<210> SEQ ID NO 11
<211> LENGTH: 524
<212> TYPE: DNA
<213> ORGANISM: Pestivirus type 1
<220> FEATURE:
<221> NAME/KEY: misc_feature
<223> OTHER INFORMATION: BVDV-non-CP7 - HCV 5'NTR chimera, BamHI / XbaI
      cloned PCR fragment, clone 4

<400> SEQUENCE: 11

```
ggatccgctg tcggtgccag cagttgaaat aatgtatgta tatattgtat ataaatctgt     60
atttgtatat attatgttta aatacgtagc cagcccccga ttgggggcga cactccacca    120
tagatcactc ccctgtgagg aactactgtc ttcacgcaga aagcgtctag ccatggcgtt    180
agtatgagtg tcgtgcagcc tccaggaccc ccctctcggg agagccata gtggtctgcg    240 gaaccggtga gtacaccgga attgccagga cgaccgggtc ctttcttgga tcaacccgct    300
caatgcctgg agatttgggc gtgccccgc gagactgcta gccgagtagt gttgggtcgc    360
gaaaggcctt gtggtactgc ctgatagggt gcttgcgagt gcctcgggag gtctcgtaga    420
ccgtgcacct taattaataa tttagttgag attagtagtg atatatagtt atctacctca    480
agctaacact acactcaatg cacacagcac tttagctgtc taga                    524
```

<210> SEQ ID NO 12
<211> LENGTH: 523
<212> TYPE: DNA
<213> ORGANISM: Pestivirus type 1
<220> FEATURE:
<221> NAME/KEY: misc_feature
<223> OTHER INFORMATION: BVDV-non-CP7 - HCV 5'NTR chimera, BamHI / XbaI
      cloned PCR fragment, clone 5

<400> SEQUENCE: 12

```
ggatccgctg tcgtgccagc agttgaaata atgtatgtat atattgtata taaatctgta     60
tttgtatata ttatgtttaa atacgtagcc agccccccgat tggggggcgac actccaccat   120 agatcactcc cctgtgagga actactgtct tcacgcagaa agcgtctagc catggcgtta    180
gtatgagtgt cgtgcagcct ccaggacccc ccctctcggg agagccatag tggtctgcgg    240
aaccggtgag tacaccggaa ttgccaggac gaccgggtcc tttcttggat caacccgctc    300
aatgcctgga gatttgggcg tgccccgcg agactgctag ccgagtagtg ttgggtcgcg    360
aaaggccttg tggtactgcc tgatagggtg cttgcgagtg cctcgggagg tctcgtagac    420
cgtgcacctt aattaataat ttagttgaga ttagtagtga tatatagtta tctacctcaa    480
gctaacacta cactcaatgc acacagcact ttagctgtct aga                     523
```

<210> SEQ ID NO 13
<211> LENGTH: 276
<212> TYPE: DNA
<213> ORGANISM: Border disease virus

<400> SEQUENCE: 13

```
tgaaccatag ctgagcattt catgacaaca cgccaagggc cactaaattg tatatataac     60
tgtgtaaata tttacctatt tatttactgt tatttattta atagagacag tgatatttat    120
ttaatagctt atctatttat ttatttgatg ggatgtagat ggcaactaac tacctcatag    180
gaccacacta cactcatttt taaaactaca gcactttagc tggaagggaa aagcctgaag    240
```

```
tccagagttg gattaaggaa aaaccctaac agcccc                                 276

<210> SEQ ID NO 14
<211> LENGTH: 244
<212> TYPE: DNA
<213> ORGANISM: Classical swine fever virus

<400> SEQUENCE: 14
tgagcgcggg taacccggga tctgaacccg ccagtaggac cctattgtag ataacactaa        60
ttttcttttt tttcttttt atttatttag atattactat ttatttattt atttatttat       120
tgaatgagta agaactggta taaactacct caagttacca cactcactc attttttaaca      180 gcactttagc tggaaggaaa attcctgacg tccacagttg gactaaggta atttctaacg       240
gccc                                                                   244

<210> SEQ ID NO 15
<211> LENGTH: 229
<212> TYPE: DNA
<213> ORGANISM: Classical swine fever virus

<400> SEQUENCE: 15
tgagcatggt tggcccttga tcgggcccta tcagtagaac cctattgtaa ataacattaa        60
cttattaatt atttagatac tattatttat ttatttattt atttattgaa tgagcaagta      120
ctggtacaaa ctacctcatg ttaccacact acactcattt taacagcact ttagctggag      180
ggaaaaccct gacgtccaca gttggactaa ggtaatttcc taacggccc                  229

<210> SEQ ID NO 16
<211> LENGTH: 229
<212> TYPE: DNA
<213> ORGANISM: Bovine viral diarrhea virus 1

<400> SEQUENCE: 16
tgagacaaaa tgtatatatt gtaaataaat taatccatgt acatagtgta tataaatata        60
gttgggaccg tccacctcaa gaagacgaca cgcccaacac gcacagctaa acagtagtca      120
agattatcta cctcaagata acactacatt taatgcacac agcactttag ctgtatgagg      180
atacgcccga cgtctatagt tggactaggg aagacctcta acagccccc                  229

<210> SEQ ID NO 17
<211> LENGTH: 188
<212> TYPE: DNA
<213> ORGANISM: Bovine viral diarrhea virus 1

<400> SEQUENCE: 17
tgaaataaat gtatatattg tacataaatc tgtatatgta catattatat ataaacttag        60
ttgagattag tagtgatata tagttatcta ctcaagtaaa cactcactc aatgcacaca       120 gcactttagc tgtatgaggg aacacccgac gtccatggtt ggactaggga agacccttaa      180
cagccccca                                                              188

<210> SEQ ID NO 18
<211> LENGTH: 209
<212> TYPE: DNA
<213> ORGANISM: Bovine viral diarrhea virus 2

<400> SEQUENCE: 18
tgaatctgcc cagagagtcg tgccctcact caaggtgtca tttgtaaata tggtgaatag        60
```

```
acagctaaga tatatattgt agttggatag taatgtagtg atagtagata ccccgattta      120
acactacctc caatgcacta agcactttag ctgtgtgagg ttaactcgac gtccatggtt      180
ggactagagg atggctctaa cggtccccc                                        209

<210> SEQ ID NO 19
<211> LENGTH: 194
<212> TYPE: RNA
<213> ORGANISM: Bovine viral diarrhea virus

<400> SEQUENCE: 19
ugaaauaaug uauguauaua uuguauauaa aucuguauuu guauauauua uguuuaaauu       60
uaguugagau uaguagugau auauaguuau cuaccucaag cuaacacuac acucaaugca      120
cacacagcac uuuagcugua ugagguaca cccgacgucc auaguuggac uagggaagac       180
cuuuaacagc cccc                                                        194

<210> SEQ ID NO 20
<211> LENGTH: 12
<212> TYPE: RNA
<213> ORGANISM: Border disease virus

<400> SEQUENCE: 20
aauuguauau au                                                           12

<210> SEQ ID NO 21
<211> LENGTH: 12
<212> TYPE: RNA
<213> ORGANISM: Border disease virus

<400> SEQUENCE: 21
gauuguauau aa                                                           12

<210> SEQ ID NO 22
<211> LENGTH: 12
<212> TYPE: RNA
<213> ORGANISM: Classical swine fever virus

<400> SEQUENCE: 22
uauuguagau aa                                                           12

<210> SEQ ID NO 23
<211> LENGTH: 12
<212> TYPE: RNA
<213> ORGANISM: Classical swine fever virus

<400> SEQUENCE: 23
uauuguaaau aa                                                           12

<210> SEQ ID NO 24
<211> LENGTH: 12
<212> TYPE: RNA
<213> ORGANISM: Bovine viral diarrhea virus 1

<400> SEQUENCE: 24
uaguguauau aa                                                           12

<210> SEQ ID NO 25
<211> LENGTH: 12
<212> TYPE: RNA
<213> ORGANISM: Bovine viral diarrhea virus 1

<400> SEQUENCE: 25
```

```
uauuauauau aa                                                    12

<210> SEQ ID NO 26
<211> LENGTH: 12
<212> TYPE: RNA
<213> ORGANISM: Bovine viral diarrhea virus 1

<400> SEQUENCE: 26
uauuguacau aa                                                    12

<210> SEQ ID NO 27
<211> LENGTH: 12
<212> TYPE: RNA
<213> ORGANISM: Bovine viral diarrhea virus 1

<400> SEQUENCE: 27
uauuauguuu aa                                                    12

<210> SEQ ID NO 28
<211> LENGTH: 12
<212> TYPE: RNA
<213> ORGANISM: Bovine viral diarrhea virus 1

<400> SEQUENCE: 28
uauuguacau aa                                                    12

<210> SEQ ID NO 29
<211> LENGTH: 12
<212> TYPE: RNA
<213> ORGANISM: Bovine viral diarrhea virus 2

<400> SEQUENCE: 29
aaauauggug aa                                                    12

<210> SEQ ID NO 30
<211> LENGTH: 12
<212> TYPE: RNA
<213> ORGANISM: Bovine viral diarrhea virus

<400> SEQUENCE: 30
uauuguauau aa                                                    12

<210> SEQ ID NO 31
<211> LENGTH: 12
<212> TYPE: RNA
<213> ORGANISM: Bovine viral diarrhea virus

<400> SEQUENCE: 31
uauuguaaau aa                                                    12

<210> SEQ ID NO 32
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 32
tattgtatat aa                                                    12

<210> SEQ ID NO 33
<211> LENGTH: 12
<212> TYPE: DNA
```

```
<213> ORGANISM: Artificial Sequence
<220> FEATURE:
<223> OTHER INFORMATION: Synthetic oligonucleotide

<400> SEQUENCE: 33
tattatgttt aa                                                          12
```